US 8,329,737 B2

(12) United States Patent
Styles et al.

(10) Patent No.: US 8,329,737 B2
(45) Date of Patent: Dec. 11, 2012

(54) BENZIMIDAZOLES AS SELECTIVE KINASE INHIBITORS

(75) Inventors: Michelle Leanne Styles, London (GB); Jun Zeng, Doncaster East (AU); Herbert Rudolf Treutlein, Moonee Ponds (AU); Andrew Frederick Wilks, South Yarra (AU); Marcel Robert Kling, Bentleigh (AU); Xianyong Bu, Viewbank (AU); Christopher John Burns, Richmond (AU)

(73) Assignee: YM Biosciences Australia PTY Ltd, Melbourne Victoria (AU)

( * ) Notice: Subject to any disclaimer, the term of this patent is extended or adjusted under 35 U.S.C. 154(b) by 0 days.

(21) Appl. No.: 12/895,548

(22) Filed: Sep. 30, 2010

(65) Prior Publication Data
US 2011/0082142 A1    Apr. 7, 2011

Related U.S. Application Data

(63) Continuation of application No. 10/585,916, filed as application No. PCT/AU2005/000022 on Jan. 12, 2005, now abandoned.

(30) Foreign Application Priority Data

Jan. 12, 2004  (AU) .................................. 2004900103

(51) Int. Cl.
*A61K 31/415*    (2006.01)

(52) U.S. Cl. ..... 514/394; 544/333; 544/405; 546/268.1; 548/306.1

(58) Field of Classification Search .................. 514/394; 544/333, 405; 546/268.1; 548/306.1
See application file for complete search history.

(56) References Cited

U.S. PATENT DOCUMENTS

| 5,990,146 | A  | 11/1999 | Boschelli et al. |
| 6,329,380 | B1 | 12/2001 | Goulet et al. |
| 6,498,165 | B1 | 12/2002 | Armstrong et al. |

FOREIGN PATENT DOCUMENTS

| EP | 0 111 993    | 6/1984  |
| WO | WO-01/00207  | 1/2001  |
| WO | WO-01/00213  | 1/2001  |
| WO | WO-03/099811 | 12/2003 |

OTHER PUBLICATIONS

Chawla et al., Curr. Res. & Info. Pharm. Sci. (CRIPS) (2004) 5(1):9-12.
Discafani et al., Biochem. Pharmacol. (1999) 57:917-925.
Dorwald, Side Reactions in Organic Synthesis: A Guide to Successful Synthesis Design, Weinheim: Wiley-VCH Verlag GmbH & Co. KGaA (2005) preface.
Finet et al., Curr. Org. Chem. (2002) 6:597-626.
Fry et al., PNAS USA (1998) 95:12022-12027.
Hovens et al., PNAS USA (1992) 89:11818-11822.
International Search Report for PCT/AU2005/000022, mailed on Mar. 17, 2005, 3 pages.
Jordan, Nature Reviews: Drug Discovery (2003) 2:205.
Kozma et al., EMBO J. (1988) 7:147-154.
Kumada et al., Org. Synth. Coll. (1988) 6:407.
Levitzki, Top. Curr. Chem. (2000) 211:1-15.
Miyaura and Suzuki, Chem. Rev. (1995) 95:2457.
Negishi, J. Organomet. Chem. (2002) 653:34-40.
Russell et al., Science (1995) 270:797-800.
Sadowski et al., Mol. Cell Biol. (1986) 6:4396-4408.
Smaill et al., J. Med. Chem. (1999) 42:1803-1815.
Smaill et al., J. Med. Chem. (2000) 43:1380-1397.
Smaill et al., J. Med. Chem. (2001) 44:429-440.
Spiotto and Chung, Prostate (2000) 42:88-98.
Stille, Angew. Chem. Int. Ed. Engl. (1986) 25:508.
Supplementary European Search Report for EP 05700054.9, mailed on Jul. 6, 2009, 3 pages.
Tsou et al., J. Med. Chem. (2001) 44:2719-2734.
Vippagunta et al., Advanced Drug Delivery Reviews (2001) 48:18.
Wilks and Kurban, Oncogene (1988) 3:289-294.
Wilks et al., Mol. Cell Biol. (1991) 11:2057-2065.
Wissner et al., J. Med. Chem. (2003) 46:49-63.
Wolff, (ed.), Burger's Medicinal Chemistry and Drug Discovery, 5th ed., New York: John Wiley & Sons, (1996) vol. 1, pp. 975-976.

*Primary Examiner* — Douglas M Willis
(74) *Attorney, Agent, or Firm* — Morrison & Foerster LLP

(57) ABSTRACT

A compound of the general formula (I) or pharmaceutically acceptable prodrugs, salts, hydrates, solvates, crystal forms or diastereomers thereof, wherein A represents a variety of six membered nitrogen containing heterocyclic rings, Q is a bond, halogen, $C_{1-4}$ alkyl, O, S, $SO_2$, CO or CS and $X_1$, $X_2$, $X_3$ and $X_4$ are optionally substituted by 9 specific substituents or one can be nitrogen. Compositions comprising a carrier and at least one compound of formula (I) are also provided. Further provided are methods of treating tyrosine kinase-associated disease states by administering a compound of formula (I) and methods of suppressing the immune system of a subject by administering a compound of formula (I).

4 Claims, 2 Drawing Sheets

```
j2h  :SGAFEDRDPTQFEERHLKFLQQLGKGNFGSVEMCRYDPLQDNTGEVVAVKKL-QHSTEEHLRDFEREIEIL:70
j1h  :KNQPTEVDPTHFEKRFLKRIRDLGEGHFGKVELCRYDPEDN-TGEQVAVKSLKPESGGNHIADLKKEIEIL:70
j3h  :AQLYACQDPTIFEERHLKYISQLGKGNFGSVELCRYDPLAHNTGALVAVKQL-QHSGPDQQRDFQREIQIL:70
tyk2 :NRDSPAVGPTTFHKRYLKKIRDLGEGHFGKVSLYCYDPTNDGTGEMVAVKALKADCGPQHRSGWKQEIDIL:71
         dPT Fe R LK I  LG G FG VElCrYDP      TGe VAVK L  sg h d    EI IL j2h  :KSLQHDNIVKYKGVCYSAGRRNLKLIMEYLPYGSLRDYLQKHKERIDHIKLLQYTSQICKGMEYLGTKRYI:141
j1h  :RNLYHENIVKYKGICTEDGGNGIKLIMEFLPSGSLKEYLPKNKNKINLKQQLKYAVQICKGMDYLGSRQYV:141
j3h  :KALHSDFIVKYRGVSYGPGRPELRLVMEYLPSGCLRDFLQRHRARLDASRLLLYSSQICKGMEYLGSRRCV:141
tyk2 :RTLYHEHIIKYKGCCEDQGEKSLQLVMEYVPLGSLRDYLPRHSIGL-A-QLLLFAQQICEGMAYLHAHDYI:140
         L h   IvKyKG c  G    I L MEyIP GsLrdyL h          IL y  QICkGM YLg  y j2h  :HRDLATRNILVENENRVKIGDFEGLTKVLPQDKEYYKVKEPGESPIFWYAPESLTESKFSVASDVWSFGVVL:212
j1h  :HRDLAARNVLVESEHQVKIGDFGLTKAIETDKEYYTVKDDRDSPVFWYAPECLMQSKFYIASDVWSFGVTL:212
j3h  :HRDLAARNILVESEAHVKIADFGLAKLLPLDKDYYVVREFGQSPIFWYAPESLSDNIFSRQSDVWSFGVVL:212
tyk2 :HRDLAARNVLLDNDRLVKIGDFGLAKAVPEGHEYYRVREDGDSPVFWYAPECLKEYKFYYASDVWSFGVTL:211
      HRDLAaRN Lve e  VKIgDFGL K  P dkeYY V e g SP FWYAPE L  kF aSDVWS FGV L j2h  :YELFTYIEKSKSPPAEFMRMIGNDKQGQMIVFHLIELLKNNGRLPRPDGCPDEIYMIMTECWNNNVNQRPS:283
j1h  :HELLTYCDSDSSPMALFLKMIG-PTHGQMTVTRLVNTLKEGKRLPCPPNCPDEVYQLMRKCWEFQPSNRTS:282
j3h  :YELFTYCDKSCSPSAEFLRMMGCERD-VPALCRLLELLEEGQRLPAPPACPAEVHELMKLCWAPSPQDRPS:282
tyk2 :YELLTHCDSSQSPPTKFLELIGIA-QGQMTVLRLTELLERGERLPRPDKCPCEVYHLMKNCWETEASFRPT:281
       yEL Tycd s SP a FI mIG     gqm v rL eIL g  RLP  P  CP Evy IM  CW   Rps j2h  :FRDLALRVDQIRDNMAG:300
j1h  :FQNLIEGFEALLK---:295
j3h  :FSALGPQLDMLWSGSRG:299
tyk2 :FENLIPILKTVHEKY--:296
      F        L
```

FIG. 1

SEQUENCE LISTING

<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Primer XHOI-J1

<400> SEQUENCE: 1
ccgctcgaga ctgaagtgga ccccacacat                              30

<210> SEQ ID NO 2
<211> LENGTH: 30
<212> TYPE: DNA
<213> ORGANISM: Artificial Sequence
<220> FEATURE:
<223> OTHER INFORMATION: Primer J1-KPNI

<400> SEQUENCE: 2
cggggtacct tattttaaaa gtgcttcaaa                              30

<210> SEQ ID NO 3
<211> LENGTH: 31
<212> TYPE: DNA
<213> ORGANISM: Artificial Sequence
<220> FEATURE:
<223> OTHER INFORMATION: Primer SALI-jk2

<400> SEQUENCE: 3
acgcgtcgac ggtgcctttg aagaccggga t                            31

<210> SEQ ID NO 4
<211> LENGTH: 34
<212> TYPE: DNA
<213> ORGANISM: Artificial Sequence
<220> FEATURE:
<223> OTHER INFORMATION: Primer jk2-NOTI

<400> SEQUENCE: 4
atagtttagc ggccgctcag aatgaaggtc attt                         34

<210> SEQ ID NO 5
<211> LENGTH: 30
<212> TYPE: DNA
<213> ORGANISM: Artificial Sequence
<220> FEATURE:
<223> OTHER INFORMATION: Primer XHOI-J3

<400> SEQUENCE: 5
ccgctcgagt atgcctgcca agaccccacg                              30

<210> SEQ ID NO 6
<211> LENGTH: 30
<212> TYPE: DNA
<213> ORGANISM: Artificial Sequence
<220> FEATURE:
<223> OTHER INFORMATION: Primer J3-KPNI

<400> SEQUENCE: 6
cggggtaccc tatgaaaagg acagggagtg                              30

<210> SEQ ID NO 7
<211> LENGTH: 33
<212> TYPE: DNA
<213> ORGANISM: Artificial Sequence
<220> FEATURE:
<223> OTHER INFORMATION: Primer HT2EK

<400> SEQUENCE: 7
ggagcactcg agatggtagc acacaaccag gtg                          33

<210> SEQ ID NO 8
<211> LENGTH: 35
<212> TYPE: DNA
<213> ORGANISM: Artificial Sequence
<220> FEATURE:
<223> OTHER INFORMATION: Primer ITY2.2R

<400> SEQUENCE: 8
ggagcaggaa ttccggcgct gccggtcaaa tctgg                                35

<210> SEQ ID NO 9
<211> LENGTH: 17
<212> TYPE: PRT
<213> ORGANISM: Artificial Sequence
<220> FEATURE:
<223> OTHER INFORMATION: Biotinylated substrate

<400> SEQUENCE: 9

Glu Gly Pro Trp Leu Glu Glu Glu Glu Ala Tyr Gly Trp Met Asp
1               5                   10                  15

Phe

<210> SEQ ID NO 10
<211> LENGTH: 300
<212> TYPE: PRT
<213> ORGANISM: Artificial Sequence
<220> FEATURE:
<223> OTHER INFORMATION: JAK2 Kinase j2h

<400> SEQUENCE: 10

Ser Gly Ala Phe Glu Asp Arg Asp Pro Thr Gln Phe Glu Glu Arg His
1               5                   10                  15

Leu Lys Phe Leu Gln Gln Leu Gly Lys Gly Asn Phe Gly Ser Val Glu
            20                  25                  30

Met Cys Arg Tyr Asp Pro Leu Gln Asp Asn Thr Gly Glu Val Val Ala
        35                  40                  45

Val Lys Lys Leu Gln His Ser Thr Glu Glu His Leu Arg Asp Phe Glu
50                  55                  60

Arg Glu Ile Glu Ile Leu Lys Ser Leu Gln His Asp Asn Ile Val Lys
65                  70                  75                  80

Tyr Lys Gly Val Cys Tyr Ser Ala Gly Arg Arg Asn Leu Lys Leu Ile
                85                  90                  95

Met Glu Tyr Leu Pro Tyr Gly Ser Leu Arg Asp Tyr Leu Gln Lys His
            100                 105                 110

Lys Glu Arg Ile Asp His Ile Lys Leu Leu Gln Tyr Thr Ser Gln Ile
        115                 120                 125

Cys Lys Gly Met Glu Tyr Leu Gly Thr Lys Arg Tyr Ile His Arg Asp
130                 135                 140

Leu Ala Thr Arg Asn Ile Leu Val Glu Asn Glu Asn Arg Val Lys Ile
145                 150                 155                 160

Gly Asp Phe Gly Leu Thr Lys Val Leu Pro Gln Asp Lys Glu Tyr Tyr
                165                 170                 175

Lys Val Lys Glu Pro Gly Glu Ser Pro Ile Phe Trp Tyr Ala Pro Glu
            180                 185                 190

Ser Leu Thr Glu Ser Lys Phe Ser Val Ala Ser Asp Val Trp Ser Phe
        195                 200                 205

Gly Val Val Leu Tyr Glu Leu Phe Thr Tyr Ile Glu Lys Ser Lys Ser
210                 215                 220

Pro Pro Ala Glu Phe Met Arg Met Ile Gly Asn Asp Lys Gln Gly Gln
225                 230                 235                 240

```
Met Ile Val Phe His Leu Ile Glu Leu Leu Lys Asn Asn Gly Arg Leu
                245                 250                 255

Pro Arg Pro Asp Gly Cys Pro Asp Glu Ile Tyr Met Ile Met Thr Glu
            260                 265                 270

Cys Trp Asn Asn Asn Val Asn Gln Arg Pro Ser Phe Arg Asp Leu Ala
        275                 280                 285

Leu Arg Val Asp Gln Ile Arg Asp Asn Met Ala Gly
        290                 295                 300

<210> SEQ ID NO 11
<211> LENGTH: 295
<212> TYPE: PRT
<213> ORGANISM: Artificial Sequence
<220> FEATURE:
<223> OTHER INFORMATION: JAK2 Kinase j1h

<400> SEQUENCE: 11

Lys Asn Gln Pro Thr Glu Val Asp Pro Thr His Phe Glu Lys Arg Phe
1               5                   10                  15

Leu Lys Arg Ile Arg Asp Leu Gly Glu Gly His Phe Gly Lys Val Glu
            20                  25                  30

Leu Cys Arg Tyr Asp Pro Glu Asp Asn Thr Gly Glu Gln Val Ala Val
        35                  40                  45

Lys Ser Leu Lys Pro Glu Ser Gly Gly Asn His Ile Ala Asp Leu Lys
50                  55                  60

Lys Glu Ile Glu Ile Leu Arg Asn Leu Tyr His Glu Asn Ile Val Lys
65                  70                  75                  80

Tyr Lys Gly Ile Cys Thr Glu Asp Gly Gly Asn Gly Ile Lys Leu Ile
                85                  90                  95

Met Glu Phe Leu Pro Ser Gly Ser Leu Lys Glu Tyr Leu Pro Lys Asn
            100                 105                 110

Lys Asn Lys Ile Asn Leu Lys Gln Gln Leu Lys Tyr Ala Val Gln Ile
        115                 120                 125

Cys Lys Gly Met Asp Tyr Leu Gly Ser Arg Gln Tyr Val His Arg Asp
130                 135                 140

Leu Ala Ala Arg Asn Val Leu Val Glu Ser Glu His Gln Val Lys Ile
145                 150                 155                 160

Gly Asp Phe Gly Leu Thr Lys Ala Ile Glu Thr Asp Lys Glu Tyr Tyr
                165                 170                 175

Thr Val Lys Asp Asp Arg Asp Ser Pro Val Phe Trp Tyr Ala Pro Glu
            180                 185                 190

Cys Leu Met Gln Ser Lys Phe Tyr Ile Ala Ser Asp Val Trp Ser Phe
        195                 200                 205

Gly Val Thr Leu His Glu Leu Leu Thr Tyr Cys Asp Ser Asp Ser Ser
210                 215                 220

Pro Met Ala Leu Phe Leu Lys Met Ile Gly Pro Thr His Gly Gln Met
225                 230                 235                 240

Thr Val Thr Arg Leu Val Asn Thr Leu Lys Glu Gly Lys Arg Leu Pro
                245                 250                 255

Cys Pro Pro Asn Cys Pro Asp Glu Val Tyr Gln Leu Met Arg Lys Cys
            260                 265                 270

Trp Glu Phe Gln Pro Ser Asn Arg Thr Ser Phe Gln Asn Leu Ile Glu
        275                 280                 285

Gly Phe Glu Ala Leu Leu Lys
        290                 295
```

<210> SEQ ID NO 12
<211> LENGTH: 299
<212> TYPE: PRT
<213> ORGANISM: Artificial Sequence
<220> FEATURE:
<223> OTHER INFORMATION: JAK2 Kinase j3h

<400> SEQUENCE: 12

```
Ala Gln Leu Tyr Ala Cys Gln Asp Pro Thr Ile Phe Glu Glu Arg His
  1               5                  10                  15

Leu Lys Tyr Ile Ser Gln Leu Gly Lys Gly Asn Phe Gly Ser Val Glu
             20                  25                  30

Leu Cys Arg Tyr Asp Pro Leu Ala His Asn Thr Gly Ala Leu Val Ala
         35                  40                  45

Val Lys Gln Leu Gln His Ser Gly Pro Asp Gln Gln Arg Asp Phe Gln
 50                  55                  60

Arg Glu Ile Gln Ile Leu Lys Ala Leu His Ser Asp Phe Ile Val Lys
 65                  70                  75                  80

Tyr Arg Gly Val Ser Tyr Gly Pro Gly Arg Pro Glu Leu Arg Leu Val
             85                  90                  95

Met Glu Tyr Leu Pro Ser Gly Cys Leu Arg Asp Phe Leu Gln Arg His
            100                 105                 110

Arg Ala Arg Leu Asp Ala Ser Arg Leu Leu Leu Tyr Ser Ser Gln Ile
        115                 120                 125

Cys Lys Gly Met Glu Tyr Leu Gly Ser Arg Arg Cys Val His Arg Asp
130                 135                 140

Leu Ala Ala Arg Asn Ile Leu Val Glu Ser Glu Ala His Val Lys Ile
145                 150                 155                 160

Ala Asp Phe Gly Leu Ala Lys Leu Leu Pro Leu Asp Lys Asp Tyr Tyr
            165                 170                 175

Val Val Arg Glu Pro Gly Gln Ser Pro Ile Phe Trp Tyr Ala Pro Glu
        180                 185                 190

Ser Leu Ser Asp Asn Ile Phe Ser Arg Gln Ser Asp Val Trp Ser Phe
    195                 200                 205

Gly Val Val Leu Tyr Glu Leu Phe Thr Tyr Cys Asp Lys Ser Cys Ser
210                 215                 220

Pro Ser Ala Glu Phe Leu Arg Met Met Gly Cys Glu Arg Asp Val Pro
225                 230                 235                 240

Ala Leu Cys Arg Leu Leu Glu Leu Leu Glu Glu Gly Gln Arg Leu Pro
            245                 250                 255

Ala Pro Pro Ala Cys Pro Ala Glu Val His Glu Leu Met Lys Leu Cys
        260                 265                 270

Trp Ala Pro Ser Pro Gln Asp Arg Pro Ser Phe Ser Ala Leu Gly Pro
    275                 280                 285

Gln Leu Asp Met Leu Trp Ser Gly Ser Arg Gly
290                 295
```

<210> SEQ ID NO 13
<211> LENGTH: 296
<212> TYPE: PRT
<213> ORGANISM: Artificial Sequence
<220> FEATURE:
<223> OTHER INFORMATION: JAK2 Kinase tyk2

```
<400> SEQUENCE: 13

Asn Arg Asp Ser Pro Ala Val Gly Pro Thr Thr Phe His Lys Arg Tyr
1               5                   10                  15

Leu Lys Lys Ile Arg Asp Leu Gly Glu Gly His Phe Gly Lys Val Ser
                20                  25                  30

Leu Tyr Cys Tyr Asp Pro Thr Asn Asp Gly Thr Gly Glu Met Val Ala
            35                  40                  45

Val Lys Ala Leu Lys Ala Asp Cys Gly Pro Gln His Arg Ser Gly Trp
50                  55                  60

Lys Gln Glu Ile Asp Ile Leu Arg Thr Leu Tyr His Glu His Ile Ile
65                  70                  75                  80

Lys Tyr Lys Gly Cys Cys Glu Asp Gln Gly Glu Lys Ser Leu Gln Leu
                85                  90                  95

Val Met Glu Tyr Val Pro Leu Gly Ser Leu Arg Asp Tyr Leu Pro Arg
                100                 105                 110

His Ser Ile Gly Leu Ala Gln Leu Leu Leu Phe Ala Gln Gln Ile Cys
            115                 120                 125

Glu Gly Met Ala Tyr Leu His Ala His Asp Tyr Ile His Arg Asp Leu
130                 135                 140

Ala Ala Arg Asn Val Leu Leu Asp Asn Asp Arg Leu Val Lys Ile Gly
145                 150                 155                 160

Asp Phe Gly Leu Ala Lys Ala Val Pro Glu Gly His Glu Tyr Tyr Arg
                165                 170                 175

Val Arg Glu Asp Gly Asp Ser Pro Val Phe Trp Tyr Ala Pro Glu Cys
                180                 185                 190

Leu Lys Glu Tyr Lys Phe Tyr Tyr Ala Ser Asp Val Trp Ser Phe Gly
            195                 200                 205

Val Thr Leu Tyr Glu Leu Leu Thr His Cys Asp Ser Ser Gln Ser Pro
210                 215                 220

Pro Thr Lys Phe Leu Glu Leu Ile Gly Ile Ala Gln Gly Gln Met Thr
225                 230                 235                 240

Val Leu Arg Leu Thr Glu Leu Leu Glu Arg Gly Glu Arg Leu Pro Arg
                245                 250                 255

Pro Asp Lys Cys Pro Cys Glu Val Tyr His Leu Met Lys Asn Cys Trp
                260                 265                 270

Glu Thr Glu Ala Ser Phe Arg Pro Thr Phe Glu Asn Leu Ile Pro Ile
            275                 280                 285

Leu Lys Thr Val His Glu Lys Tyr
290                 295
```

BENZIMIDAZOLES AS SELECTIVE KINASE INHIBITORS

CROSS-REFERENCE TO RELATED APPLICATIONS

This application is a continuation of U.S. application Ser. No. 10/585,916, filed 11 Jul. 2006, which is a national phase of PCT application PCT/AU2005/000022 having an international filing date of 12 Jan. 2005, which claims priority from Australian Application No. 2004900103 filed 12 Jan. 2004. The contents of these documents are incorporated herein by reference.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 415852001101Seqlist.txt | Sep. 30, 2010 | 12,455 bytes |

FIELD OF THE INVENTION

The present invention relates to the field of inhibitors of protein tyrosine kinases in particular the JAK family of protein tyrosine kinases.

BACKGROUND OF THE INVENTION

Protein kinases area family of enzymes that catalyse the phosphorylation of specific residues in proteins. In general protein kinases fall into several groups; those which preferentially phosphorylate serine and/or threonine residues, these which preferentially phosphorylate tyrosine residues and those which phosphorylate both tyrosine and Ser/Thr residues. Protein kinases are therefore key elements in signal transduction pathways responsible for transducing extracellular signals, including the action of cytokines on their receptors, to the nuclei, triggering various biological events. The many roles of protein kinases in normal cell physiology include cell cycle control and cell growth, differentiation, apoptosis, cell mobility and mitogenesis.

Protein kinases include, for example, but are not limited to, members of the Protein, Tyrosine Kinase family (PTKs), which in turn can be divided into the cytoplasmic PTKs and the receptor PTKs (RTKs). The cytoplasmic PTKs include the SRC family, (including: BLK; FGR; FYN; HCK; LCK; LYN; SRC; YES and YRK); the BRK Family (including: BRK; FRK; SAD; and SRM); the CSK family (including: CSK and CTK); the BTK family, (including BTK; ITK; TEC; MKK2 and TXK), the Janus kinase family, (including: JAK1, JAK2, JAK3 and TYK2), the FAK family (including, FAK and PYK2); the Fes family (including FES and FER); the ZAP70 family (including ZAP70 and SYK); the ACK family (including ACK1 and ACK2); and the Abl family (including ABL and ARG). The RTK family includes the EGF-Receptor family (including, EGFR, HER2, HER3 and HER4); the Insulin Receptor family (including INS-R and IGF1-R); the PDGF-Receptor family (including PDGFRα, PDGFRβ, CSF1R, KIT, FLK2); the VEGF-Receptor family (including: FLT1, FLK1 and FLT4); the FGF-Receptor family (including FGFR1, FGFR2, FGFR3 and FGFR4); the CCK4 family (including CCK4); the MET family (including MET and RON); the TRK family (including TRKA, TRKB, and TRKC); the AXL family (including AXL, MER, and SKY); the TIE/TEK family (including TIE and TIE2/TEK); the EPH family (including EPHA1, EPHA2, EPHA3, EPHA4, EHPA5, EPHA6, EPHA7, EPHA8, EPHB1, EPHB2, EPHB3, EPHB4, EPHB5, EPHB6); the RYK family (including RYK); the MCK family (including MCK and TYRO10); the ROS family (including ROS); the RET family (including RET); the LTK family (including LTK and ALK); the ROR family (including ROR1 and ROR2); The Musk family (including Musk); the LMR family including LMR1, LMR2 and LMR3; and the SuRTK106 family (including SuRTK106).

Similarly, the serine/threonine specific kinases comprise a number of distinct subfamilies, including; the extracellular signal regulated kinases, (p42/ERK2 and p44/ERK1); c-Jun NH2-terminal kinase (JNK); cAMP-responsive element-binding protein kinases (CREBK); cAMP-dependent kinase (CAPK); mitogen-activated protein kinase-activated protein kinase (MAPK and its relatives); stress-activated protein kinase p38/SAPK2; mitogen- and stress-activated kinase (MSK); protein kinases, PKA, PKB and PKC inter alia.

Additionally, the genomes of a number of pathogenic organisms possess genes encoding protein kinases. For example, the malarial parasite *Plasmodium falciparum* and viruses such as HPV and Hepatitis viruses appear to bear kinase related genes.

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signals upstream or downstream of the kinase. In all of these instances, selective inhibition of the action of the kinase might be expected to have a beneficial effect. Diseases where aberrant kinase activity has been implicated include: diabetes; restenosis; atherosclerosis; fibrosis of the liver end kidney; ocular diseases; myelo- and lymphoproliferative disorders; cancer such as prostate cancer, colon cancer, breast cancer, head and neck cancer, leukemia and lymphoma; and, auto-immune diseases such as Atopic Dermatitis, Asthma, rheumatoid arthritis, Crohn's disease, psoriasis, Crouzon syndrome, achondroplasia, and thanatophoric dysplasia.

The JAK family of protein tyrosine kinases (PTKs) play a central role in the cytokine dependent regulation of the proliferation and end function of several important cell types of the immune system.

A direct comparison of the four currently known mammalian JAK family members reveals the presence of seven highly conserved domains (Harpur, et al., 1992). In seeking a nomenclature for the highly conserved domains characteristic of this family of PTKs, the classification used was guided by the approach of Pawson and co-workers (Sadowski, et al., 1986) in their treatment of the SRC homology (SH) domains. The domains have been enumerated accordingly with most C-terminal homology domain designated JAK Homology domain 1 (JH1). The next domain N-terminal to JH1 is the kinase-related domain, designated here as the JH2 domain. Each domain is then enumerated up to the JH7 located at the N-terminus. The high degree of conservation of these JAK homology (JH) domains suggests that they are each likely to play an important role in the cellular processes in which these proteins operate. However, the boundaries of the JAK homology domains are arbitrary, and may or may not define functional domains. Nonetheless, their delineation is a useful device to aid the consideration of the overall structural similarity of this class of proteins.

The feature most characteristic of the JAK family of PTKs is the possession of two kinase-related domains all and JH2) (Wilks et al, 1991). The putative. PTK domain of JAK1 (JH1) contains highly conserved motifs typical of PTK domains, including the presence of a tyrosine residue at position 1022 located 11 residues C-terminal to sub-domain VII that is considered diagnostic of membership of the tyrosine-specific class of protein kinases Alignment of the human JAK1 PTK domain (255 amino acids), with other members of the PTK class of proteins revealed homology with other functional PTKs (for example, 28% identity with c-fes Milks and Kurban, 1988) and 37% homology to TRK (Kozinci at al, 1988)). The JH1 domains of each of the JAK family members possess an interesting idiosyncrasy within the highly conserved sub-domain VAT motif (resides 31015 to 1027 in JAK2) that is believed to lie close to the active site, and define substrate specificity. The phenylalanine and tyrosine residues flanking the conserved tryptophan in this motif are unique to the JAK family of PTKs. Aside from this element, the Jill domains of each of the members of the JAK family are typical PTK domains. Furthermore, there is high sequence identity in the JAK family particularly in and around the ATP binding site (FIG. 1).

The central role played by the JAK family of protein tyrosine kinases in the cytokine dependent regulation of the proliferation and end function of several important cell types means that agents which inhibit JAK are useful in the prevention and chemotherapy of disease states dependent on these enzymes. Potent and specific inhibitors of each of the currently known four JAK family members will provide a means of inhibiting the action of those cytokines that drive immune pathologies, such as asthma and as immunosuppressive agents for, amongst others, organ transplants, lupus, multiple sclerosis, rheumatoid arthritis, psoriasis, Type I diabetes and complications from diabetes, cancer, atopic dermatitis, autoimmune thyroid disorders, ulcerative colitis, Crohn's disease, Alzheimer's disease, and leukemia/lymphoma.

The JAK/STAT Pathway

The delineation of a particularly elegant signal transduction pathway downstream of the non-protein tyrosine kinase cytokine receptors has recently been achieved. In this pathway the key components are: (i) A cytokine receptor chain (or chains) such as the Interleukin-4 receptor or the Interferon γ receptor; (ii) a member (or members) of the JAK family of PTKs; (iii) a member(s) of the STAT family of transcription factors, and (iv) a sequence specific DNA element to which the activated STAT will bind.

A review of the JAK/STAT literature offers strong support to the notion that this pathway is important for the recruitment and marshalling of the host immune response to environmental insults, such as viral and bacterial infection. This is well exemplified in Table 1 and Table 2. Information accumulated from gene knock-out experiments have underlined the importance of members of the JAK family to the intracellular signalling triggered by a number of important immune regulatory cytokines. The therapeutic possibilities stemming from inhibiting (or enhancing) the JAK/STAT pathway are thus largely in the sphere of immune modulation, and as such are likely to be promising drugs for the treatment of a range of pathologies in this area. In addition to the diseases listed in Tables 1 and 2, inhibitors of JAKs could be used as immunosuppressive agents for organ transplants and autoimmune diseases such as lupus, multiple sclerosis, rheumatoid arthritis, Type I diabetes, autoimmune thyroid disorders, Alzheimer's disease and other autoimmune diseases. Additionally, treatment of cancers such as prostate cancer by JAK inhibitors is indicated.

TABLE 1

Activation of the JAK/STAT pathway in various pathologies

| Disease Type | Cell Types Involved | Characteristics |
|---|---|---|
| Atopy | | |
| Allergic Asthma | (Mast Cells | T-cell activation of B-cells |
| Atopic Dermatitis (Eczema) | (Eosinophils | followed by IgE mediated |
| Allergic Rhinitis | (T-Cells | activation of resident Mast |
|  | (B-Cells | cells and Eosinophils |
| Cell Mediated Hypersensitivity | | |
| Allergic Contact Dermatitis | (T-cells | T-cell hypersensitivity |
| Hypersensitivity Pneumonitis | (B-cells | |
| Rheumatic Diseases | | |
| Systemic Lupus Erythematosus (SLE) | | |
| Rheumatoid Arthritis | (Monocytes | Cytokine Production |
| Juvenile Arthritis | (Macrophages | (e.g. TNF, IL-1, CSF-1, GM-CSF) |
| Sjögren's Syndrome | (Neutrophils | |
| Scleroderma | (Mast Cells | T-cell Activation |
| Polymyositis | (Eosinophils | JAK/STAT activation |
| Ankylosing Spondylitis | (T-Cells | |
| Psoriatic Arthritis | (B-Cells | |
| Transplantation | | |
| Transplant rejection | T-Cells & B-Cells | JAK/STAT Activation |
| Graft versus Host Disease | T-Cells & B-Cells | JAK/STAT Activation |

TABLE 1-continued

Activation of the JAK/STAT pathway in various pathologies

| Disease Type | Cell Types Involved | Characteristics |
|---|---|---|
| Viral Diseases | | |
| Epstein Barr Virus (EBV) | Lymphocytes | JAK/STAT Activation |
| Hepatitis B | Hepatocytes | JAK/STAT Activation |
| Hepatitis C | Hepatocytes | JAK/STAT Inhibition |
| HIV | Lymphocytes | JAK/STAT Activation |
| HTLV 1 | Lymphocytes | JAK/STAT Activation |
| Varicella-Zoster Virus (VZV) | Fibroblasts | JAK/STAT Inhibition |
| Human Papilloma Virus (HPV) | Epithelial cells | JAK/STAT Inhibition |
| Cancer | | |
| Leukemia | Leucocytes | (Cytokine production |
| Lymphoma | Lymphocytes | (JAK/STAT Activation |

TABLE 2

Diseases Potentially Treatable By JAK-Based Drug Therapies

| Target Disease | Cytokine | JAK family member | Strength of Association |
|---|---|---|---|
| Asthma | IL-4 & IL-9 | JAK1 & JAK3 | +++ |
| | IL-13 | JAK1 & JAK2 | +++ |
| | IL-5 | JAK2 | +++ |
| Eczema | IL-4 | JAK1 & JAK3 | +++ |
| | IFN-α | JAK1 & JAK2 | +++ |
| Food Allergy | IL-4 | JAK1 & JAK3 | +++ |
| Inflammatory Bowel Disease & Crohn's Disease | IL-4 | JAK1 & JAK3 | +++ |
| Leukaemia And Lymphoma Transplantation | (IL-2) | JAK3, JAK1 & JAK2 | +++ |
| B-Cell Maturation | IL-4 | JAK1 & JAK3 | +++ |
| T-Cell Proliferation | IL-2 | JAK1 & JAK3 | +++ |
| Cutaneous Inflammation | GM-CSF & IL-6 | JAK1 & JAK2 | +++ |
| Immune Suppression By Solid Tumour | IL-10 | JAK1 & TYK2 | +++ |
| Prostate Cancer | IL-6 | JAK1, JAK2 & Tyk2 | +++ |

Jak 3 Signalling

Although the other members of the Jak family are expressed by essentially all tissues, JAK3 expression appears to be limited to hematopoetic cells. This is consistent with its essential role in signaling through the receptors for IL-2, IL4, IL-7, IL-9 and IL-15 by non-covalent association of JAK3 with the gamma chain common to these multichain receptors. Males with X-linked severe combined immunodeficiency (XSCID) have defects in the common cytokine receptor gamma chain (gamma c) gene that encodes a shared, essential component of the receptors of interleukin-2 (IL-2), IL-4, IL-7, IL-9, and IL-15. An XSCID syndrome in which patients with either mutated or severely reduced levels of JAK3 protein has been identified, suggesting that immunosuppression should result from blocking signalling through the JAK3 pathway. Gene Knock out studies in mice have suggested that JAK3 not only plays a critical role in B and T lymphocyte maturation, but that JAK3 is constitutively required to maintain T cell function, Taken together with the biochemical evidence for the involvement of JAK3 in signalling events downstream of the IL-2 and IL-4 receptor, these human and mouse mutation studies suggest that modulation of immune activity through the inhibition of JAK3 could prove useful in the treatment of T-cell and B-cell proliferative disorders such as transplant rejection and autoimmune diseases.

Prolonged immunomodulation through inhibition of JAK3 signalling should have great therapeutic potential as long as JAK3 inhibition was achieved selectively and not accompanied by inhibition of other kinase-dependent signalling processes. In particular, the high degree of sequence identity held in common by members of the JAK family of kinases raises the possibility that a compound which inhibits Jak3 would also inhibit other members of the family with detrimental long term consequences. For example, prolonged inhibition of Jak2 is likely to lead to erythropenia and thrombocytopenia, since the receptors for both erythropoietin and thrombopoietin use only JAK2 for intracellular transmission of signals.

Selective and Irreversible Inhibition

A PTK catalyses the transfer of a phosphate group from a molecule of ATP to a tyrosine residue located on a protein substrate. The inhibitors known in the art are usually competitive with either the ATP or the protein substrate of the kinase (Levitzki 2000). Since the concentration of ATP in a cell is normally very high (millimolar), compounds that are competitive with ATP may lack in vivo activity since it is unlikely that said compounds can reach the concentrations within the cell that are necessary to displace the ATP from its binding site.

An alternative approach which has been attempted in relation to EGFR is to design or select compounds which bind to EGFR TK in an irreversible manlier. Such compounds are disclosed in Fry 1998; Discafani 1999; Smaill 1999; Smaill 2000; Tsou 2001; Smaill 2001; Wissner 2003. These compounds function as irreversible inhibitors by virtue of the fact that they can form covalent bonds to amino acid residues located at the active site of the enzyme which results in enhanced potency of the compounds in vitro and in the inhibition of growth of human tumors in in vivo models of cancer. A further benefit of such irreversible inhibitors when compared to reversible inhibitors, is that irreversible inhibitors can be used in prolonged suppression of the tyrosine kinase, limited only by the normal rate of receptor turnover.

The high homology between members of the JAK family of kinases makes the design of compounds with acceptable selectivity highly challenging. It is believed that by exploiting the minor differences in the amino acid sequence between the members of this family may allow for the identification of selective inhibitors. Alignment of the four members of the JAK family of protein tyrosine kinases reveals that within the amino acids that comprise the ATP-binding pocket of these kinases there are very few amino acid differences that could be used to target potential inhibitors towards one family member or another. Interestingly, JAK3 alone amongst this subfamily of kinases possesses a Cysteine residue close to the front lip of the ATP-binding cavity. It was hypothesised that this may provide a means to develop highly specific irreversible JAK3 inhibitors (FIG. 2), by targeting this Cysteine with a functionality bearing an alkylating group such as a Michael acceptor.

SUMMARY OF THE INVENTION

The present inventors have found that a group of compounds based upon a disubstituted heterocyclic scaffold which include an alkylating group such as a Michael acceptor are irreversible and selective inhibitors of the enzyme Janus Kinase 3 and as will find applications in therapy as immunosuppressive agents for organ transplants, lupus, multiple sclerosis, rheumatoid arthritis, psoriasis, Type I diabetes and complications from diabetes, asthma, staple dermatitis, autoimmune thyroid disorders, ulcerative Crohn's disease, and other indications where immunosuppression would be desirable. Furthermore, it is believed that these compounds may find application in therapeutic treatments for proliferative diseases and cancers such as Leukemia and Lymphoma where JAK3 is hyperactivated and in diseases such as Alzheimer's disease.

Accordingly, in a first aspect the present invention provides a compound of the general formula I

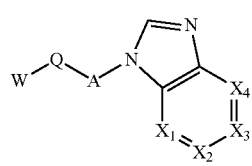

or pharmaceutically acceptable prodrugs, salts, hydrates, solvates, crystal forms or diastereomers thereof, wherein:
$X_1$, $X_2$, $X_3$, $X_4$ are each carbon where one is substituted with Z and the rest independently with Y; or one of $X_1$, $X_2$, $X_3$, $X_4$ is N, and the others are carbon where one carbon is substituted with Z and the rest independently with Y;

A is a ring selected from:

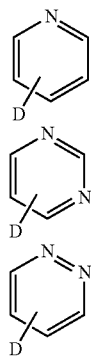

where D is selected from H, $C_{1-4}$ alkyl, halogen, amino;
Q is a bond, halogen, $C_{1-4}$ alkyl, O, S, SO, $SO_2$, CO, CS;
W is:
  (i) NR1R2 where R1 and R2 are independently H, $C_{1-4}$ alkyl, $C_{1-4}$ alkyl$CF_3$, aryl, hetaryl, $C_{1-4}$ alkylaryl, $C_{1-4}$ alkylhetaryl, $C_{3-8}$ cycloalkyl, $C_{2-6}$ alkenyl, cyclohetalkyl, $C_{1-4}$ alkylcycloalkyl, $C_{1-4}$ alkyl cyclohetalkyl, or R1 and R2 are joined to form an optionally substituted 3-8 membered ring optionally containing an atom selected from O, S, NR3; and R3 is selected from H, $C_{1-4}$ alkyl, aryl, hetaryl, $C_{1-4}$ alkyl aryl, $C_{1-4}$ alkyl hetaryl, COR4 where R4 is selected from H, $C_{1-4}$ alkyl, aryl, hetaryl;

OR (ii) H, $C_{1-4}$ alkyl, aryl, hetaryl, $C_{3-8}$ cycloalkyl, cyclohetalkyl, $C_{1-4}$ alkylaryl, $C_{1-4}$ alkylhetaryl, $C_{3-8}$ cycloalkyl, $C_{1-4}$ alkylcycloalkyl, $C_{1-4}$ alkyl cyclohetalkyl;

Y is H, halogen, CN, $CF_3$, nitro, OH, $C_{1-4}$ alkyl, $C_{1-4}$ alkylNR5R6, $C_{1-4}$ alkylhetaryl, $OC_{1-4}$ alkyl, $OC_{2-4}$ alkyl$OC_{1-4}$alkyl, $OC_{1-4}$ alkylNR5R6, $OC_{1-4}$ alkylhetaryl, $OC_{1-4}$ alkylcyclohetalkyl, $SC_{1-4}$ alkyl, $SC_{2-4}$ alkyl$OC_{1-4}$ alkyl, $SC_{1-4}$ alkylNR5R6, NR5R6, NR5COR6, $NR5SO_2R6$; and R5 and R6 are each independently H, $C_{1-4}$ alkyl, or may be joined to form an optionally substituted 3-6 membered ring optionally containing an atom selected from O, S, NR7 and R7 is selected from H, $C_{1-4}$ allyl, aryl, hetaryl, $C_{1-4}$ alkylaryl, $C_{1-4}$ alkylhetaryl;

Z is selected from:

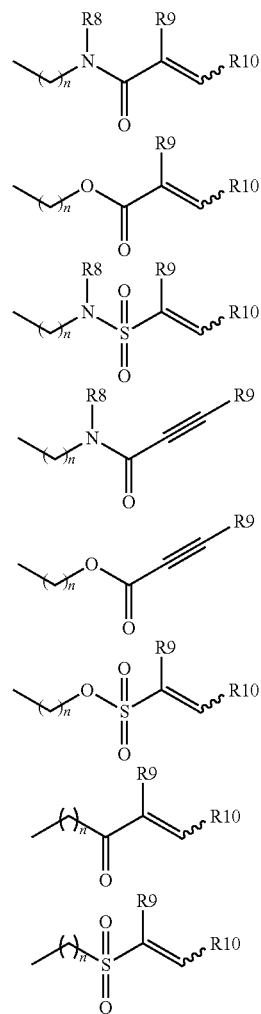

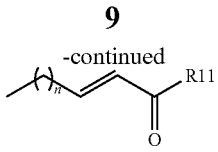

where R8 is selected from H, $C_{1-4}$ alkyl;

R9 and R10 are independently selected from H, $C_{1-4}$ alkyl, $C_{1-4}$alkylNR12R13, $C_{1-4}$ alkylOR12, $C_{1-4}$alkylhetaryl or may be joined to form a 5-8 membered ring optionally containing an atom selected from 0, 5, 50, $SO_2$, NR14;

R11 is selected from OH, $OC_{1-4}$ alkyl, NR12R13;

n is 0-4;

where R12 and R13 are independently selected from H, $C_{1-4}$ alkyl, or may be joined to form an optionally substituted 3-8 membered ring optionally containing an atom selected from O, S, NR14; and R14 is selected from H, $C_{1-4}$ alkyl.

In a second aspect the present invention consist in a composition comprising a carrier and at least one compound of the first aspect of the invention.

In a third aspect the present invention consists in a method of treating a tyrosine kinase-associated disease state, the method comprising administering a therapeutically effective amount of at least one compound of the first aspect of the invention or a therapeutically effective amount of a composition of the second aspect of the invention.

In a further aspect the present invention provides the use of the compounds of the first aspect or the compositions of the second aspect in the preparation of medicaments for the treatment of JAK3-associated disease states.

In a yet further aspect, the present invention provides for a method of suppressing the immune system of a subject, the method comprising administering a therapeutically effective amount of at least one compound of the first aspect of the invention or a therapeutically effective amount of a composition of the second aspect of the invention,

BRIEF DESCRIPTION OF THE FIGURES

FIG. 1 shows the amino acid sequence alignment of selected Jak Kinases (SEQ ID NOS:10-13).

DETAILED DESCRIPTION OF THE INVENTION

Figure 2:
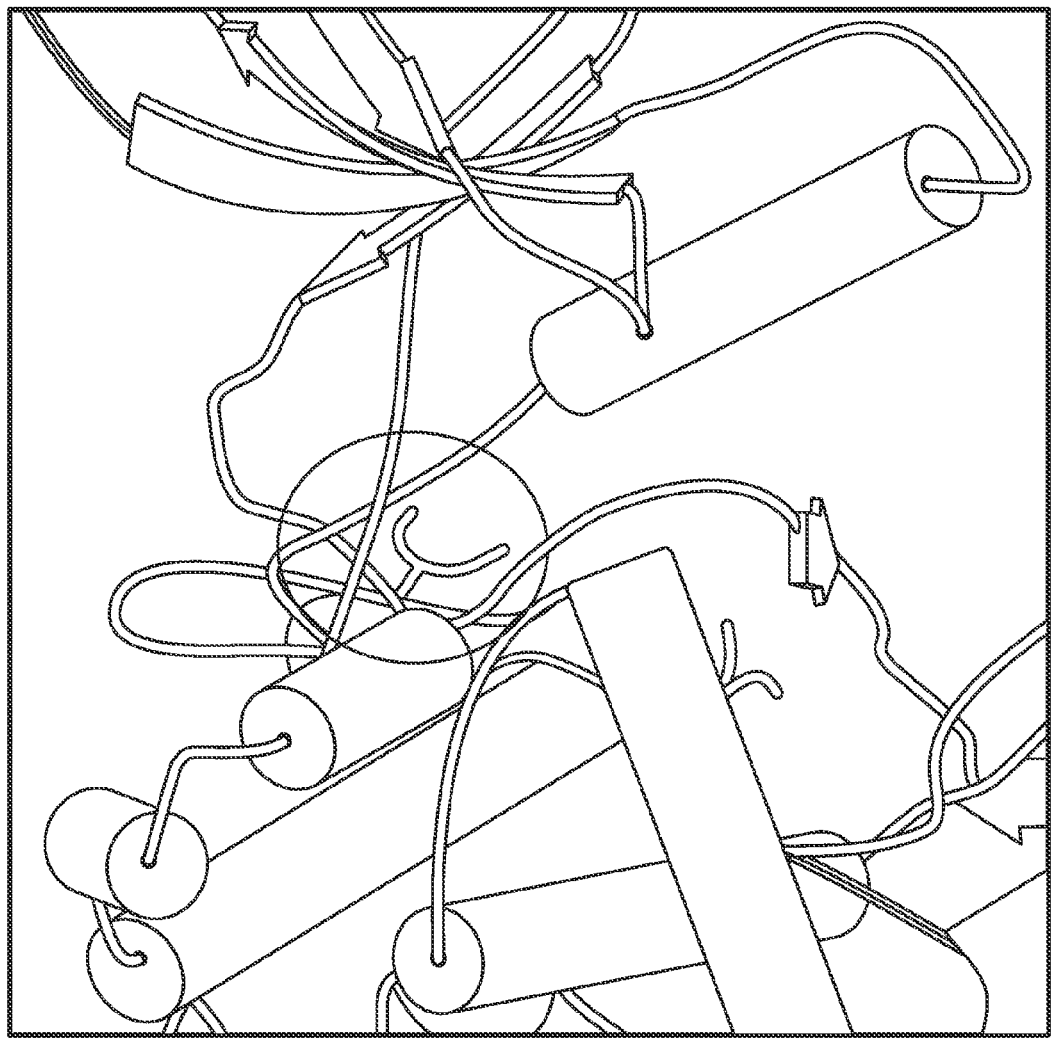
FIG. 2 shows a model of the Jak3 kinase ATP binding pocket displaying the Cysteine residue.

Accordingly, in a first aspect the present invention provides a compound of the general formula I

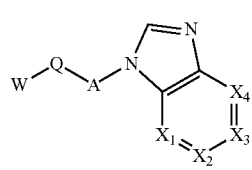

or pharmaceutically acceptable prodrugs, salts, hydrates, solvates, crystal forms or diastereomers thereof, wherein:

$X_1$, $X_2$, $X_3$, $X_4$ are each carbon where one is substituted with Z and the rest independently with Y; or one of $X_1$, $X_2$, $X_3$, $X_4$ is N, and the others are carbon where one carbon is substituted with Z and the rest independently with Y;

A is a ring selected from:

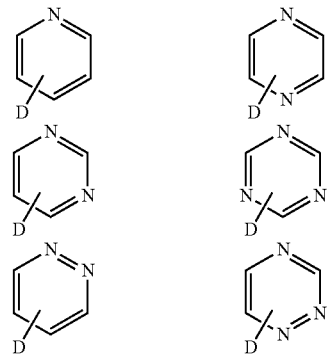

where D is selected from H, $C_{1-4}$ alkyl, halogen, amino;

Q is a bond, halogen, $C_{1-4}$ alkyl, O, S, SO, $SO_2$, CO, CS;

W is:

(i) NR1R2 where R1 and R2 are independently H, $C_{1-4}$ alkyl, $C_{1-4}$ alkylCF$_3$, aryl, hetaryl, $C_{1-4}$ alkylaryl, $C_{1-4}$ alkylhetaryl, $C_{3-8}$ cycloalkyl, $C_{2-6}$ alkenyl, cyclohetalkyl, $C_{1-4}$ alkylcycloalkyl, $C_{1-4}$ alkyl cyclohetalkyl, or R1 and R2 are joined to form an optionally substituted 3-8 membered ring optionally containing an atom selected from O, S, NR3; and R3 is selected from H, $C_{1-4}$ alkyl, aryl, hetaryl, $C_{1-4}$ alkyl aryl, $C_{1-4}$ alkyl hetaryl, COR4 where R4 is selected from H, $C_{1-4}$ alkyl, aryl, hetaryl;

OR (ii) H, $C_{1-4}$ alkyl, aryl, hetaryl, $C_{3-8}$ cycloalkyl, cyclohetalkyl, $C_{1-4}$ alkylaryl, $C_{1-4}$ alkylhetaryl, $C_{3-5}$ cycloalkyl, $C_{1-4}$ alkylcycloalkyl, $C_{1-4}$ alkyl cyclohetalkyl;

Y is H, halogen, CN, CF$_3$, nitro, OH, $C_{1-4}$ alkyl, $C_{1-4}$ alkylNR5R6, $C_{1-4}$ alkylhetaryl, $OC_{1-4}$ alkyl, $OC_{2-4}$ alkylOC$_{1-4}$alkyl, $OC_{1-4}$ alkylNR5R6, $OC_{1-4}$ alkylhetaryl, $OC_{1-4}$ alkylcyclohetalkyl, $SC_{1-4}$ alkyl, $SC_{2-4}$ alkylOC$_{1-4}$ alkyl, $SC_{1-4}$ alkylNR5R6, NR5R6, NR5COR6, NR5SO$_2$R6; and R5 and R6 are each independently H, $C_{1-4}$ alkyl, or may be joined to form an optionally substituted 3-6 membered ring optionally containing an atom selected from O, S, NR7 and R7 is selected from H, $C_{1-4}$ alkyl, aryl, hetaryl, $C_{1-4}$ alkylaryl, $C_{1-4}$ alkylhetaryl;

Z is selected from: done

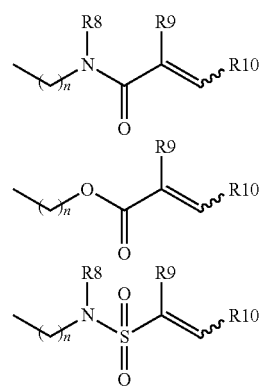

-continued

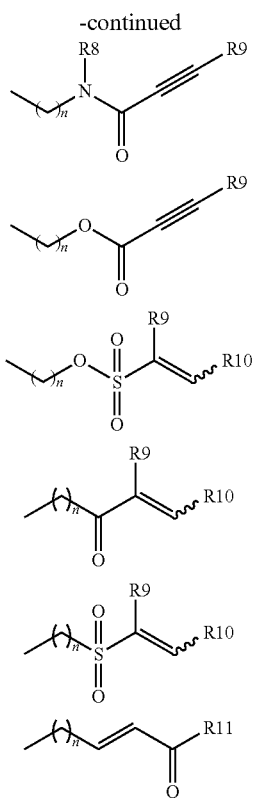

where R8 is selected from H, C$_{1-4}$ alkyl;

R9 and R10 are independently selected from H, C$_{1-4}$ alkyl, C$_{1-4}$ alkylNR12R13, C$_{1-4}$ alkylOR12, C$_{1-4}$ alkylhetaryl or may be joined to form a 5-8 membered ring optionally containing an atom selected from O, S, SO, SO$_2$, NR14;

R11 is selected from OH, OC$_{1-4}$ alkyl, NR12R13;

n is 0-4;

where R12 and R13 are independently selected from H, C$_{1-4}$ alkyl, or may be joined to form an optionally substituted 3-8 membered ring optionally containing an atom selected from O, S, NR14; and R14 is selected from H, C$_{1-4}$ alkyl.

In a preferred embodiment the compound is selected from compounds of the general formula II.

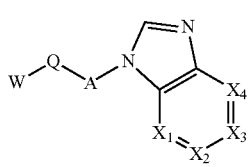

or pharmaceutically acceptable prodrugs, salts, hydrates, solvates, crystal forms or diastereomers thereof, wherein:

X$_1$, X$_2$, X$_3$, X$_4$ are each carbon where one is substituted with Z and the rest independently with Y; or one of X$_1$, X$_2$, X$_3$, X$_4$ is N, and the others are carbon where one carbon is substituted with Z and the rest independently with Y;

A is a ring selected from:

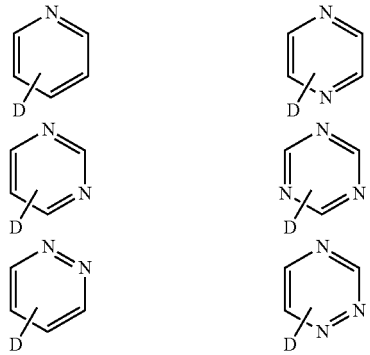

where D is selected from H, C$_{1-4}$ alkyl, halogen, amino;

Q is a bond, halogen, C$_{1-4}$ alkyl, O, S, SO, SO$_2$, CO, CS;

W is:
(i) NR1R2 where R1 and R2 are independently H, C$_{1-4}$ alkyl, C$_{1-4}$ alkylCF$_3$, aryl, hetaryl, C$_{1-4}$ alkylaryl, C$_{1-4}$ alkylhetaryl, C$_{3-8}$ cycloalkyl, C$_{2-6}$ alkenyl, cyclohetalkyl, C$_{1-4}$ alkylcycloalkyl, C$_{1-4}$ alkyl cyclohetalkyl, or R1 and R2 are joined to form an optionally substituted 3-8 membered ring optionally containing en atom selected from O, S, NR3; and R3 is selected from H, C$_{1-4}$ alkyl, aryl, hetaryl, C$_{1-4}$ alkyl aryl, C$_{1-4}$ alkyl hetaryl, COR4 where R4 is selected from H, C$_{1-4}$ alkyl, aryl, hetaryl;

OR (ii) W is H, C$_{1-4}$ alkyl, aryl, hetaryl, C$_{3-8}$ cycloalkyl, cyclohetalkyl, C$_{1-4}$ alkylaryl, C$_{1-4}$ alkylhetaryl, C$_{3-8}$ cycloalkyl, C$_{1-4}$ alkylcycloalkyl, C$_{1-4}$ alkyl cyclohetalkyl;

Y is H, halogen, CN, CF$_3$, nitro, OH, C$_{1-4}$ alkyl, C$_{1-4}$ alkylNR5R6, C$_{1-4}$ alkylhetaryl, OC$_{1-4}$ alkyl, OC$_{2-4}$ alkylOC$_{1-4}$ alkyl, OC$_{1-4}$ alkylNR5R6, OC$_{1-4}$ alkylhetaryl, OC$_{1-4}$ alkylcyclohetalkyl, SC$_{1-4}$ alkyl, SC$_{2-4}$ alkylOC$_{1-4}$ alkyl, SC$_{1-4}$ alkylNR5R6, NR5R6, NR5COR6, NR5SO$_2$R6; and R5 and R6 are each independently H, C$_{1-4}$ alkyl, or may be joined to form an optionally substituted 3-6 membered ring optionally containing an atom selected from O, S, NR7 and R7 is selected from H, C$_{1-4}$ alkyl, aryl, hetaryl, C$_{1-4}$ alkylaryl, C$_{1-4}$ alkylhetaryl;

Z is selected from:

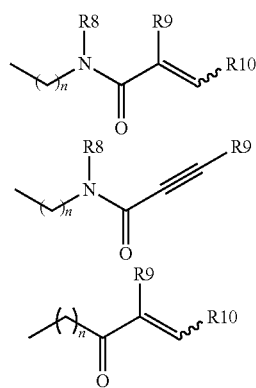

-continued

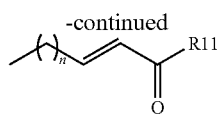

where R8 is selected from H, $C_{1-4}$ alkyl;
R9 and R10 are independently selected from H, $C_{1-4}$ alkyl, $C_{1-4}$ alkylNR12R13, $C_{1-4}$ alkylOR12, $C_{1-4}$ alkylhetaryl or may be joined to form a 5-8 membered ring optionally containing an atom selected from O, S, SO, $SO_2$, NR14;
R11 is selected from OH, $OC_{1-4}$ alkyl, NR12R13;
n is 0-4;
where: R12 and R13 are independently selected from H, $C_{1-4}$ allyl, or may be joined to form an optionally substituted 3-8 membered ring optionally containing an atom selected from O, S, NR14; and R14 is selected from H, $C_{1-4}$ alkyl.

In the above description it will be appreciated that:
$C_{1-4}$ alkyl means an unsubstituted or optionally substituted straight or branched alkyl chain.
Aryl means unsubstituted or optionally substituted phenyl or naphthyl.
Hetaryl means an unsubstituted or optionally substituted 5- or 6-membered heteroaromatic ring containing one or more heteroatoms selected from O, N, S.
Cycloalkyl means a 3-8 membered saturated ring.
Cyclohetalkyl means a 3-8 membered saturated ring containing 1.3 heteroatoms selected from O, S, NR15, where R15 is H, $C_{1-4}$ alkyl, aryl, hetaryl.
Substituents are chosen from halogen, $C_{1-4}$ alkyl, $CF_3$, CN, nitro, aryl, hetaryl, $OCF_3$, $OC_{1-4}$alkyl, $OC_{2-5}$ alkylNR16R17, Oaryl, Ohetaryl, $CO_2R16$, CONR16R17, nitro, NR16R17, NR16COR17, $NR16SO_2R17$; and R16, R17 are each independently H, $C_{1-4}$ alkyl, $C_{1-4}$ alkyl cycloalkyl, $C_{1-4}$ alkyl cyclohetalkyl, aryl, hetaryl, $C_{1-4}$alkyl aryl, $C_{1-4}$ alkyl hetaryl, or may be joined to form an optionally substituted 3-8 membered ring optionally containing an atom selected from O, S, NR18; and R18 is selected from H, $C_{1-4}$ alkyl, aryl, hetaryl, $C_{1-4}$ alkyl aryl, $C_{1-4}$ alkyl hetaryl.

The compounds of formula I may irreversibly inhibit JAK 3. Generally, the strength of binding of reversible inhibitors of an enzyme is measured by the $IC_{50}$ value which is a reflection of the equilibrium constant of the interaction between the inhibitor and the active site of the enzyme. Irreversible inhibitors display an apparent $IC_{50}$ because once the inhibitor is bound it will not leave the active site and the measured $IC_{50}$ will therefore improve (i.e. number will decrease) over time. For instance, the compound of example 20 exhibits an "$IC_{50}$" of ~40 nM after 20 minute incubation with enzyme (prior to addition of ATP) whereas the "IC50" drops to 7 nM after 90 min pre-incubation.

Preferably, the compound of formula I selectively inhibits JAK 3 with respect to JAK 1 or JAK 2. The term "selectively inhibits" is defined to mean that the apparent $IC_{50}$ of the compound for JAK 3 is more than ten-fold lower (i.e. more potent) than the $IC_{50}$ for JAK 1 or JAK 2.

The compounds of this invention include all conformational isomers (eg. cis and trans isomers). The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula I may also exist as tautomers. This invention relates to the use of all such tautomers and mixtures thereof.

This invention also encompasses pharmaceutical compositions containing prodrugs of compounds of the formula I. This invention also encompasses methods of treating or preventing disorders that can be treated or prevented by the inhibition of protein kinases, such as JAK comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (eg. two, three or four) amino acid residues which are covalently joined through peptide bonds to free amino, hydroxy and carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methioine sulfone. Prodrugs also include compounds wherein carbonates, carbamates, amides and alkyl esters which are covalently bonded to the above substituents of formula I through the carbonyl carbon prodrug sidechain. Prodrugs also include phosphate derivatives of compounds of formula I (such as adds, salts of acids, or esters) joined through a phosphorus-oxygen bond to a free hydroxyl of compounds of formula I.

Where the compound possesses a chiral centre the compound can be used as a purified isomer or as a mixture of any ratio of isomers. It is however preferred that the mixture comprises at least 70%, 80%, 90%, 95%, or 99% of the preferred isomer.

In a still further preferred embodiment the compound is selected from the compounds set out in the Examples. More preferably, the compound is selected from the compounds set out in Table 3.

In a second aspect the present invention consists in a composition comprising a carrier and at least one compound of the first aspect of the invention.

In a third aspect the present invention consists in a method of treating a tyrosine kinase-associated disease state, the method comprising administering a therapeutically effective amount of at least one compound of the first aspect of the invention or a therapeutically effective amount of a composition of the second aspect of the invention.

In a further preferred embodiment the disease state involves JAK1, JAK2, JAK3 or TYK2.

In a preferred embodiment of the present invention the disease state is selected from the group consisting of Atopy, such as Allergic Asthma, Atopic Dermatitis (Eczema), and Allergic Rhinitis; Cell Mediated Hypersensitivity, such as Allergic Contact Dermatitis and Hypersensitivity Pneumonitis; Rheumatic Diseases, such as Systemic Lupus Erythematosus (SLE), Rheumatoid Arthritis, Juvenile Arthritis, Sjögren's Syndrome, Scleroderma, Polymyositis, Ankylosing Spondylitis, Psoriatic Arthritis; Other autoimmune diseases such as Type I diabetes, autoimmune thyroid disorders, and Alzheimer's disease; Viral Diseases, such as Epstein Barr Virus (EBV), Hepatitis B, Hepatitis C, HIV, HTLV 1, Varicella-Zoster Virus (VZV), Human Papilloma Virus (HPV), Cancer, such as Leukemia, Lymphoma and Prostate Cancer.

As used herein the term "tyrosine kinase-associated disease state" refers to those disorders which result from aberrant tyrosine kinase activity, in particular JAK activity and/or which are alleviated by inhibition of one or more of these enzymes.

In a further aspect the present invention provides the use of the compounds described in the preparation of medicaments for the treatment of JAK3-associated disease states.

In a yet further aspect, the present invention provides for a method of suppressing the immune system of a subject, the method comprising administering a therapeutically effective amount of at least one compound of the first aspect of the invention or a therapeutically effective amount of a composition of the second aspect of the invention.

Preferably, the method of suppressing the immune system is for the treatment of disease states selected from lupus, multiple sclerosis, rheumatoid arthritis, psoriasis, Type I diabetes and complications from diabetes, cancer, asthma, atopic, dermatitis, autoimmune thyroid disorders, ulcerative colitis, Crohn's disease, and Alzheimer's disease.

Preferably, the method of suppressing the immune system is to modify the immune system response to a transplant into a subject. More preferably, the transplant is an organ transplant or tissue transplant.

The present invention provides pharmaceutical compositions comprising at least one of the compounds of the formula I or II capable of treating a JAK3-associated disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I or II may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

In addition to primates, such as humans, a variety of other mammals can be treated according to the method of the present invention. For instance, mammals including, but not limited to, cows, sheep, goats, horses, dogs, cats, guinea pip, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

The subjects treated in the above methods, in whom which JAK3 inhibition is desired, are mammals, including, but not limited to, cows, sheep, goats, horses, dogs, cats, guinea pigs, rats or other bovine, ovine, equine, canine, feline, rodent or murine species, and preferably a human being, male or female.

The term "therapeutically effective amount" means the amount of the subject composition that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic add or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolisable lipid capable of forming liposomes can be used. The present compositions in liposome form can contain, in addition to a compound of the present invention, stabilisers, preservatives, excipients and the like. The preferred lipids are the phospholipids and phosphatidyl choline, both natural and synthetic. Methods to form liposomes are known in the art.

The pharmaceutical composition and method of the present invention may further comprise other therapeutically active compounds as noted herein which are usually applied in the treatment of the above mentioned pathological conditions. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Examples of other therapeutic agents include the following:

cyclosporins (e.g., cyclosporin A), CTLA4-Ig, antibodies such as ICAM-3, anti-IL-2 receptor (Anti-Tac), anti-CD45RB, anti-CD2, anti-CD3 (OKT-3), anti-CD4, anti-CD80, anti-CD86, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), cholesterol biosynthesis inhibitors such as HMG CoA reductase inhibitors (lovastatin and simvastatin), non-steroidal antiinflammatory drugs (NSAIDs) such as ibuprofen, aspirin, acetaminophen, leflunomide, deoxyspergualin, azathioprine and cyclooxygenase inhibitors such as rofecoxib and celecoxib, steroids such as prednisolone or dexamethasone, gold compounds, antiproliferative agents such as methotrexate, FK506 (tacrolimus, Prograf), mycophenolate mofetil, cytotoxic drugs such as azathioprine, VP-16, etoposide, fludarabine, cisplatin and cyclophosphamide, TNF-α inhibitors such as tenidap, anti-TNF antibodies or soluble TNF receptor, and rapamycin (sirolimus or Rapamune) or derivatives thereof.

When other therapeutic agents are employed in combination with the compounds of the present invention they may be used for example in amounts as noted in the Physician Desk Reference (PDR) or as otherwise determined by one of ordinary skill in the art.

In the treatment or prevention of conditions which require protein tyrosine kinase inhibition an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In order that the nature of the present invention may be more clearly understood, preferred forms thereof will now be described with reference to the following non-limiting examples.

EXAMPLES

Materials and Methods

Compound Synthesis

Compounds of the general formula I are generally prepared from dihaloheterocycle.

When Q is a bond and W is amino, the synthesis may begin with a nucleophilic aromatic substitution to generate a monoamino-monohalo intermediate.

The nucleophilic aromatic substitution is typically carried out by addition of an amine to the di-halogenated heterocycle in a solvent such as ethanol, isopropanol, tert-butanol, dioxane, THF, DMF, toluene or xylene. The reaction is typically performed at elevated temperature in the presence of excess amine or a non-nucleophilic base such as triethylamine or diisopropylethylamine, or an inorganic base such as potassium carbonate or sodium carbonate.

Alternatively, the amino substituent may be introduced through a transition metal catalysed amination reaction. Typical catalysts for such transformations include Pd(OAc)$_2$/P(t-Bu)$_3$, Pd$_2$(dba)$_3$/BINAP and Pd(OAc)$_2$/BINAP. These reactions are typically out in solvents such as toluene or dioxane, in the presence of bases such as caesium carbonate or sodium or potassium tert-butoxide at temperatures ranging from room temperature to reflux.

The amines employed in the first step of the synthesis of these compounds are obtained commercially or are prepared using methods well known to those skilled in the art.

When Q is a bond and W is aryl, hetaryl or other similar carbon-linked systems, the synthesis typically begins with a cross-coupling reaction between dihaloheterocycle and a suitably functionalised coupling partner. Typical coupling partners are boronic acids or esters (Suzuki coupling: see for example Miyaura and Suzuki 1995), stannanes (Stille coupling: see for example Stille 1986), Grignard reagents (Kumada coupling: Kumada, Tamao and Sumitani 1988) or organozinc species (Negishi coupling: Negishi 2002). The Suzuki coupling is the preferred coupling method and is typically performed in a solvent such as DMF, THF, DMF, ethanol, propanol, toluene, or 1,4-dioxane in the presence of a base such as potassium carbonate, lithium hydroxide, caesium carbonate, sodium hydroxide, potassium fluoride or potassium phosphate. The reaction may be carried out at elevated temperatures and the palladium catalyst employed may be selected from Pd(PPh$_3$)$_4$, Pd(OAc)$_2$, [PdCl$_2$(dppf)], Pd$_2$(dba)$_3$/P(t-Bu)$_3$.

Where Q is CO, the synthesis begins with the requisite hetaryl carboxylic add bearing a halo group. Amide derivatives of the acid may be readily formed by coupling an amine with the acid using coupling reagents such as dicyclohexylcarbodiimide, 1-(3-dimethylaminopropyl)-3-ethylcarbodiimide, diisopropylcarbodiimide or carbonyldiimidazole in solvents such as dichloromethane, tetrahydrofuran or 1,4-dioxane. Alternatively, the acid can be converted to the respective add chloride using thionyl chloride, oxalyl chloride, bis(trichloromethyl)carbonate or cyanuric chloride, or to the mixed anhydride species using, for example, t-butyl chloroformate, using procedures well known to those skilled in the art. The acid chloride or mixed anhydride derivatives can then be reacted with the desired amine preferably in the presence of a base such as triethylamine, diisopropylethylamine or solid phase equivalent in a solvent such as dichloromethane, tetrahydrofuran, dioxane or ethyl acetate at ambient or elevated temperatures, to generate the amide. The acid chloride may also react with the required amine under aqueous conditions preferably in the presence of art inorganic base such as sodium hydroxide, potassium hydroxide or sodium carbonate to generate the desired amide.

Thioamides may be prepared from the amides formed above by methods well-known to those skilled in the art and include reaction of the amide with Lawesson's reagent in a solvent such as toluene at elevated temperature.

The second step of the synthesis involves a nucleophilic aromatic substitution reaction of the monohalo intermediate with a benzimidazole or azabenzimidazole. The reaction is typically performed using a salt of the benzimidazole or azabenzimidazole in solvents such as THF, DMF, DMA, NMP, toluene, or xylene from room temperature to reflux. The benzimidazole or azabenzimidazole salt is prepared by reaction with a metal hydride such as sodium or potassium hydride or by reaction with caesium carbonate. Alternatively, a metal-catalysed coupling reaction can be used to introduce the benzimidazole or azabenzimidazole ring. Typical metal catalysts include Pd(OAc)$_2$/dppf, PdCl$_2$/dppe, Pd$_2$(OAc)$_2$/P(t-Bu)$_3$, (CuOTf)$_2$.PhH. The reaction is typically performed Using a base such as caesium carbonate, rubidium carbonate, potassium carbonate, sodium tert-butoxide or potassium phosphate in a solvent such as xylene, toluene, or DMF from room temperature to reflux. Auxiliary reagents such as phase transfer agents (e.g. cetrimonium bromide) or copper complexing agents (e.g. phenanthroline) may also be employed in the reaction.

Alternatively, the reaction sequence outlined above may be reversed beginning with coupling of the benzimidazole or azabenzimidazole to the dihaloheterocycle using the methods outlined above, followed by introduction of the second substituent onto the heterocyclic nucleus using the procedures outlined above.

An alternative route to compounds of the general formula I involves a copper mediated reaction between a benzimidazole or azabenzimidazole and an organometallic reagent (see for example Finet, 2002). Preferable organometallic reagents are boronic acids.

The thiol reactive moiety (depicted as part of the substituents Z) present in compounds of the general formula I of the invention may be already present in the functionalities employed in the synthetic processes described above or may be introduced at the final stage of the synthetic procedure. For example, the thiol reactive moiety may be introduced in compounds bearing a free hydroxyl or amino substituent by coupling with a suitable acid. This is typically achieved using coupling reagents such as dicyclohexylcarbodiimide, 1-(3-dimethylaminopropyl)-3-ethylcarbodiimide, diisopropylcarbodiimide or carbonyldiimidazole in solvents such as dichloromethane, tetrahydrofuran or 1,4-dioxane. Alternatively, suitable mixed anhydride species of the acid, funned using, for example, t-butyl chloroformate, using procedures well known to those skilled in the art, or a suitable acid chloride derivative, can be reacted with the amine or alcohol moiety in the presence of a base such as triethylamine, diisopropylethylamine or solid phase equivalent in a solvent such as dichloromethane, tetrahydrofuran, dioxane or ethyl acetate at ambient or elevated temperatures, to generate the desired compound.

Those skilled in the art will appreciate that the order of the reactions described for the syntheses above may be changed in certain circumstances and that certain functionalities may need to be derivatised (i.e. protected) in certain instances for the reactions described above to proceed with reasonable yield and efficiency. The types of protecting functionality are well-known to those skilled in the art and are described for example in Greene (Greene, 1999). The products formed from the reaction sequences described above may be further derivatised using techniques well known to those skilled in the art.

Representative syntheses are reported below.

Example 1

6-Chloro-N-[(1R)-1-phenylethyl]pyrazin-2-amine

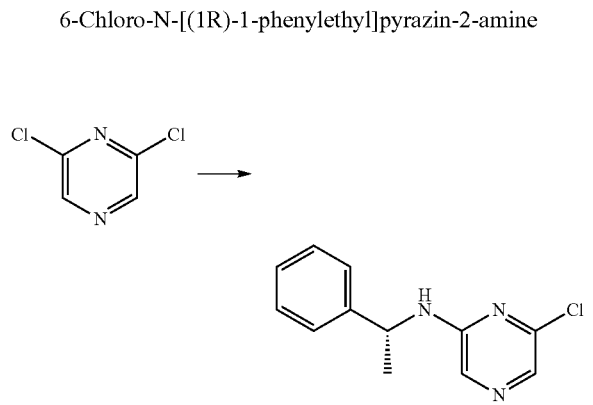

A solution of R-α-methylbenzylamine (0.57 g, 4.7 mmol) and 2,6-dichloropyrazine (0.6388 g, 4.29 mmol) in dioxane (2.5 mL) was heated at reflux under $N_2$ for 48 hours. The solvent was removed and the product crystallised from toluene-hexane (0.82 g, 82%).

$^1$H-n.m.r. (CDCl$_3$) δ 1.58 (d, J=6.6 Hz, 3H, CH$_3$), 4.88 (m, 1H, CH), 5.07 (d, 1H, NH), 7.24-7.36 (m, 5H, Ar—H), 7.61 (s, 1H, pyraz-H), 7.79 (s, 1H, pyraz-H).

Example 2

N-(tert-butyl)-6-chloropyrazin-2-amine

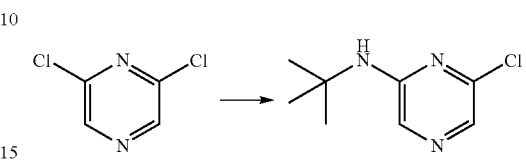

A mixture of tert-butylamine (14.9 g, 20 mmol), 2,6-dichloropyrazine (6.0 g, 40 mmol), Hünig's base (10 mL) and ethoxyethanol (6 mL) was heated at 130° C. in a sealed tube for 18 hours. The solvent was removed in vacuo and the residue taken up in CH$_2$Cl$_2$ (100 mL) and filtered. The filtrate was washed with H$_2$O (2×20 mL), brine (20 mL) and dried (Na$_2$SO$_4$). Chromatography eluting with CH$_2$Cl$_2$ separated the product as a white solid (5.4 g, 72%).

$^1$H-n.m.r. (CDCl$_3$) δ1.44 (s, 9H, CH$_3$), 4.68 (br s, 1H, NH), 7.71 (s, 1H, pyraz-H), 7.72 (s, 1H, pyraz-H).

Example 3

6-Chloro-N-[(1R)-1-(3-methoxyphenyl)ethyl]pyrazin-2-amine

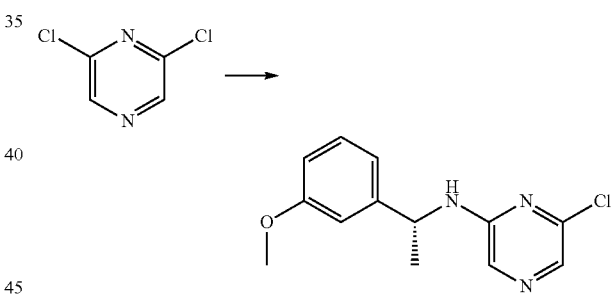

In a procedure analogous to Example 1, reaction of R-α-methylbenzylamine (1.0 g, 6.6 mmol) and 2,6-dichloropyrazine (0.440 g, 2.95 mmol) furnished the product (517 mg, 67%).

$^1$H-n.m.r. (CDCl$_3$) δ 1.59 (d, J=6.9 Hz, 3H, CH$_3$), 3.81 (s, 3H, OCH$_3$), 4.87 (m, 1H, CH), 5.47 (br s, 1H, NH), 6.79-7.30 (m, 4H, Ar—H), 7.66 (s, 1H, pyraz-H), 7.79 (s, 1H, pyraz-H).

Example 4

6-Chloro-N-phenylpyrazin-2-amine

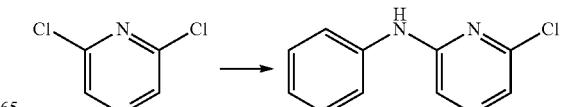

A solution of 2,6-dichloropyrazine (1 g, 62 mmol) and aniline (1.25 g, 13.4 mmol) in ethoxyethanol (20 mL) containing DIPEA (2.5 mL, 13.4 mmol) was heated at reflux for 3 days under N₂. The solution was concentrated under reduced pressure and the residue dissolved in EtOAc (50 mL) and washed successively with H₂O (50 mL), 1M HCl (2×50 mL), H₂O (50 mL) and brine (50 mL). After drying (Na₂SO₄) the solvent was removed under reduced pressure and the residue chromatographed eluting with EtOAc-hexane (20: 80-50:50) to separate pure product from the lower fractions (230 mg, 17%).

¹H-n.m.r. (CDCl₃) δ 6.62 (br s, 1H, NH), 7.11-7.20 (m, 1H, ArH), 7.38 (br s, 2H, ArH), 7.40 (s, 2H, ArH), 7.98 (s, 1H, pyraz-H), 8.11 (s, 1H, pyraz-H).

Example 5

6-Chloro-N-[(1R)-1-(4-methylphenyl)ethyl]pyrazin-2-amine

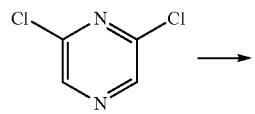

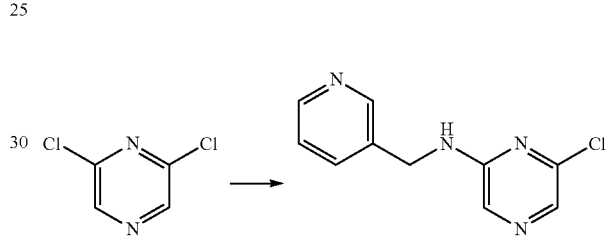

In a procedure analogous to Example 1, reaction of α-(R)-4-dimethylbenzylamine (250 mg, 1.85 mmol) and 2,6-dichloropyrazine (0.251 g, 1.67 mmol) furnished the product (199.5 mg, 48%).

¹H-n.m.r. (CDCl₃) δ 1.56 (d, 3H, J=6.9 Hz, CH₃), 2.33 (s, 3H, CH₃), 4.84 (m, 1H, CH), 5.05 (br s, 1H, NH), 7.15 (AA'XX', 2H, Ar—H), 7.24 (AA'XX', 2H, Ar—H), 7.60 (s, 1H, pyraz-H), 7.78 (s, 1H, pyraz-H).

Example 6

6-Chloro-N-(4-morpholin-4-ylphenyl)pyrazin-2-amine

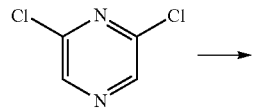

In a procedure analogous to Example 1, reaction of 4-morpholinoaniline (2.15 g, 12.1 mmol) and 2,6-dichloropyrazine (0.756 g, 5.03 mmol) furnished the product (0.54 g, 37%).

¹H-n.m.r. (CDCl₃) δ 3.25 (br s, 4H, CH₂), 3.99 (br s, 4H, CH₂), 7.05-7.17 (m, 2H, ArH), 7.42-7.54 (m, 2H, ArH), 7.94 (s, 1H, pyraz-H), 8.04 (s, 1H, pyraz-H), 8.06 (s, NH).

Example 7

6-Chloro-N-(2-furylmethyl)pyrazin-2-amine

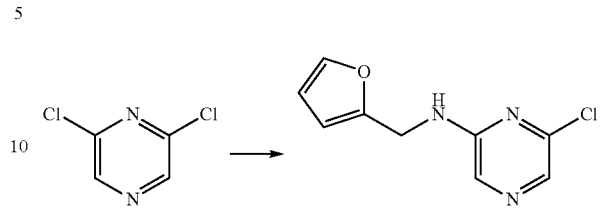

In a procedure analogous to Example 1, reaction of furfurylamine and 2,6-dichloropyrazine furnished the product (98%).

¹H-n.m.r. (CDCl₃) δ 4.57 (d, J=5.7 Hz, 2H, NCH₂), 5.01 (s, broad, 1H, NH), 6.30 (d, J=3.3 Hz, 1H, furanyl-H), 6.35-6.33 (m, 2H, furanyl-H), 7.81 (s, 1H, pyraz.-H), 7.84 (s, 1H, pyraz.-H).

Example 8

6-Chloro-N-(pyridin-3-ylmethyl)pyrazin-2-amine

A mixture 2,6-dichloropyrazine (0.671 mmol) and 3-picolylamine (2.014 mmol) in xylene (25 ml) was refluxed overnight. The residue obtained after evaporation of the solvent was suspended between CH₂Cl₂ (100 ml) and water (100 ml). The organic layer was separated and the aqueous layer was extracted with CH₂Cl₃ (3×50 ml). The combined organic extracts were washed with brine (1×100 ml), dried (Na₂SO₄) and the solvent removed in vacuo. The residue was then purified by column chromatography eluting with a hexane: ethyl acetate gradient mixture to afford the desired product (93%).

¹H-n.m.r. (CDCl₃) δ4.61 (d, J=5.7 Hz, 2H, NCH₂), 5.29 (s, broad, 1H, NH), 7.27 (m, 1H, pyrid.-H), 7.30 (m, 1H, pyrid.-H), 7.71 (d, J=7.8 Hz, 1H, pyrid.-H), 7.85 (s, 1H, pyrid.-H), 8.54 (s, broad, 1H, pyraz.-H), 8.61 (s, broad, 1H, pyraz.-H).

Example 9

N-Benzyl-6-chloro-N-methylpyrazin-2-amine

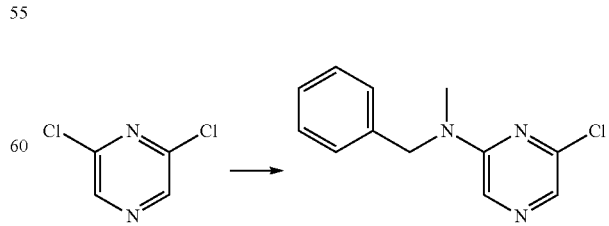

In a procedure analogous to Example 1, reaction of N-methyl benzylamine and 2,6-dichloropyrazine furnished the product (70%).

¹H-n.m.r. (CDCl₃) δ3.11 (s, 3H, NCH₃), 4.78 (s, 2H, ArCH₂N), 7.24 (d, J=6.9 Hz, 2H, ArH), 7.37-7.28 (m, 4H, ArH), 7.81 (s, 1H, pyraz.-H), 7.88 (s, 1H, pyraz.-H).

Example 10

1H-Benzimidazol-5-amine

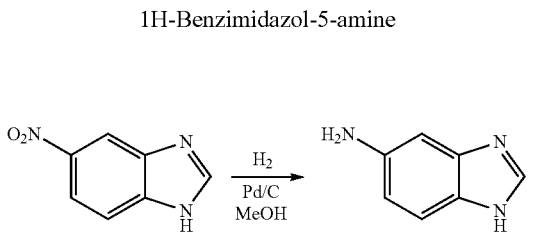

A solution of 5-nitrobenzimidazole (10.0 g, 613 mmol) in methanol (250 mL) was hydrogenated in the presence of 10% Pd/C (0.40 g) at atmospheric pressure for 20 h. The mixture was filtered through Celite® and the solvent removed under reduced pressure to afford the pure product (8.1 g, 100%).

¹H-n.m.r. (CD₃OD) δ 6.75 (dd, 1H, J=8.4 and 2.0 Hz, benzimid-H), 6.92 (d, 2.0 Hz, benzimid-H), 7.36 (d, 1H, J=8.4 Hz, benzimid-H), 7.92 (s, 1H, benzimid-H).

Example 11

1-[6-(tert-Butylamino)pyrazin-2-yl]-1H-benzimidazol-5-amine and 1-[6-(tert-butylamino)pyrazin-2-yl]-1H-benzimidazol-6-amine

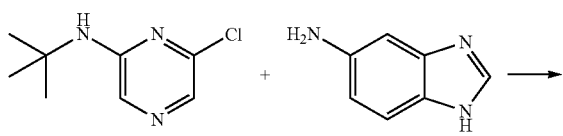

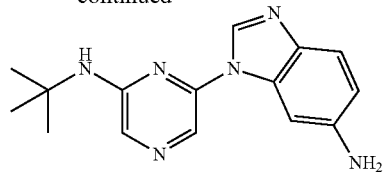

+

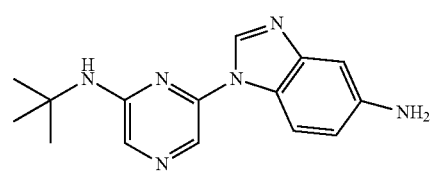

A mixture of 1H-benzimidazol-5-amine (2.93 g, 22 mmol), N-(tert-butyl)-6-chloropyrazin-2-amine (3.71 g, 20=not) and cesium carbonate (9.12 g, 28 mmol) in DMF (20 mL) was heated under N₂ for 48 h. Upon cooling to RT the mixture was filtered and the filtrate concentrated in vacuo. The residue was extracted with CHCl₃ and the solvent removed under reduced pressure. The residue was chromatographed using CH₂Cl₂-MeOH (98:2-93:7) to give from the less polar fractions 1-[6-(tert-butylamino)pyrazin-2-yl]-1H-benzimidazol-6-amine (1.38 g):

¹H-n.m.r. (CDCl₃) δ 1.51 (s, 9H, C(CH₃)₃), 3.80 (br s, 2H, NH₂), 4.84 (br s, 1H, NH), 6.74 (dd, 1H, J=8.4, 2.2 Hz, benzimid-H), 7.21 (d, 1H, J=2.0 Hz, benzimid-H), 7.62 (d, 1H, J=9.2 Hz, benzimid-H), 7.79 (s, 1H, pyraz-H), 8.07 (s, 1H; pyraz-H), 8.17 (s, 1H, benzimid-H).

and from the more polar fractions 1-[6-(tert-butylamino)pyrazin-2-yl]-1H-benzimidazol-5-amine (1.54 g):

¹H-n.m.r. (CDCl₃) δ1.51 (s, 9H, C(CH₃)₃), 3.48 (br s, 2H, NH₂), 4.86 (s, 1H, NH), 6.79 (dd, 1H, J=8.6, 2.2 Hz, benzimid-H), 7.14 (d, 1H, J=2.0 Hz, benzimid-H), 7.70 (d, 1H, J=8.6 Hz, benzimid-H), 7.78 (s, 1H, pyraz-H), 8.07 (s, 1H, pyraz-H), 8.47 (s, 1H, benzimid-H).

Example 12

1-(6-{[(1S)-1-Phenylethyl]amino}pyrazin-2-yl)-1H-benzimidazol-5-amine and 1-(6-{[(1S)-1-phenylethyl]amino}pyrazin-2-yl)-1H-benzimidazol-6-amine

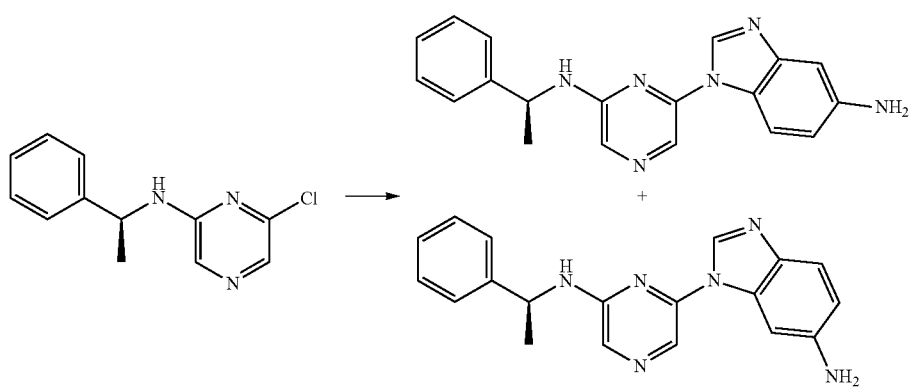

To a stirred solution of 5-amino-benzimidazole (290 mg, 2.2 mmol) in anhydrous DMF (10 mL) under $N_2$ was added caesium carbonate (980 mg) The resulting mixture was stirred at 70° C. for 60 min. To this was added a solution of 6-chloro-N-[(1S)-1-phenylethyl]pyrazin-2-amine (470 mg) in DMF (5 mL) and the resulting mixture was then heated at reflux for 48 h. The DMF was removed under reduced pressure and the residue diluted with chloroform. The organic layer was washed with aqueous $Na_2CO_3$, dried ($Na_2SO_4$) and the solvent removed under reduced pressure to furnish the crude product. Column chromatography using dichloromethane-methanol (95:5-92:8) as eluant separated two fractions from unreacted starting material. The higher Rf fraction was assigned as the 6-isomer (276 mg, 42%).

$^1$H-n.m.r. ($CDCl_3$) δ1.64 (d, 3H, f=6.9 Hz, $CH_3$), 2.90 (br s, 2H, $NH_2$), 5.05 (m, 1H, CH), 5.21 (d, 1H, NH), 6.70 (dd, 1H, J=8.7, 2.1 Hz, benzimid-H), 6.97 (d, 1H, J=1.8 Hz, benzimid-H), 7.28-7.43 (m, 5H, Ph-H), 7.58 (d, 1H, J=8.4 Hz, benzimid-H), 7.84 (s, 1H, pyraz-H), 8.08 (s, 1H, pyraz-H), 8.21 (s, 1H, benzimid-H). m/z (ES) 331 ($M^++H$).

The lower fraction was assigned as the 5-isomer (170 mg, 26%), $^1$H-n.m.r. ($CDCl_3$) δ1.64 (d, 3H, J=6.9 Hz, $CH_3$), 2.85 (br s, 2H, $NH_2$), 5.01 (m, 1H, CH), 5.19 (d, 1H, NH), 6.70 (dd, 1H, J=8.7, 2.1 Hz, benzimid-H), 7.11 (d, 1H, J=1.8 Hz, benzimid-H), 7.29-7.40 (m, 5H, Ph-H), 7.51 (d, 1H, J=8.7 Hz, benzimid-H), 7.81 (s, 1H, pyraz-H), 8.10 (s, 1H, pyraz-H), 832 (s, 1H, benzimid-H).

m/z (ES) 331 ($M^++H$).

Example 13

1-(6-(Chloropyrazin-2-yl)-1H-benzimidazol-5-amine and 1-(6-(Chloropyrazin-2-yl)-1H-benzimidazol-6-amine

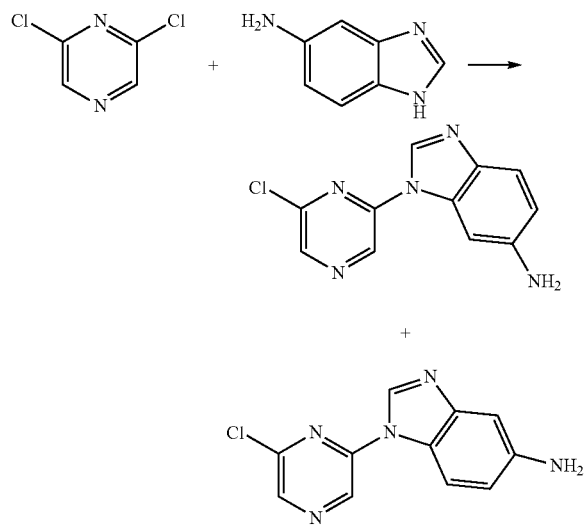

A mixture of 1H-benzimidazol-5-amine (0.8 g, 6 mmol), 2,6-dichloropyrazine (0.9 g, 6.0 mmol) and cesium carbonate (2.73 g, 8.4 mmol) in DMF (6 mL) was heated under $N_2$ for 6 h. Upon cooling to RT the mixture was diluted with dichloromethane-methanol (6:1, 30 mL) and filtered and the filtrate concentrated in vacuo. The residue was chromatographed using $CH_2Cl_2$-MeOH (98:2-94:6) to give from the less polar fractions 1-(6-chloropyrazin-2-yl)-1H-benzimidazol-6-amine (398 mg):

$^1$H-n.m.r. ($CDCl_3$) δ 6.74 (dd, 1H, J=8.2, 2.2 Hz, benzimid-H), 7.40 (d, 1H, J=2.2 Hz, benzimid-H), 7.51 (d, 1H, J=8.2 Hz, benzimid-H), 8.40 (s, 1H, pyraz-H), 8.48 (s, 1H, pyraz-H), 8.83 (s, 1H, benzimid-H).

and from the more polar fractions 1-(6-chloropyrazin-2-yl)-1H-benzimidazol-5-amine (435 mg)

$^1$H-n.m.r. ($CDCl_3$) δ6.79 (dd, 1H, J=8.8, 2.2 Hz, benzimid-H), 7.03 (d, 1H, J=2.2 Hz, benzimid-H), 7.86 (d, 1H, J=9.0 Hz, benzimid-H), 8.44 (s, 1H, pyraz-H), 8.52 (s, 1H, pyraz-H), 8.82 (s, 1H, benzimid-H).

Example 14

1-{6-[(Cyclopropylmethyl)amino]pyrazin-2-yl}-1H-benzimidazol-6-amine

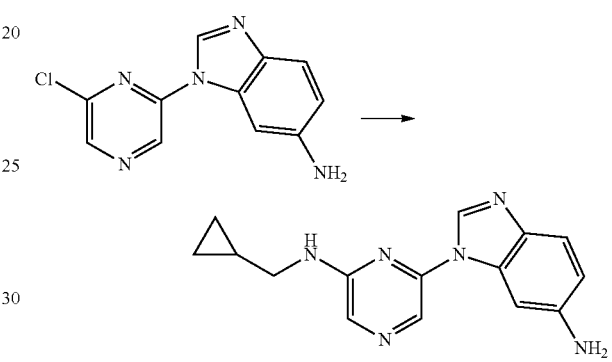

A solution of 1-(6-chloropyrazin-2-yl)-1H-benzimidazol-6-amine (100 mg, 0.41 mmol) and cyclopropylmethylamine (424 μL, 4.1 mmol) in ethoxyethanol (2 mL) containing DIPEA (140 μL) was heated at reflux overnight under $N_2$. The solution was concentrated under reduced pressure and the residue dissolved in EtOAc (20 mL) and washed successively with $H_2O$ (20 mL), 1M HCl (2×20 mL), $H_2O$ (20 mL) and brine (20 mL). After drying ($Na_2SO_4$) the solvent was removed under reduced pressure and the residue chromatographed eluting with dichloromethane-methanol (9:1-94:6) to separate pure product from the lower fractions (98 mg)

$^1$H-n.m.r. ($CDCl_3$) δ0.28-0.36 (m, 2H, $CH_2$), 0.57-0.66 (m, 2H, $CH_2$), 1.08-1.22 (m, 1H, CH), 3.27-3.34 (m, 2H, $CH_2$), 3.79 (br s, 2H, $NH_2$), 5.02 (m, 1H, NH), 6.74 (dd, 1H, J=8.6, 2.2 Hz, benzimid-H), 7.33 (d, 1H, J=2.2 Hz, benzimid-H), 7.61 (d, 1H, J=9.2 Hz, benzimid-H), 7.84 (s, 1H, pyraz-H), 8.10 (s, 1H, pyraz-H), 8.35 (s, 1H, benzimid-H).

Example 15

1-[6-(Isopropylamino)pyrazin-2-yl]-1H-benzimidazol-6-amine

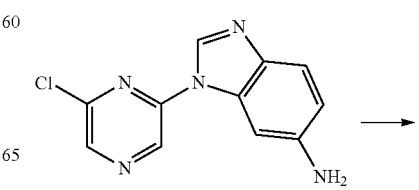

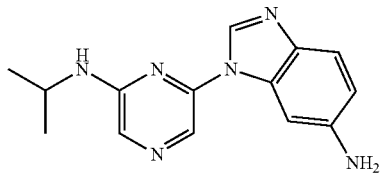

A solution of 1-(6-chloropyrazin-2-yl)-1H-benzimidazol-6-amine (100 mg, 0.41 mmol) and isopropylamine (350 μL, 4.1 mmol) in ethoxyethanol (2 mL) containing DIPEA (140 μL) was heated in a sealed tube overnight under $N_2$. The solution was concentrated under reduced pressure and the residue dissolved in EtOAc (20 mL) and washed successively with $H_2O$ (20 mL) and brine (20 mL). After drying ($Na_2SO_4$) the solvent was removed under reduced pressure and the residue chromatographed eluting with dichloromethane-methanol (9:1-94:6) to separate pure product from the lower fractions (102 mg).

$^1$H-n.m.r. (CDCl$_3$) δ1.33 (d, 6H, J=6.4 Hz, CH$_3$), 3.79 (br s, 2H, NH$_2$), 4.05-4.21 (m, 1H, CH), 4.72 (m, 1H, J=7.2 Hz, NH), 6.75 (dd, 1H, J=8.6, 2.2 Hz, benzimid-H), 7.32 (d, 1H, J=2.0 Hz, benzimid-H), 7.61 (d, J=8.4 Hz, benzimid-H), 7.79 (s, 1H, pyraz-H), 8.09 (s, 1H, pyraz-H), 8.35 (s, 1H, benzimid-H).

Example 16

1-[6-(Diethylamino)pyrazin-2-yl]-1H-benzimidazol-6-amine

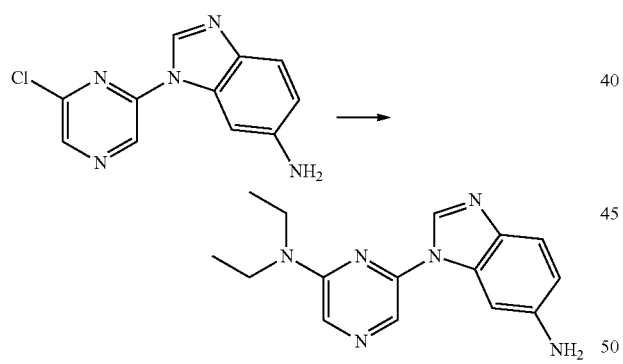

A solution of 1-(6-chloropyrazin-2-yl)-1H-benzimidazol-6-amine (100 mg, 0.41 mmol) and diethylamine (430 μL, 4.1 mmol) in ethoxyethanol (2 mL) containing DIPEA (140 μL) was heated in a sealed tube overnight under $N_2$. The solution was concentrated under reduced pressure and the residue dissolved in EtOAc (20 mL) and washed successively with $H_2O$ (20 mL) and brine (20 mL). After drying ($Na_2SO_4$) the solvent was removed under reduced pressure and the residue chromatographed eluting with dichloromethane-methanol (9:1-94:6) to separate pure product from the lower fractions (110 mg).

$^1$H-n.m.r. (CDCl$_3$) δ1.28 (t, 6H, J=7.1 Hz, CH$_3$), 3.61 (q, 4H, J=7.1 Hz, CH$_2$), 3.78 (br s, 2H, NH$_2$), 6.74 (dd, 1H, J=8.6, 2.2 Hz, benzimid-H), 7.32 (d, 1H, J=2.4 Hz, benzimid-H), 7.61 (d, 1H, J=8.8 Hz, benzimid-H), 7.91 (s, 1H, pyraz-H), 8.06 (s, 1H, pyraz-H), 8.36 (s, benzimid-H).

Example 17

1-(6-Pyridin-4-ylpyrazin-2-yl)-1H-benzimidazol-6-amine

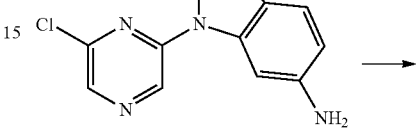

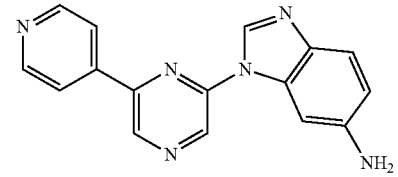

Under a nitrogen atmosphere a mixture of 1-(6-chloropyrazin-2-yl)-1H-benzimidazol-6-amine (50 mg, 0.20 mmol), 4-pyridylboronic add (30 mg, 0.24 mmol), tetrakis(triphenylphosphine)palladium(0) (23 mg, 0.02 mmol) in toluene-n-propanol (2 mL, 3:1) was treated with 2M aqueous sodium carbonate solution (0.14 mL, 0.84 mmol). The resulting mixture was stirred vigorously whilst being heated under reflux overnight. Upon cooling, the mixture was diluted with ethyl acetate (10 mL) and washed with $H_2O$ (1×10 mL). The aqueous phase was extracted with ethyl acetate (10 mL) and the organic layers combined and washed with 0.5M $Na_2CO_3$, brine and then dried ($Na_2SO_4$). Removal of solvent fit vacuo then yielded crude product, which was purified by column chromatography using dichloromethane-methanol (98:2-91:9) as eluent to furnish the product (32 mg).

$^1$H-n.m.r. (CDCl$_3$) δ 3.88 (s, broad, 2H, NH$^2$), 6.80 (dd, 1H, J=8.6 and 2.0 Hz, benzimid-H), 7.46 (d, 1H, J=2.0 Hz, benzimid-H), 7.67 (d, 1H, J=8.6 Hz, benzimid-H), 7.98-8.01 (m, 2H, pyrid-H), 8.49 (s, 1H, pyraz-H), 8.84-8.87 (m, 2H, pyrid-H), 8.99 (s, 1H, pyraz-H), 9.05 (s, 1H, benzimid-H).

Example 18

N-{1-[6-(tert-Butylamino)pyrazin-2-yl]-1H-benzimidazol-6-yl}prop-2-ynamide

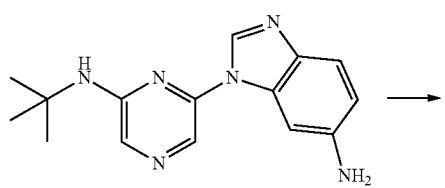

-continued

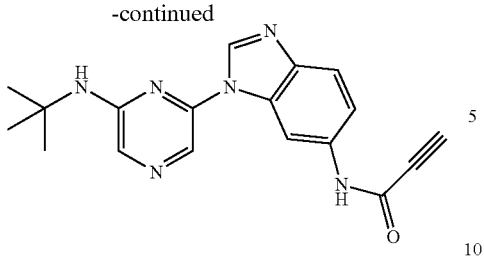

To a stirred solution of 1-[6-(tert-butylamino)pyrazin-2-yl]-1H-benzimidazol-6-amine (70 mg, 0.25 mmol) in anhydrous dichloromethane (2.5 mL) under $N_2$ was added triethylamine (86 μl), EDAC.HCl (60 mg), 4-(1-pyrrolidino)pyridine (4 mg) and propiolic add (18.5 μL). The resulting mixture was then stirred at RT overnight and was the diluted with $CH_2Cl_2$ (10 mL) and washed with $H_2O$ (2×10 mL), 0.5M $Na_2CO_3$ (10 mL) and dried ($Na_2SO_4$). The solvent was removed under reduced pressure and the residue was purified by column chromatography using dichloromethane-methanol (99:1-91:9) as eluant to separate the pure product (1.8 mg).
$^1$H-n.m.r. ($CDCl_3$) δ1.52 (s, 9H, $CH_3$), 4.76 (br s, 1H, NH), 5.78 (br s, 1H, CH), 6.75 (dd, 1H, J=8.4, 2.2 Hz, ArH), 7.22 (d, 1H, J=2.2 Hz, ArH), 7.63 (d, 1H, J=8.0 Hz, Ar—H), 7.79 (s, 1H, pyraz-H), 8.08 (s, 1H, pyraz-H), 8.37 (s, 1H, benzimid-H).

Example 19

N-[1-(6-([(1S)-1-Phenylethyl]amino]pyrazin-2-yl)-1H-benzimidazol-6-yl)acrylamide

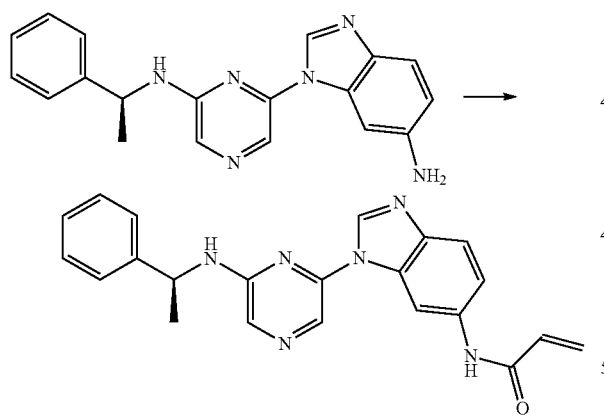

To a stirred solution of 1-(6-{[(1S)-1-phenylethyl]amino}pyrazin-2-yl)-1H-benzimidazol-6-amine (67 mg, 0.2 mmol) in anhydrous THF (2 mL) under $N_2$ was added triethylamine (67 μl, 0.48 mmol), EDACHCl (46 mg, 0.24 mmol), 4-(1-pyrrolidino)pyridine (cat.) and acrylic acid (17 mg, 0.24 mmol). The resulting mixture then stirred at RT overnight and was the diluted with $H_2O$ (10 mL) and the mixture extracted with EtOAc (2×10 mL). The combined organic layers were washed with saturated aqueous $Na_2CO_3$, dried ($Na_2SO_4$) and the solvent removed in vacuo. The residue was purified by column chromatography using dichloromethane-methanol (98:2-94:6) as eluant to separate the pure product (25 mg).
$^1$H-n.m.r. ($CDCl_3$) δ1.62 (d, 3H, J=6.8 Hz, $CH_3$), 5.01-5.13 (m, 1H, CH), 5.38 (d, 1H, J=6.4 Hz, NH), 5.78 (dd, 1H, J=9.8, 2.0 Hz, CH), 6.24-6.52 (m, 2H, 2×CH), 7.29-7.44 (m, 6H, ArH), 7.70-7.74 (m, 2H, Ar—H), 7.82 (s, 1H, pyraz-H), 8.11 (s, 1H, pyraz-H), 8.33 (s, 1H, benzimid-H), 8.42 (s, 1H, CONH).

Example 20

N-{1-[6-(tert-Butylamino)pyrazin-2-yl]-1-H-benzimidazol-6-yl}acrylamide

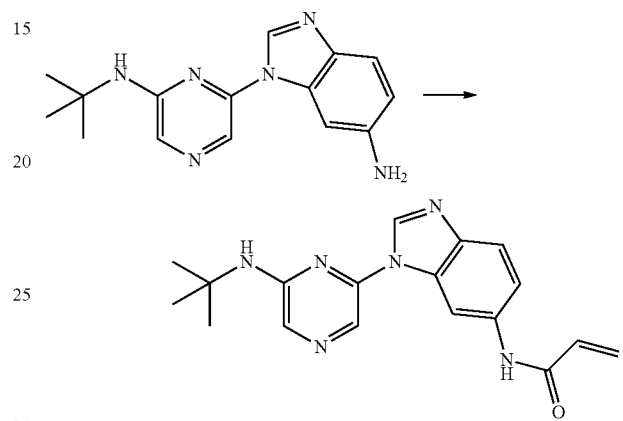

To a stirred solution of 1-[6-(tert-butylamino)pyrazin-2-yl]-1H-benzimidazol-6-amine (22 mg, 0.08 mmol) in anhydrous dichloromethane (2 mL) under $N_2$ was added triethylamine (33 μL, 0.24 mmol), EDAC.HCl (22 mg, 0.12 mmol), 4-(1-pyrrolidino)pyridine (cat.) and acrylic acid (8 μL, 0.12 mmol). The resulting mixture then stirred at RT for 3 days and was the diluted with $H_2O$ (10 mL), the organic phase separated and the aqueous phase extracted with $CH_2Cl_2$ (10 mL). The combined organic layers were dried ($Na_2SO_4$) and the solvent removed in vacuo. The residue was purified by column chromatography using dichloromethane-methanol (98:2-93:7) as eluant to separate the pure product (10 mg).
$^1$H-n.m.r. ($CDCl_3$) δ1.50 (s, 9H, $CH_3$), 4.89 (br s, 1H, NH), 5.77 (dd, 1H, J=10.0, 2.0 Hz, CH), 6.24-6.51 (m, 2H, 2×CH), 7.25 (dd, 1H, J=8.6, 2.0 Hz, ArH), 7.76 (d, 1H, J=8.8 Hz, Ar—H), 7.83 (8, 1H, pyraz-H), 7.88 (br s, 1H, CONH), 8.13 (s, 1H, pyraz-H), 8.52 (s, 1H, benzimid-H), 8.56 (s, 1H, ArH).

Example 21

N-{1-[6-(tert-Butylamino)pyrazin-2-yl]-1H-benzimidazol-5-yl}acrylamide

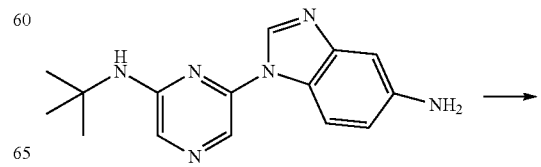

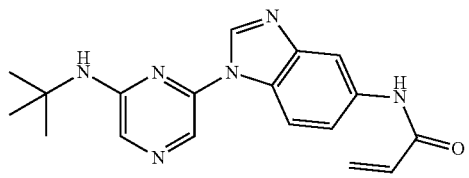

To a stirred solution of 1-[6-(tert-butylamino)pyrazin-2-yl]-1H-benzimidazol-5-amine (20 mg, 0.08 mmol) in anhydrous dichloromethane (2 mL) under $N_2$ was added triethylamine (33 μL, 0.24 mmol), EDAC.HCl (22 mg, 0.12 mmol), 4-(1-pyrrolidino)pyridine (cat.) and acrylic acid (8 μL, 0.12 mmol). The resulting mixture then stirred at RT for 3 clays and was the diluted with $H_2O$ (10 mL), the organic phase separated and the aqueous phase extracted with $CH_2Cl_2$ (10 mL). The combined organic layers were dried ($Na_2SO_4$) and the solvent removed in vacuo. The residue was purified by column chromatography using dichloromethane-methanol (98:2-92:8) as eluant to separate the pure product (10 mg).

$^1$H-n.m.r. (CDCl$_3$) δ1.52 (s, 9H, CH$_5$), 4.87 (br s, 1H, NH), 5.77 (dd, 1H, J=9.8, 2.0 Hz, CH), 6.31 (dd, 1H, J=16.6, 9.8 Hz, =CH(H)), 6.48 (dd, 1H, J=16.6, 2.0 Hz, —, —CH(H)), 7.73-7.81 (m, 2H, pyraz-H ArH), 7.89 (d, 1H, J=8.8 Hz, ArH), 8.01 (s, 1H, ArH), 8.10 (s, 1H, pyraz-H), 855 (s, 1H, benzimid-H).

Example 22

N-{1-[6-(tert-Butylamino)pyrazin-2-yl]-1H-benzimidazol-6-yl}-2-methylacrylamide

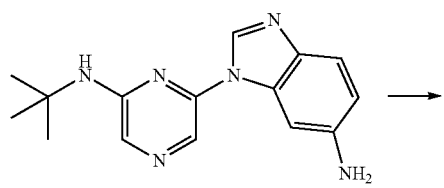

Following a procedure identical to Example 21 however using methacrylic add in place of acrylic acid, 1-[6-(tert-butylamino)pyrazin-2-yl]-1H-benzimidazol-5-amine (57 mg) afforded N-(1-[6-(tert-butylamino)pyrazin-2-yl]-1H-benzimidazol-6-yl)-2-methylacrylamide (54 mg).

$^1$H-n.m.r. (CDCl$_3$+d$_4$-MeOD) δ1.43 (s, 9H, CH$_3$), 2.00 (br s, 3H, CH$_3$), 5.42 (br s, 1H, =CH(H)), 5.77 (br s, 1H, =CH(H)), 7.32 (dd, 1H, J=8.2, 2.0 Hz, ArH), 7.67 (d, 1H, J=8.8 Hz, ArH), 7.74 (s, 1H, pyraz-H), 7.99 (s, 1H, pyraz-H), 8.38 (d, 1H, J=2.0 Hz, ArH), 8.46 (s, 1H, benzimid-H).

Example 23

1-{6-[(2-Methylphenyl)amino]pyrazin-2-yl}-1H-benzimidazol-6-amine

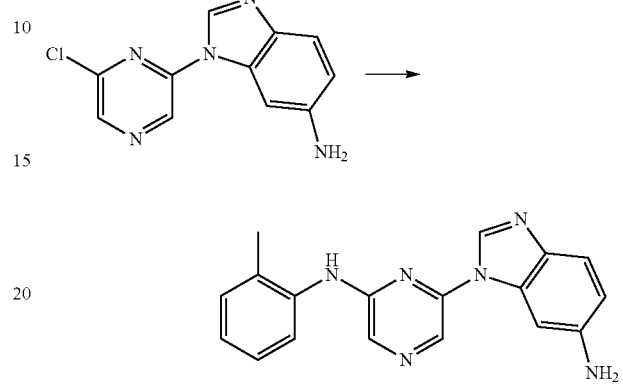

To a stirred solution of the chloropyrazine (100 mg, 0.40 mmol) in toluene (2 mL) was added o-toluidine (0.1 mL, 0.93 mmol), Pd[P(t-Bu)$_3$]$_2$ (10 mg) and sodium t-butoxide (58 mg, 0.6 mmol). The solution was heated at 80° overnight and upon cooling to RT was diluted with EtOAc (20 mL). The organic layer was collected and the aqueous layer extracted with EtOAc (20 mL) and the combined organic layers washed with water, brine, and dried (NO$_2$SO$_4$). Removal of the solvent under reduced pressure gave an oily residue which was chromatographed using CH2Cl2-MeOH (98:2→94:6) to separate the desired product as a pale yellow oil (52 mg, 41%).

$^1$H-n.m.r. (CDCl$_3$) δ2.34 (s, 3H, CH$_3$), 3.70 (s, 2H, NH$_2$), 6.61 (s, 1H, NH), 6.71 (dd; 1H, J=8.6, 2.2 Hz, ArH), 7.19-7.36 (m, 4H, ArH), 7.53-7.60 (m, 2H, ArH), 7.99 (s, 1H, pyraz-H), 8.27 (s, 1H, pyraz-H), 8.36 (s, 1H, benzimid-H).

Example 24

(2Z)-N-{1-[6-(tert-Butylamino)pyrazin-2-yl]-1H-benzimidazol-6-yl}-3-pyridin-3-ylacrylamide

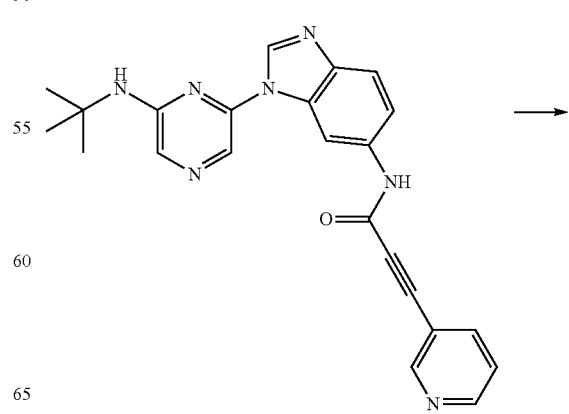

-continued

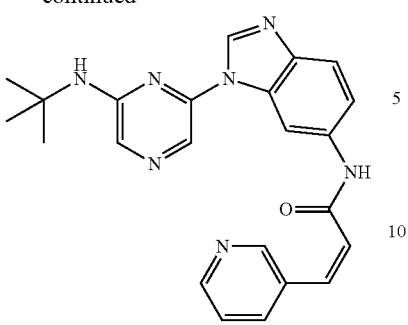

To a stirred solution of the alkyne (30 mg, 0.07 mmol) in anhydrous ethanol (5 mL) was added Lindlar catalyst (3 mg). The mixture was then purged with hydrogen gas and stirred under $H_2$ at atmospheric pressure for 3 h. The catalyst was removed by filtration through Celite® and the solvent removed in vacuo. Flash chromatography using EtOAc-MeOH (9:1) separated pure product as a sticky semi-solid (13 mg, 43%).

$^1$H-n.m.r. (CDCl$_3$) δ1.50 (s, 9H, C(CH$_3$)$_3$), 4.93 (s, 1H, NH), 6.26 (d, J=12.6 Hz, C=CH), 6.82 (d, 1H, J=12.6 Hz, C=CH), 7.14 (dd, 1H, J=8.7, 2.1 Hz, ArH), 7.25-7.29 (m, 1H, pyridine-H), 7.74 (d, 1H, J=8.7 Hz, ArH), 7.82 (s, 1H, pyraz-H), 8.07 (br s, 1H, CONH), 8.09 (s, 1H, pyraz-H), 8.13-8.16 (m, 1H, pyridine-H), 8.47 (d, 1H, t=1.8 Hz, pyridine-H), 8.50 (s, 1H, benzimid-H), 8.51-8.53 (m, 1H, pyridine-H), 8.63 (d, 1H, J=2.1 Hz, ArH).

m/z (EI): 413 (M$^+$).

Example 25

N-(tert-Butyl)-6-chloropyrazine-2-carboxamide

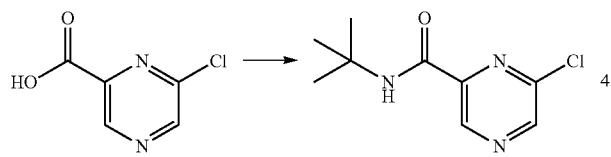

Thionyl chloride (1 mL, 13.7 mmol) was added to a suspension of the acid (315 mg, 2 mmol) in toluene (5 mL). A drop of DMF was then added and after stirring at RT for 10 min. the mixture was heated at reflux for 1 h. The reaction was cooled to RT and toluene and excess thionyl chloride were removed under reduced pressure. Toluene (1 mL) was then added to the residue and this was removed under reduced pressure. This process was repeated, and then CH$_2$Cl$_2$ (10 mL) was added and the resulting solution cooled to t-Butylamine (0.45 mL, 4.3 mmol) and triethylamine (1.1 mL, 8.0 mmol) were than added and the solution stirred at RT overnight. The solution was diluted with CH$_2$Cl$_2$ (10 mL) and H$_2$O (10 mL) and the organic layer collected and washed with aq. Na$_2$CO$_3$ and then dried (Na$_2$SO$_4$). The solvent was removed in vacuo and flash chromatography of the residue using CH$_2$Cl$_2$-MeOH (95:5) separated the pure product as an oil (290 mg, 68%).

$^1$H-n.m.r. (CDCl$_3$) δ1.49 (s, 9H, C(CH$_3$)$_3$), 7.48 (br s, 1H, NH), 8.72 (s, 1H, pyraz-H), 9.27 (s, 1H, pyraz-H).

m/z (EI): 413 (M$^+$).

Example 26

1-(6-Methoxypyridin-3-yl)-5-nitro-1H-benzimidazole and 1-(6-methoxypyridin-3-yl)-6-nitro-1H-benzimidazole

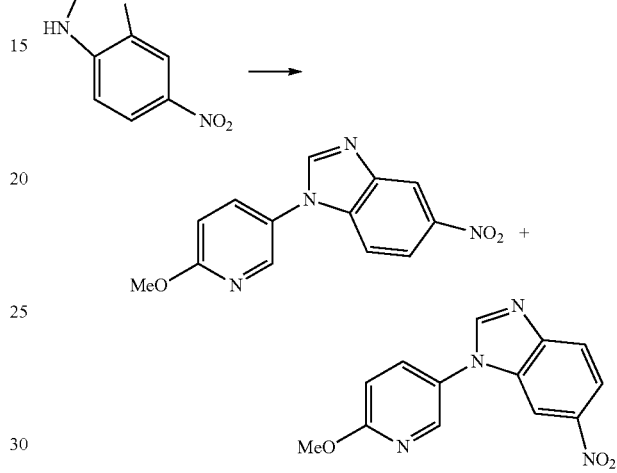

A mixture of 5-nitrobenzimidazole (650 mg, 4 mmol), 2-methoxy-5-pyridylboronic add (420 mg, 2.6 mmol), copper (II) acetate (1.09 g, 6 mmol) and powdered 4 Å sieves was stirred vigorously in CH$_2$Cl$_2$ (40 mL) containing pyridine (0.65 mL) was stirred in the air over 3 days. The mixture was then filtered through Celite® and the filter pad washed with CH$_2$Cl$_2$-MeOH (4:1). The filtrate and washings were combined, concentrated hr vacuo and the residue chromatographed using CH$_2$Cl$_2$-MeOH (100:0→95:5) to separate the product (as a 1:1 mixture of regiomers) as a white solid (272 mg, 37%).

m/z (EI): 270 (M$^+$).

Example 27

1-(6-Methoxypyridin-3-yl)-1H-benzimidazol-5-amine and 1-(6-methoxypyridin-3-yl)-1H-benzimidazol-6-amine

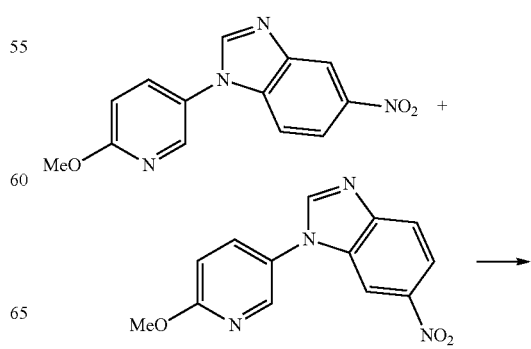

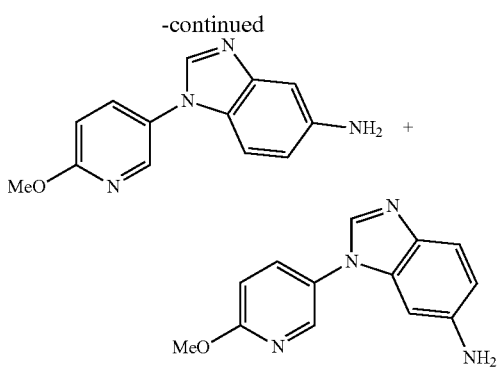

The mixture of regioisomers derived from Example 26 (270 mg, 1 mmol) was hydrogenated following the procedure outlined in Example 10. The crude product was chromatographed eluting with CH₂Cl₂-MeOH (98:2→95:5) to separate the 6-isomer (84 mg) from the less polar fractions and the 5-isomer from the polar fractions. (122 mg).

6-Isomer:

¹H-n.m.r. (CDCl₃) δ 3.88 (br s, 2H, NH₂), 4.01 (s, 3H, OCH₃), 6.64 (d, 1H, J=2.1 Hz, benzimid-H), 6.72 (dd, 1H, J=8.7, 2.1 Hz, benzimid-H), 6.92 (d, 1H, J=9.0 Hz, benzimid-H), 7.61-7.68 (m, 2H, pyr-H), 7.82 (s, 1H, benzimid-H), 8.30 (d, 1H, J=2.7 Hz, pyr-H).

5-Isomer:

¹H-n.m.r. (CDCl₃) δ3.11 (br s, 2H, NH₂), 4.01 (s, 3H, OCH₃), 6.75 (dd, 1H, J=8.4, 2.1 Hz, benzimid-H), 6.92 (d, 1H, J=8.7 Hz, benzimid-H), 7.15 (d, 1H, J=2.1 Hz, benzimid-H), 7.18 (d, 1H, J=8.7 Hz, pyr-H), 7.68 (dd, 1H, J=8.7, 2.7 Hz, pyr-H), 7.91 (s, 1H, benzimid-H), 8.31 (d, 1H, J=2.7 Hz, pyr-H).

Example 28

1-(5-Bromopyridin-3-yl)-1H-benzimidazol-6-amine and 1-(5-bromopyridin-3-yl)-1H-benzimidazol-5-amine

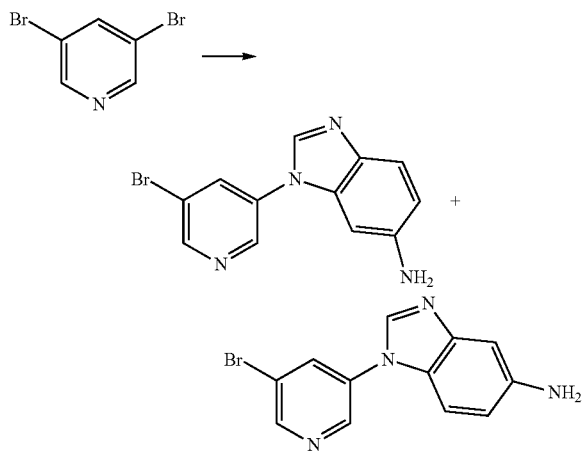

A solution of 3,5-dibromopyridine (2.37 g, 10 mmol), 5-aminobenzimidazole (1.60 g, 12 mmol) and caesium carbonate (4.9 g, 15 mmol) in DMSO (10 mL) Wee heated at 150° for 18 h. Upon cooling to RT the solution was diluted with CHCl₃ (40 mL) and filtered through Celite® and the filtrate concentrated is vacuo. The residue was chromatographed (pre-adsorption to silica) eluting with EtOAc-MeOH (100:0→95:5) to separate, from the less polar fractions, the 6-isomer, and from the more polar fractions the 5-isomer.

6-Isomer:

¹H-n.m.r. (CDCl₃) δ 3.82 (br s, 2H, NH₂), 6.75-6.78 (m, 2H), 7.64 (d, 1H, J=9.0 Hz, benzimid-H), 7.89 (s, 1H), 8.01 (dd, 1H, J=2.1 Hz, pyr-H), 8.75 (br s, 2H).

5-Isomer:

¹H-n.m.r. (CDCl₃) δ3.74 (br s, 2H, NH₂), 6.79 (dd, 1H, J=8.7, 2.1 Hz, benzimid-H), 7.15 (d, 1H, J=2.1 Hz, benzimid-H), 7.31 (d, 1H, J=8.7 Hz, benzimid-H), 7.99 (s, 1H, benzimid-H), 8.01 (dd, 1H, J=2.1, 2.1 Hz, pyr-H), 8.74-8.77 (m, 2H, pyr-H).

Example 29

1-(6-Bromopyridin-2-yl)-1H-benzimidazol-6-amine and 1-(6-bromopyridin-2-yl)-1H-benzimidazol-5-amine

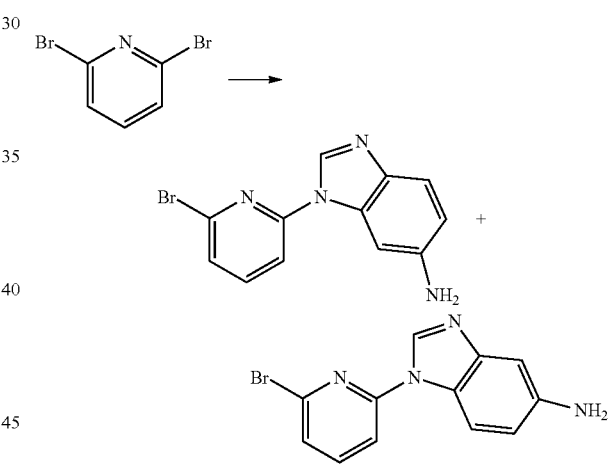

Using identical procedures to those outlined in Example 28, reaction of 2,6-dibromopyridine with 5-aminobenzimidazole and caesium carbonate in DMSO at 150° afforded the two regioisomeric products which were separated by chromatography.

6-Isomer:

¹H-n.m.r. (CDCl₃) δ 3.83 (br s, 2H, NH₂), 6.75 (dd, 1H, J=8.4, 2.1 Hz, benzimid.-H), 7.42-7.47 (m, 3H), 7.60 (d, 1H, J=8.4 Hz), 7.71 (dd, 1H, J=7.8 Hz), 8.33 (s, 1H).

5-Isomer:

¹H-n.m.r. (CDCl₃) δ6.81 (dd, 1H, J=8.7, 2.1 Hz, benzimid-H), 7.12 (d, 1H, J=8.1 Hz, benzimid-H), 7.40-7.48 (m, 2H), 7.70 (dd, 1H, J=7.8, 7.8 Hz, pyr-H), 7.89 (d, 1H, J=8.7 Hz, benzimid-H), 8.46 (s, 1H).

The following compounds were prepared using analogous procedures to those described above:

| Compound | Structure | Data |
|---|---|---|
| N-[1-(6-Chloropyrazin-2-yl)-1H-benzimidazol-6-yl]acrylamide | 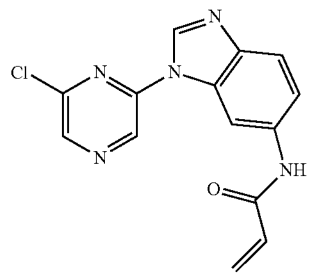 | ¹H-n.m.r. (CDCl₃) δ 5.82 (dd, 1H, J = 9.8, 1.8 Hz, =CH), 6.24-6.54 (m, 2H, =CH₂), 7.33 (dd, 1H, J = 8.8, 1.8 Hz, ArH), 7.60 (br s, 1H, CONH), 7.80 (d, 1H, J = 8.4 Hz, ArH), 8.58 (s, 2H, pyraz-H), 8.73 (br s, 1H, ArH), 8.94 (br s, 1H, ArH). |
| N-{1-[6-(4-Methylpiperazin-1-yl)pyrazin-2-yl]-1H-benzimidazol-6-yl}acrylamide | 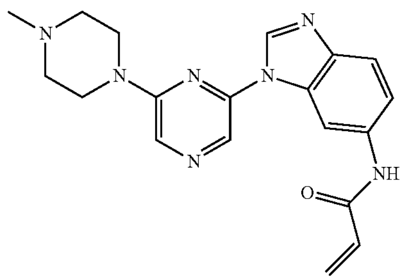 | ¹H-n.m.r. (CDCl₃) δ 2.34 (s, 3H, NCH₃), 2.55 (t, 4H, J = 5.1 Hz, CH₂), 3.74 (t, 4H, J = 5.1 Hz, CH₂), 5.72 (dd, 1H, J = 9.0, 2.6 Hz, CH), 6.25-6.48 (m, 2H, =CH₂), 7.14 (dd, 1H, J = 8.4, 2.2 Hz, ArH), 7.68 (d, 1H, J = 8.6 Hz, ArH), 8.04 (s, 1H, pyraz-H), 8.13 (s, 1H, pyraz-H), 8.38 (br s, 1H, CONH), 8.46 (s, 1H, ArH), 8.88 (br s, 1H, ArH). |
| N-{1-[6-(Diethylamino)pyrazin-2-yl]-1H-benzimidazol-6-yl}acrylamide | 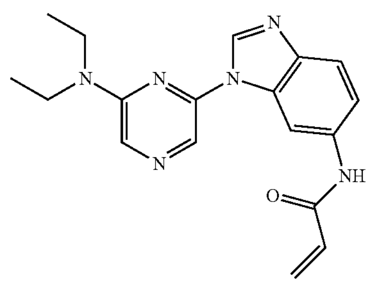 | ¹H-n.m.r. (CDCl₃) δ 1.24 (d, 6H, J = 7.0 Hz, CH₃), 3.60 (q, 4H, J = 7.1 Hz, CH₂), 5.72 (dd, 1H, J = 9.0, 2.7 Hz, =CH), 6.25-6.49 (m, 2H, =CH₂), 7.20 (dd, 1H, J = 8.9, 2.0 Hz, ArH), 7.71 (d, 1H, J = 8.4 Hz, ArH), 7.91 (s, 1H, pyraz-H), 8.07 (s, 1H, pyraz-H), 8.33 (br s, 1H, CONH), 8.49 (s, 1H, ArH), 8.76 (br s, 1H, ArH). |
| N-{1-[6-(Methylamino)pyrazin-2-yl]-1H-benzimidazol-6-yl}acrylamide | 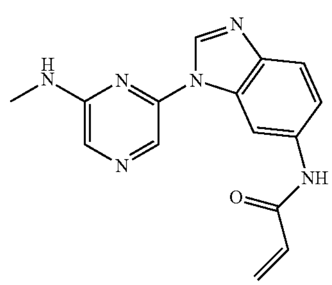 | ¹H-n.m.r. (CDCl₃) δ 3.11 (d, 3H, J = 5.0 Hz, CH₃), 4.9 (br s, 1H, NH), 5.78 (dd, 1H, J = 9.8, 2.2 Hz, =CH), 6.23-6.51 (m, 2H, =CH₂), 7.15 (dd, 1H, J = 8.4, 2.2 Hz, ArH), 7.63 (br s, 1H, CONH), 7.76 (d, 1H, J = 8.6 Hz, ArH), 7.86 (s, 1H, pyraz-H), 8.13 (s, 1H, pyraz-H), 8.33 (s, 1H, ArH), 8.90 (s, 1H, ArH). |
| N-{1-[6-(Ethylamino)pyrazin-2-yl]-1H-benzimidazol-6-yl}acrylamide | 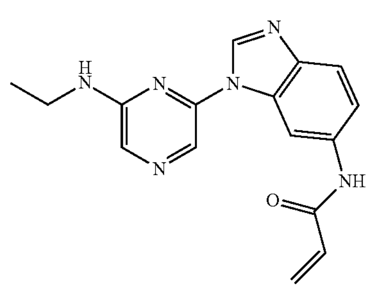 | ¹H-n.m.r. (CDCl₃/d₄-MeOD) δ 1.25 (t, 3H, J = 7.3 Hz, CH₃), 3.42 (q, 2H, J = 7.3 Hz, CH₂), 5.68 (dd, 1H, J = 7.8, 4.6 Hz, =CH), 6.23-6.42 (m, 2H, =CH₂), 7.24 (dd, 1H, J = 8.6, 2.2 Hz, ArH), 7.63 (d, 1H, J = 8.8 Hz, ArH), 7.73 (s, 1H, pyraz-H), 7.97 (s, 1H, pyraz-H), 8.44 (s, 1H, ArH), 8.73 (br s, 1H, ArH). |

-continued

| Compound | Structure | Data |
|---|---|---|
| N-[1-(6-piperidin-1-ylpyrazin-2-yl)-1H-benzimidazol-6-yl]acrylamide | 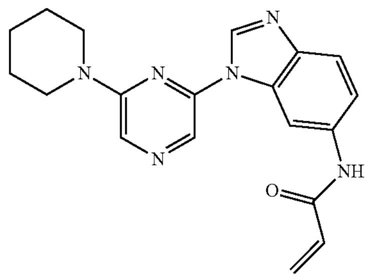 | m/z (EI) 348 (M$^+$) |
| N-[1-(6-morpholin-4-ylpyrazin-2-yl)-1H-benzimidazol-6-yl]acrylamide | 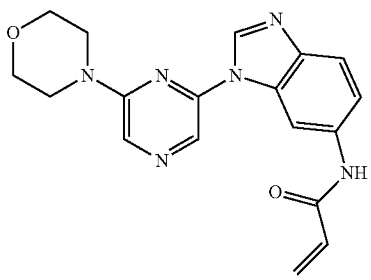 | m/z (EI) 350 (M$^+$) |
| N-[1-(6-pyrrolidin-1-ylpyrazin-2-yl)-1H-benzimidazol-6-yl]acrylamide | 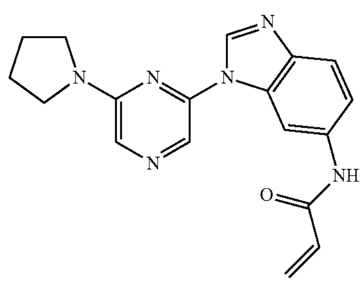 | m/z (EI) 334 (M$^+$) |
| N-{1-[6-(dimethylamino)pyrazin-2-yl]-1H-benzimidazo]-6-yl}acrylamide | 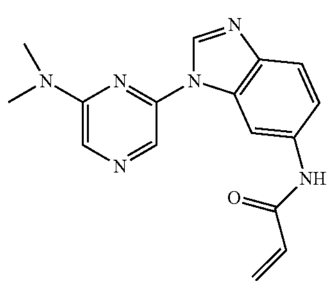 | m/z (EI) 308 (M$^+$) |
| N-(1-[6-[isopropyl(methyl)amino]pyrazin-2-yl]-1H-benzimidazol-6-yl)acrylamide | | m/z (EI) 336 (M$^+$) |

| Compound | Structure | Data |
|---|---|---|
| N-{1-[6-(Isopropylamino)pyrazin-2-yl]-1H-benzimidazol-6-yl]acrylamide | 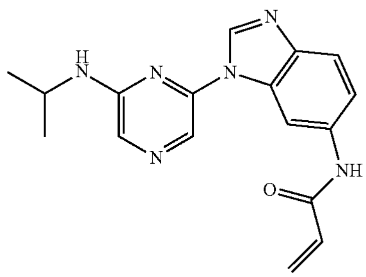 | ¹H-n.m.r. (CDCl₃) δ 1.32 (d, 6H, J = 6.2 Hz, CH₃), 4.13-4.29 (m, 1H, CH), 4.75 (d, 1H, J = 7.8 Hz, NH), 5.78 (dd, 1H, J = 9.8, 2.0 Hz, =CH), 6.22-6.51 (m, 2H, =CH₂), 7.19 (dd, 1H, J = 8.6, 2.2 Hz, ArH), 7.62 (br s, 1H, CONH), 7.76 (d, 1H, J = 8.8 Hz, ArH), 7.82 (s, 1H, pyraz-H), 8.13 (s, 1H, pyraz-H), 8.50 (s, 1H, ArH), 8.74 (br s, 1H, ArH). |
| N-[1-(6-{[(1S)-1-methylpropyl]amino}pyrazin-2-yl)-1H-benzimidazol-6-yl]acrylamide | 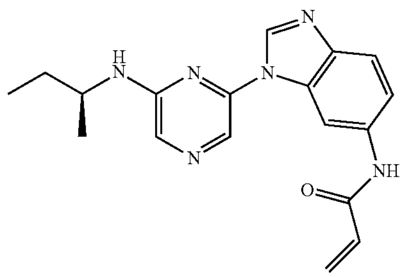 | ¹H-n.m.r. (CDCl₃) δ 0.99 (t, 3H, J = 7.2 Hz, CH₃), 1.27 (d, 3H, J = 6.4 Hz, CH₃), 1.53-1.73 (m, 2H, CH₂), 3.95-4.09 (m, 1H, CH), 4.79 (d, 1H, J = 8.0 Hz, NH), 5.76 (dd, 1H, J = 9.6, 2.0 Hz, =CH), 6.23-6.50 (m, 2H, =CH₂), 7.21 (dd, 1H, J = 8.6, 2.2 Hz, ArH), 7.74 (d, 1H, J = 8.8 Hz, ArH), 7.82 (s, 1H, pyraz-H), 7.84 (br s, 1H, CONH), 8.11 (s, 1H, pyraz-H), 8.49 (s, 1H, ArH), 8.73 (br s, 1H, ArH). |
| N-[1-(6-{[(1R)-1-methylpropyl]amino}pyrazin-2-yl)-1H-benzimidazol-6-yl]acrylamide | 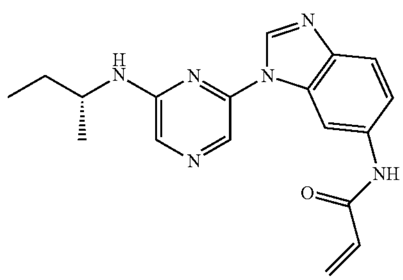 | ¹H-n.m.r. (CDCl₃) δ 0.99 (t, 3H, J = 7.2 Hz, CH₃), 1.27 (d, 3H, J = 6.4 Hz, CH₃), 1.53-1.73 (m, 2H, CH₂), 3.95-4.08 (m, 1H, CH), 4.81 (d, 1H, J = 8.0 Hz, NH), 5.75 (dd, 1H, J = 9.6, 2.0 Hz, =CH), 6.23-6.50 (m, 2H, =CH₂), 7.22 (dd, 1H, J = 8.6, 2.2 Hz, ArH), 7.73 (d, 1H, J = 8.8 Hz, ArH), 7.81 (s, 1H, pyraz-H), 7.98 (br s, 1H, CONH), 8.10 (s, 1H, pyraz-H), 8.49 (s, 1H, ArH), 8.73 (br s, 1H, ArH). |
| N-[1-(6-Anilinopyrazin-2-yl)-1H-benzimidazol-6-yl]acrylamide | 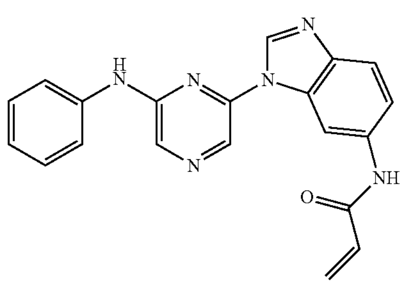 | ¹H-n.m.r. (CDCl₃ + d₄-MeOD) δ 529 (ad, 1H, J = 9.0, 3.0 Hz, =CH), 6.40 (1H, d, J = 9.0 Hz, =CH(H)), 6.43 (1H, d, J = 3.0 Hz, =CH(H)), 7.11-7.18 (m, 1H, ArH), 7.30-7.44 (m, 3H, ArH), 7.52-7.56 (m, 2H, ArH), 7.75 (d, 1H, J = 8.8 Hz, ArH), 8.20 (3, 1H, pyraz-H), 8.27 (s, 1H, pyraz-H), 8.56 (N, 1H, ArH), 8.79 (br s, 1H, ArH). |
| N-[1-(6-Phenylpyrazin-2-yl)-1H-benzimidazol-6-yl]acrylamide | 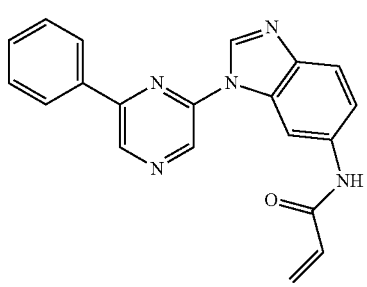 | ¹H-n.m.r. (CDCl₃) δ 5.70 (dd, 1H, J = 8.6, 2.2 Hz, =CH), 6.22-6.46 (m, 2H, =CH₂), 7.29 (dd, 1H, J = 8.6, 1.4 Hz, ArH), 7.47-7.57 (m, 3H, ArH), 7.68 (d, 1H, J = 8.8 Hz, ArH), 8.12-8.16 (m, 2H, ArH), 8.65 (s, 1H, pyraz-H), 8.89 (s, 1H, pyraz-H), 8.91 (s, 1H, ArH), 8.97 (s, 1H, AH). |

-continued

| Compound | Structure | Data |
|---|---|---|
| N-{1-[6-(3-Chloro-4-fluorophenyl)pyrazin-2-yl]-1H-benzimidazol-6-yl}acrylamide | 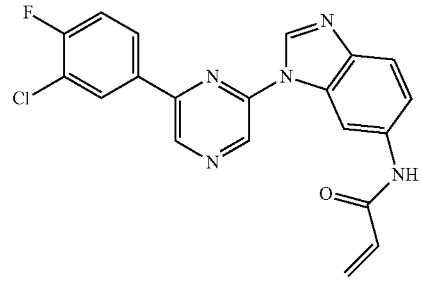 | m/z (EI) 393, 395 (~3:1) (M$^+$) |
| N-[1-(6-Pyridin-3-ylpyrazin-2-yl)-1H-benzimidazol-6-yl]acrylanude | 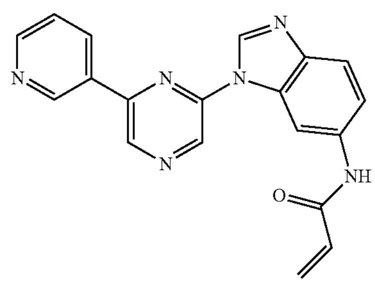 | m/z (EI) 342 (M$^+$) |
| N-[1-(6-Thien-3-ylpyrazin-2-yl)-1H-benzimidazol-6-yl]acrylamide | 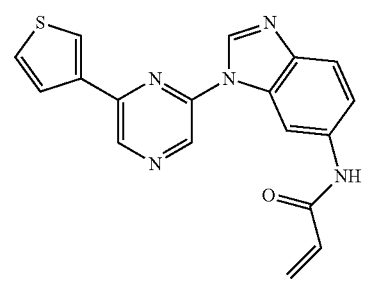 | m/z (EI) 347 (M$^+$) |
| N-{1-[6-(1H-Pyrazol-4-yl)pyrazin-2-yl]-1H-benzimidazol-6-yl}acrylamide | 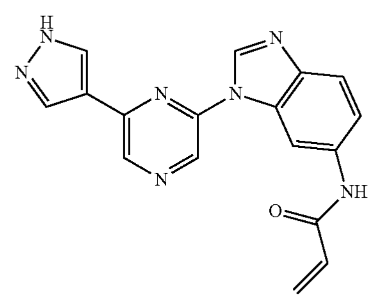 | m/z (EI) 531 (M$^+$) |
| N-{1-[6-(3,4,5-trimethoxyphenyl)pyrazin-2-yl]-1H-benzimidazol-6-yl}acrylamide | 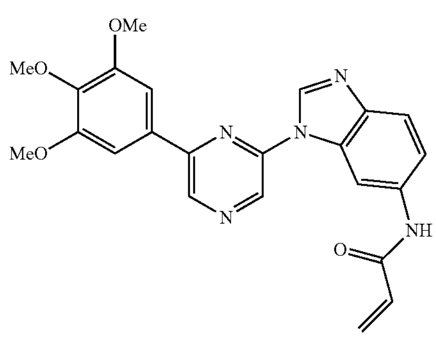 | m/z (EI) 431 (M$^+$) |

| Compound | Structure | Data |
|---|---|---|
| 1-Methyl-N-{1-[6-(t-butylamino)pyrazin-2-yl]-1H-benzimidazol-6-yl}-1,2,5,6-tetrahydropyridine-3-carboxamide | 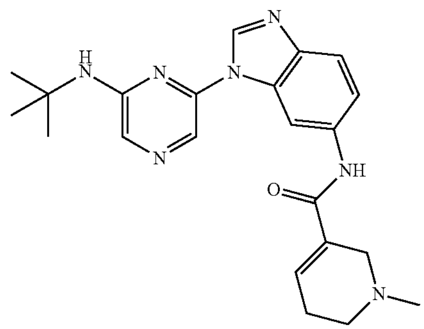 | m/z (EI) 405 (M⁺) |
| N-{1-[6-(tert-butylamino)pyrazin-2-yl]-1H-benzimidazol-6-yl}but-2-enamide | 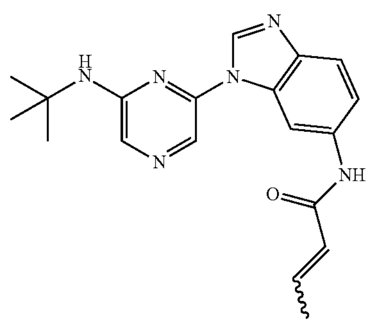 | m/z (EI) 350 (M⁺) |
| N-{1-[6-(tert-Butylamino)pyrazin-2-yl]-1H-benzimidazol-6-yl}but-2-ynamide | 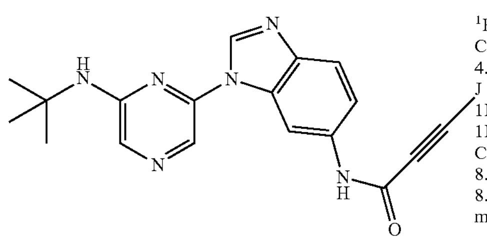 | $^1$H-n.m.r. (CDCl$_3$) δ 1.50 (s, 9H, C(CH3)3), 1.98 (s, 3H, CH3), 4.93 (s, 1H, NH), 7.20 (dd, 1H, J = 8.4, 2.0 Hz, ArH), 7.76 (d, 1H, J = 8.8 Hz, ArH), 7.83 (s, 1H, pyraz-H), 7.95 (br s, 1H, CONH), 8.08 (s, 1H, pyraz-H), 8.44 (d, 1H, J = 2.0 Hz, ArH), 8.49 (s, 1H, benzimid-H), m/z (EI): 348 (M+). |
| N-(1-{6-[(2-methylphenyl)amino)pyrazin-2-yl}-1H-benzimidazol-6-yl)acrylamide | | $^1$H-n.m.r. CDCl$_3$/CD$_3$OD (v/v = 49/1) δ 2.35 (s, 3H, CH$_3$), 5.75-5.83 (m, 1H, C=CH), 6.39-6.49 (m, 2H, 2 x C=CH), 7.19-7.34 (m, 3H, 3ArH), 7.41(dd, 1H, J = 7.5, 1.4 Hz, ArH), 7.71 (d, 1H, J = 8.7 Hz, ArH), 7.92 (s, 1H, pyraz-H), 8.25 (s, 1H, pyran-H), 8.57 (s, 1H, benzimid-H), 8.76 (d, 1H, J = 1.8 Hz, ArH). m/z (EI): 370 (M⁺). |
| N-(1-[6-[(5-chloro-2-methylphenyl)amino]pyrazin-2-yl]-1H-benzimidazol-6-yl)acrylamide | | $^1$H-n.m.r. CDCl$_3$/CD$_3$OD (v/v = 19/1) δ 2.32 (s, 3H, CH$_3$), 5.77-5.81 (m, 1H, C=CH), 6.33-6.49 (m, 2H, 2 x C=CH), 7.15 (dd, 1H, J = 8.1, 2.1 Hz, ArH), 7.24 (d, 1H, J = 8.1 Hz, ArH), 7.39 (dd, 1H, J = 8.7, 1.8 Hz, ArH), 7.62 (d, 1H, J = 2.1 Hz, ArH), 7.74 (d, 1H, J = 8.7 Hz, ArH), 7.98 (s, 1H, pyraz-H), 8.31 (s, 1H, pyraz-H), 8.53 (s, 1H, benzimid-H), 8.77 (d, 1H, J = 1.5 Hz, ArH). m/z (EI): 404, 406 (both M⁺). |

| Compound | Structure | Data |
|---|---|---|
| N-[1-[6-(tert-Butylamino)pyrazin-2-yl]-1H-benzimidazol-6-yl]-3-pyridin-3-ylprop-2-ynamide | 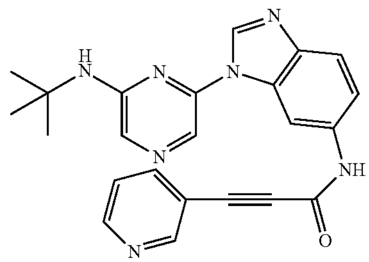 | 1H-n.m.r. CDCl$_3$/CD$_3$OD (v/v = 19/1) δ 1.50 (s, 9H, C(CH$_3$)$_3$), 7.34-7.42 (m, 2H, ArH + pyridine-H), 7.76 (d, 1H, J = 8.7 Hz, ArH), 7.82 (s, 1H, pyraz-H), 7.90-7.94 (m, 1H, pyridine-H), 8.04 (s, 1H, pyraz-H), 8.48 (d, 1H, J = 2.1 Hz, ArH), 8.49 (s, 1H, benzimid-H), 8.32-8.61 (m, 1H, pyridine-H), 8.76-8.77 (m, 1H, pyridine-H). m/z (EI): 411 (M$^+$). |
| N-(1-{6-[(2-chloro-6-methylphenyl)amino]pyrazin-2-yl}-1H-benzimidazol-6-yl)acrylamide | 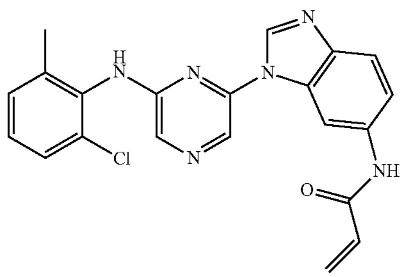 | $^1$H-n.m.r. CDCl$_3$/CD$_3$OD (v/v = 19/1) δ 2.33 (s, 3H, CH$_3$), 5.75-579 (m, 1H, C=CH), 6.32-6.48 (m, 2H, 2 x C=CH), 7.18-7.26 (m, 2H, 2ArH), 7.36-7.39 (m, 2H, 2ArH), 7.63 (s, 1H, pyraz-H), 7.69 (d, 1H, J = 8.7 Hz, ArH), 8.27 (s, 1H, pyraz-H), 8.49 (s, 1H, benzimid-H), 8.69 (br s, 1H, ArH). m/z (EI): 404, 406 (both M$^+$). |
| N-(1-[6-[(3-methylpyridin-2-yl)amino]pyrazin-2-yl]-1H-benzimidazol-6-yl)acrylamide | 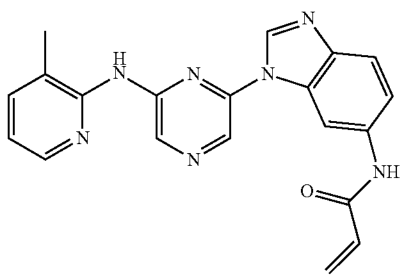 | $^1$H-n.m.r. CDCl$_3$/CD$_3$OD (v/v = 19/1) δ 2.44 (s, 3H, CH$_3$), 5.75-3.79 (m, 1H, C=CH), 6.36-6.48 (m, 2H, 2 x C=CH), 6.97-7.01(m, 1H, pyridine-H), 7.37 (dd, 1H, J = 8.7, 2.1 Hz, ArH), 7.39-7.57 (m, 1H, pyridine-H), 7.73 (d, 1H, J = 8.4 Hz, ArH), 8.22-8.24 (m, 1H, pyridine-H), 8.47 (s, 1H, pyraz-H), 8.58 (s, 1H, pyraz-H), 8.90 (d, 1H, J = 1.5 Hz, ArH), 9.44 (s, 1H, benzimid-H). m/z (EI): 371 (M$^+$). |
| N-(1-[6-[(3-methylpyridin-2-yl)amino]pyrazin-2-yl}-1H-benzimidazol-6-yl)but-2-ynamide | 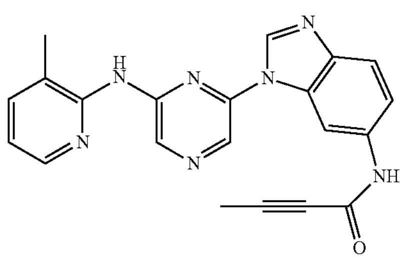 | $^1$H-n.m.r. CDCl$_3$/CD$_3$OD (v/v = 4/1) δ 2.03 (s, 9H, C(CH$_3$)$_3$), 2.42 (s, 3H, CH$_3$), 6.96-7.00 (m, 1H, pyridine-H), 7.34 (d, 1H, J = 8.1 Hz, ArH), 7.54-7.56 (m, 1H, pyridine-H), 7.59-7.72 (m, 1H, pyridine-H), 8.22-8.24 (m, 1H, pyridine-H), 8.45 (8, 1H, pyraz-H), 8.58 (s, 1H, pyraz-H), 8.69 (br s, 1H, ArH), 9.45 (s, 1H, benzimid-H). m/z (EI): 383 (M$^+$). |
| N-(1-{6-[(2-chloro-6-methylphenyl)amino]pyrazin-2-yl)-1H-benzimidazol-6-yl)but-2-ynamide | 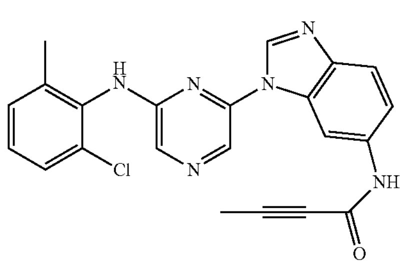 | $^1$H-n.m.r. (CDCl$_3$) δ 2.08 (s, 3H, CH$_3$), 2.34 (s, 3H, CH$_3$), 6.57 (s, 1H, NH), 7.30-7.32 (m, 2H, 2ArH), 7.42-7.52 (m, 3H, 3ArH), 7.75 (d, 1H, J = 8.7 Hz, ArH), 7.84 (s, 1H, pyraz-H), 8.06 (br s, 1H, CONH), 8.35 (s, 1H, pyraz-H), 8.48 (s, 1H, benzimid-H). m/z (EI): 416,418 (both M$^+$). |

| Compound | Structure | Data |
|---|---|---|
| (2E)-N-[1-[6-tert-Butylamino)pyrazin-2-yl)-1H-benzimidazol-6-yl)-3-pyridin-3-ylacrylamide | 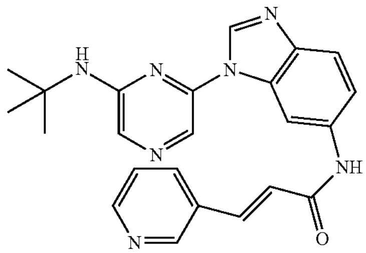 | $^1$H-n.m.r. (CDCl$_3$) δ1.51 (s, 9H, C(CH$_3$)$_3$), 4.81 (s, 1H, NH), 6.66 (d, 1H, J = 15.6 Hz, C═CH), 7.24-7.33 (m, 2H, ArH + pyridine-H), 7.75 (d, 1H, J = 15.6 Hz, C═CH), 7.78-7.81 (m, 3H, 2ArH + CONH), 7.83 (s, 1H, pyraz-H), 8.15 (s, 1H, pyraz-H), 8.52 (s, 1H, benzimid-H), 8.58-8.60 (m, 2H, 2 x pyridine-H), 8.79 (br s,1H, ArH). m/z (EI): 413 (M$^+$). |
| N-(1-{6-[(2,3-dichlorophenyl)amino)pyrazin-2-yl]-1H-benzimidazol-6-yl)acrylamide | 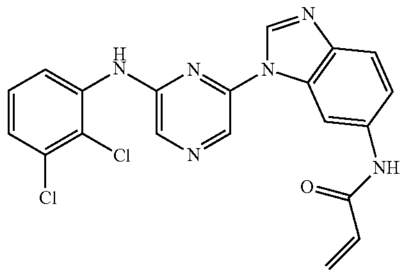 | $^1$H-n.m.r. CDCl$_3$/CD$_3$OD (v /v = 9/1): 5.75-5.79 (m, 1H, C═CH), 6.34-6.46 (m, 2H, 2 x C═CH), 7.24-7.26 (m, 2H, 2ArH), 7.28-7.38 (m, 1H, ArH), 7.72 (d, 1H, J = 8.7 Hz, ArH), 7.96-7.99 (m, 1H, ArH), 8.20 (s, 1H, pyraz-H), 8.40 (s, 1H, pyraz-H), 852 (s, 1H, benzimid-H), 8.72 (br s, 1H, ArH). m/z (EI): 424, 426, 428 (all M$^+$). |
| N-(1-{6-[(2,5-dichlorophenyl)amino]pyrazin-2-yl)-1H-benzimidazol-6-yl)acrylamide | 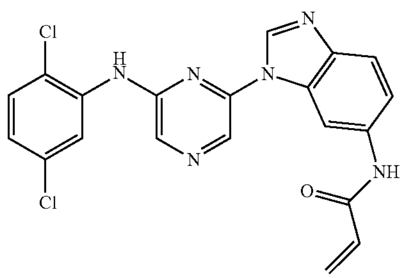 | $^1$H-n.m.r. CDCl$_3$/CD$_3$OD (v/v = 9/1): 5.75-5.79 (m, 1H, C═CH), 6.40-6.48 (m, 2H, 2 x C═CH), 7.06 (dd, 1H, J = 8.7, 2.4 Hz, ArH), 7.39-7.45 (m, 2H, 2ArH), 7.73 (d, 1H, J = 8.7 Hz, ArH), 8.21 (d, 1H, J = 2.4 Hz, ArH), 8.30 (s, 1H, pyraz-H), 8.44 (s, 1H, pyraz-H), 8.60 (s, 1H, benzimid-H), 8.71 (br s, 1H, ArH). m/z (m): 424, 426, 428 (all M$^+$). |
| N-{1-[6-(tert-butylamino)pyrazin-2-yl]-1H-benzimidazol-6-yl}-3-pyridin-3-ylprop-2-ynamide | 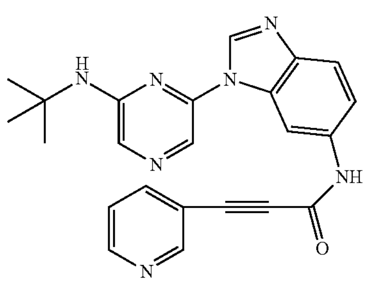 | $^1$H-n.m.r. CDCl$_3$/CD$_3$OD, (v/v = 19/1): 2.33 (s, 3H, CH$_3$), 7.24-7.29 (m, 2H, 2ArH), 7.36-7.42 (m, 2H, ArH + pyridine-H), 7.51 (dd, 1H, J = 8.7, 1.8 Hz, ArH), 7.73-7.75 (m, 2H, ArH + pyraz-H), 7.91-7.95 (m, 1H, pyridine-H), 8.29 (s, 1H, pyraz-H), 8.43 (br s, 1H, ArH), 8.50 (s, 1H, benzimid-H), 8.62-8.64 (m, 1H, pyridine-H), 8.80 (d, 1H, J = 1.5 Hz, pyridine-H). m/z (EI): 479, 481 (both M$^+$). |
| 6-[6-(Acryloylamino)-1H-benzimidazol-1-yl]-N-(tert-butyl)pyrazine-2-carboxamide | 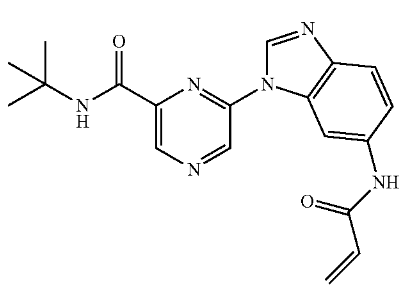 | $^1$H-n.m.r. CDCl$_3$ δ 1.56 (s, 9H, C(CH$_3$)$_3$), 5.76 (dd, 1H, J = 9.5, 1.7 Hz, C═CH), 6.31 (dd, 1H, J = 16.9, 9.5 Hz, C═CH), 6.48 (dd, 1H, J = 16.9, 1.8 Hz, C═CH), 7.09 (dd, 1H, J = 8.9, 1.9 Hz, ArH), 7.62 (br s, 1H, CONH), 7.76-7.80 (m, 2H, 2ArH), 8.51 (s, 1H, pyraz-H), 9.10 (br s, 2H, pyraz-H + CONH), 9.38 (s, 1H, benzimid-H). m/z (EI): 364 (M$^+$). |

| Compound | Structure | Data |
| --- | --- | --- |
| 6-[6-(Acryloylamino)-1H-benzimidazol-1-yl]-N-isopropylpyrazino-2-carboxamide | 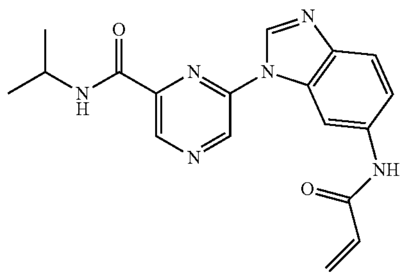 | CDCl$_3$/CD$_3$OD (v/v = 9/1): 1.42 (d, 6H, 2 x CH$_3$), 4.42 (m, 1H, CH), 5.75-5.81 (m, 1H, C=CH), 6.35-652 (m, 2H, 2 x C=CH), 7.22 (dd, 1H, J = 9.0, 2.4 Hz, ArH), 7.75 (d, 1H, J = 8.8 Hz, ArH), 8.77 (s, 1H, pyraz-H), 9.25 (s, 1H, pyraz-H), 9.34 (s, 1H, benzimid-H), 9.39 (br s, 1H, ArH). m/z (EI): 350 (M$^+$). |
| 6-[6-(Acryloylamino)-1H-benzimidazol-1-yl]-N,N-dimethylpyrazine-2-carboxamide | 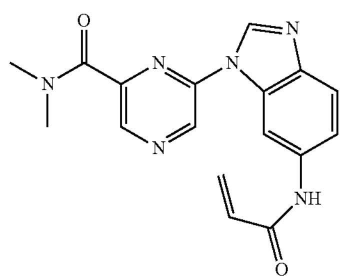 | $^1$H-n.m.r. CDCl$_3$ δ 3.23 (s, 6H, N(CH$_3$)$_2$), 5.79 (dd, 1H, J = 9.5, 2.3 Hz, C=CH), 6.33 (dd, 1H, J = 16.9, 9.5 Hz, C=CH), 6.47 (dd, 1H, J = 16.9, 2.1 Hz, C=CH), 7.22 (dd, 1H, J = 8.6, 2.2 Hz, ArH), 7.72 (d, 1H, J = 8.6 Hz, ArH), 8.05 (br s, 1H, CONH), 8.52 (s, 1H, pyraz-H), 8.75 (s, 1H, CONH), 8.87 (s, 1H, pyraz-H), 9.02 (s, 1H, benzimid-H). m/z (EI): 336 (M$^+$). |
| 6-[6-(But-2-ynoylamino)-1H-benzimidazol-1-yl]-N,N-dimethylpyrazine-2-carboxamide | 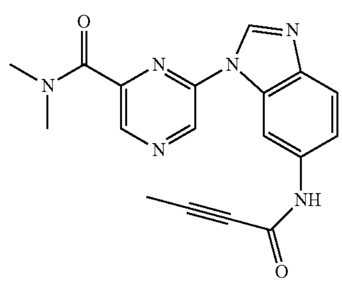 | $^1$H-n.m.r. CDCl$_3$ δ 2.04 (3, 3H, CH$_3$), 3.24, 3.26 (each s, 3H, NCH$_3$), 7.16 (dd, 1H, J = 8.8, 1.8 Hz, ArH), 7.75 (br s, 1H, CONH), 7.80 (d, 1H, J = 8.8 Hz, ArH), 8.54 (s, 1H, pyraz-H), 8.74 (d, 1H, J = 1.8 Hz, ArH), 8.91 (s, 1H, pyraz-H), 9.03 (s, 1H, benzimid-H). m/z (EI): 348 (M$^+$). |
| N-[1-(6-methoxypyridin-3-yl)-1H-benzimidazol-6-yl]acrylamide | 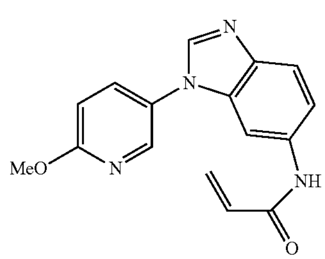 | $^1$H-n.m.r. (CDCl$_3$) δ 4.01 (s, 3H, OCH$_3$), 5.74 (dd, 1H, J = 9.9, 1.8 Hz, C=CH), 6.29 (dd, 1H, J = 16.8, 9.9 Hz, C=CH), 6.43 (dd, 1H, J = 16.8, 1.8 Hz, C=CH), 6.91 (d, 1H, J = 8.4 Hz, pyr-H), 7.11 (dd, 1H, J = 8.7, 2.1 Hz, benzimid-H), 7.70 (dd, 1H, J = 8.7, 2.7 Hz, pyr-H), 7.74 (d, 1H, J = 8.4 Hz, benzimid-H), 7.99 (s, 1H, benzimid-H), 8.07 (br s, 1H, CONH), 8.26 (br s, 1H, benzimid-H), 8.30 (d, 1H, J = 2.1 Hz, pyr-H). m/z (EI): 294 (M$^+$). |
| N-{1-(6-methoxypyridin-3-yl)-1H-benzimidazol-6-yl}but-2-ynamide | 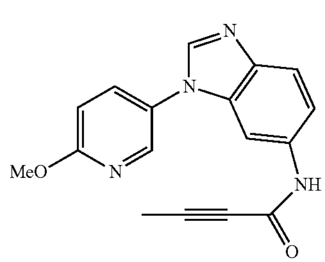 | $^1$H-n.m.r. (CDCl$_3$) δ 1.96 (s, 3H, CH$_3$), 4.01 (s, 3H, OCH$_3$), 6.92 (d, 1H, J = 8.7 Hz, pyr-H), 7.12 (dd, 1H, J = 8.7, 1.8 Hz, benzimid-H), 7.69 (dd, 1H, J = 8.7, 2.7 Hz, pyr-H), 7.76 (d, 1H, J = 8.7 Hz, benzimid-H), 7.99 (s, 1H, benzimid-H), 8.04-8.05 (m, 2H, CONH + benzimid-H), 8.30 (d, 1H, J = 2.4 Hz, pyr-H). m/z (EI): 306 (M$^+$). |

| Compound | Structure | Data |
|---|---|---|
| N-{1-[6-(tert-butylamino)pyrazin-2-yl]-1H-benzimidazol-6-yl}-4-morpholin-4-ylbut-2-ynamide | 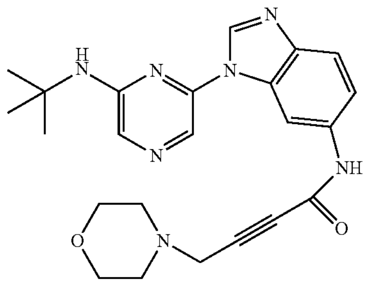 | ¹HNMR (CDCl₃/CD₃OD, v/v = 9/1) δ 1.51 (s, 9H, t-Bu), 2.65 (t, 4H, J = 4.8 Hz, 2 x NCH₂), 3.45 (s, 2H, NCH₂), 3.77 (t, 4H, J = 4.8 Hz, 2 x OCH₂), 7.33 (dd, 1H, J = 8.7, 1.8 Hz, benzimid-H), 7.75 (d, 1H, J = 8.7 Hz, benzimid-H), 7.82 (s, 1H, pyraz-H), 8.05 (s, 1H, pyraz-H), 8.45 (d, 1H, J = 1.8 Hz, benzimid-H), 8.52 (s, 1H, benzimid-H). m/z 433 (M⁺). |
| N-(1-[6-(tert-butylamino)pyrazin-2-yl]-1H-benzimidazol-6-yl)-4-(4-methylpiperazin-1-yl)-but-2-ynamide | 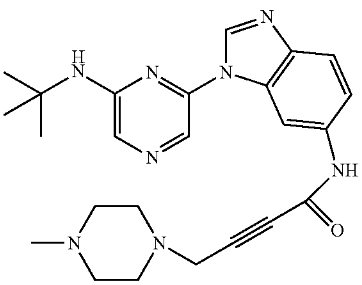 | ¹HNMR (CDCl₃) δ 1.52 (s, 9H, t-Bu), 2.51 (t, 4H, J = 5.1 Hz, 2 x NCH₂), 2.78 (s, 3H, NCH₃), 3.26 (t, 4H, J = 5.1 Hz, 2 x NCH₂), 3.50 (s, 2H, NCH₂), 4.86 (s, 1H, NH), 7.24 (dd, 1H, J = 8.7,1.8 Hz, benzimid-H), 7.78 (d, 1H, J = 8.7 Hz, benzimid-H), 7.84 (s, 1H, pyraz-H), 8.11 (s, 1H, pyraz-H), 8.17 (br s, 1H, CONH), 8.46 (d, 1H, J = 1.8 Hz, benzimid-H), 8.50 (s, 1H, benzimid-H). m/z 446 (M⁺). |
| N-[1-(6-(tert-butylamino)pyrazin-2-yl)-1H-benzimidazol-6-yl]-4-(diethylamino)but-2-ynamide | | ¹HNMR (CDCl₃) δ 1.11 (t, 6H, J = 7.2 Hz, 2 x CH₃), 1.53 (s, 9H, t-Bu), 2.62 (t, 4H, J = 7.2 Hz, 2 x NCH₂), 3.59 (s, 2H, NCH₂), 4.84 (s, 1H, NH), 7.21 (dd, 1H, J = 8.7, 1.8 Hz, benzimid-H), 7.76 (br s, 1H, CONH), 7.79 (d, 1H, J = 8.7 Hz, benzimid-H), 7.85 (s, 1H, pyraz-H), 8.12 (s, 1H, pyraz-H), 8.45 (d, 1H, J = 1.8 Hz, benzimid-H), 8.51 (s, 1H, benzimid-H). m/z 419 (M⁺). |
| N-[1-[6-(tert-butylamino)pyrimidin-4-yl]-1H-benzimidazol-6-yl]acrylamide | 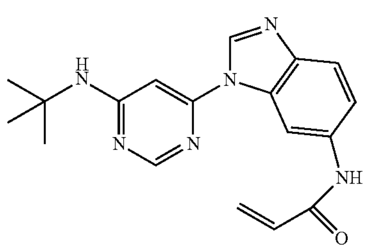 | ¹H-NMR(CDCl₃): δ 8.76 (b, 1H), 8.65 (s, 1H), 8.52 (s, 1H), 7.75 (d, J = 8.9 Hz, 1H), 7.73 (b, 1H, amide NH), 7.15 (dd, J = 6.6, 2.0 Hz, 1H), 6.58 (s, 1H), 6.47 (dd, J = 16.9,1.7 Hz, 1H), 6.30 (dd, J = 16.9, 9.6 Hz, 1H), 5.80 (dd, J = 9.6, 1.7 Hz, 1H), 5.41 (b, 1H, NH), 1.52 (s, 9H) ppm. m/z 336.3 |
| N-{1-(4-(tert-butylamino)pyrimidin-2-yl)1H-benzimidazol-6-yl}acrylamide | 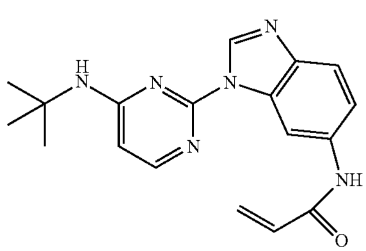 | ¹H-NMR(CDCl₃): δ 8.93 (s, 2H), 8.11 (d, J = 6.0 Hz, 1H), 7.78 (b, 1H, amide NH), 7.74 (d, J = 8.6 Hz, 1H), 7.51 (bm, 1H), 6.46 (dd, J = 16.9, 1.6 Hz, 1H), 6.32 (dd, J = 16.9, 10.0 Hz, 1H), 6.20 (d, J = 6.0 Hz, 1H), 5.75 (dd, J = 10.0, 1.6 Hz, 1H), 5.09 (b, 1H, NH), 1.51 (s, 9H) ppm. m/z 336.1 LC-MS: R_T = 7.6 min., |

| Compound | Structure | Data |
|---|---|---|
| N-{1-[6-(tert-butylamino)pyrazin-2-yl]-5-methoxy-1H-benzimidazol-6-yl)acrylamide | 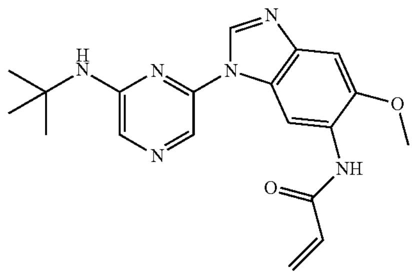 | $^1$HNMR (CDCl$_3$) δ 1.53 (s, 9H; C(CH$_3$)$_3$), 4.00 (s, 3H, OCH$_3$), 4.78 (s, 1H, NH), 5.78 (dd, 1H, J = 9.6, 1.8 Hz, C=CH), 6.33 (dd, 1H, J = 16.8, 9.6 Hz, C=CH), 6.44 (dd, 1H, J = 17.0, 1.8 Hz, C=CH), 7.35 (s, 1H, ArH), 7.83 (s, 1H, pyraz-H), 8.09 (br s, 1H, CONH), 8.19 (s, 1H, pyraz-H), 8.49 (s, 1H, ArH), 9.12 (s, 1H, benzimid-H). m/z (EI): 366 (M$^+$). |
| N-[1-(5-bromopyridin-3-yl)-1H-benzimidazol-6-yl]acrylamide | 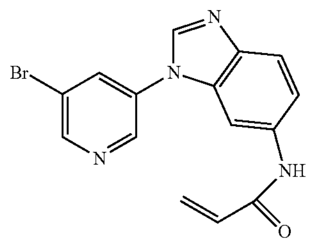 | $^2$H-n.m.r. (CDCl$_3$) d 5.79 (d, 1H, / = 10.2 Hz, C=CH), 6.27 (dd, 1H, / = 16.8, 10.2 Hz, C=CH), 6.45 (d, 1H, / = 16.8 Hz, C=CH), 7.16 (dd,1H, / = 8.7, 2.1 Hz, benzimid-H), 7.52 (br s, 1H, CONH), 7.80 (d, 1H, / = 8.4 Hz, benzimid-H), 8.03-8.05 (m, 2H), 8.30 (br s, 1H, benzimid-H), 8.77-8.80 (m, 2H, pyr-H). m/z 342, 344 (M$^+$) |
| N-[1-(6-bromopyridin-2-yl)1H-benzimidazol-6-yl)]acrylamide | 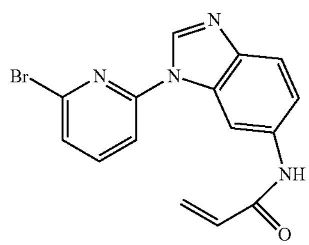 | m/z 342, 344 (M$^1$) |

Screening

Compound Dilution

For screening purposes, compounds were diluted in 96 well plates at a concentration of 20 μM. Plates were warmed at 37° C. for 30 minutes before assay.

JAK Tyrosine Kinase Domain Production

JAK kinase domains were produced in the following manner:

JAK1

The kinase domain of humanJAK1 was amplified from U937mRNA using the polymerase chain reaction with the following primers:

```
XHOI-J1
                                          (SEQ ID NO: 1)
5'-CCG CTC GAG ACT GAA GTG GAC CCC ACA CAT-3'

J1-KPNI
                                          (SEQ ID NO: 2)
5'-CGG GGT ACC TTA TTT TAA AAG TGC TTC AAA-3'
```

JAK1 PCR products were cloned into the pFastBac HTb expression vector (Gibco®) via the Xho I and Kpn I sites. The JAK1 plasmid was then transformed into competent DH10Bac cells (Gibco®), and the recombinant baculovirus produced prepared for transfection into Sf9 insect cells.

JAK2

The kinase domain of humanJAK2 was amplified from U937mRNA using the polymerase chain reaction with the following primers:

```
SALI-jk2
                                          (SEQ ID NO: 3)
5'-ACG CGT CGA CGG TGC CTT TGA AGA CCG GGA T-3' jk2-NOTI
                                          (SEQ ID NO: 4)
5'-ATA GTT TAG CGG CCG CTC AGA ATG AAG GTC ATT T-3'
```

JAK2 PCR products were cloned into the pFastBac HTc expression vector (Gibco®) via the Sal I and Not I sites. The JAK2 plasmid was then transformed into competent DH10Bac cells (Gibco®), and the recombinant baculovirus produced prepared for transfection into Sf9 insect cells.

JAK3

The kinase domain of humanJAK3 was amplified from U937mRNA using the polymerase chain reaction with the following primers:

```
XHOI-J3
                                          (SEQ ID NO: 5)
5'-CCG CTC GAG TAT GCC TGC AAA GAC CCC ACG-3'

J3-KPNI
                                          (SEQ ID NO: 6)
5'-CGG GGT ACC CTA TGA AAA GGA CAG GGA GTG-3'
```

JAK3 PCR products were cloned into the pFastBac HTb expression vector (Gibco®) via the Xho I and Kpn I sites. The JAK3 plasmid was then transformed into competent DH10Bac cells (Gibco®), and the recombinant baculovirus produced prepared for transfection into Sf9 insect cells.

TYK2

The kinase domain of humanTYK2 was amplified from A549 mRNA using the polymerase chain reaction with the following primers:

```
HT2EK
                                  (SEQ ID NO: 7)
5'-GGA GCA CTC GAG ATG GTA GCA CAC
AAC CAG GTG-3'

ITY2.2R
                                  (SEQ ID NO: 8)
5'-GGA GCA GGA ATT CCG GCG CTG CCG GTC
AAA TCT GG-3'
```

TYK2 PCR products were cloned into pBlueBacHis2A (Invitrogen) via the EcoRI site. The recombinant TYK2 baculovirus produced was prepared for transfection into Sf9 insect cells.

Large Scale Production of Kinase Domains

Baculovirus preparations from each of the JAK family members were infected into five litres of High Five cells (Invitrogen) grown in High Five serum free medium (Invitrogen) to a cell density of approximately $1-2\times10^6$ cells/ml. Cells are infected with virus at a MOI of 0.8-3.0. Cells were harvested and lysed. JAK kinase domains were purified by affinity chromatography on a Probond (Invitrogen) nickel chelate affinity column.

Assay Protocols

Kinase assays were performed in a 96 well capture-based ELISA assay or in 384 well Optiplates (Packard) using an Alphascreen Protein Tyrosine Kinase kit. In either case using approximately 1.5 μg of affinity purified PTK domain in the presence of 50 mM HEPES, pH 7.5, 10 mM $MgCl_2$, 150 mM NaCl and 10 μM-1 mM ATP. The biotinylated substrate biotin-EGPWLEEEEEAYGWMDF-$NH_2$ (SEQ ID NO:9) (final concentration 5 μM) was used as substrate. In the ELISA assay tyrosine phosphorylation was quantitated following transfer to an avidin coated ELISA plate using peroxidase-linked anti-phospho-tyrosine antibody PY20. In the Alphascreen assay, Alphascreen phosphotyrosine acceptor beads followed by streptavidin donor beads were added under subdued light. The ELISA plates were read on a BMG Fluorostar, the Alphascreen plates were read on a Packard Fusion Alpha. Inhibitors were added to the assays fifteen minutes prior to the addition of ATP. Inhibitors were added in aqueous DMSO, with DMSO concentrations never exceeding 1%.

Results

The activity of selected compounds is shown in Table 3. Compounds that exhibited a capacity to inhibit 50% of JAK activity at a concentration of 20 μM (measured under standard conditions, see Methods), are designated as "+".

TABLE 3

| CHEMISTRY | Jak2 | Jak3 |
|---|---|---|
| C14H10ClN5O | − | + |
| C22H20N6O | + | + |
| C17H18N6O | − | + |
| C20H13ClFN5O | − | + |
| C17H13N7O | − | + |
| C18H20N6O | − | + |

TABLE 3-continued
| CHEMISTRY | Jak2 | Jak3 |
|---|---|---|
| 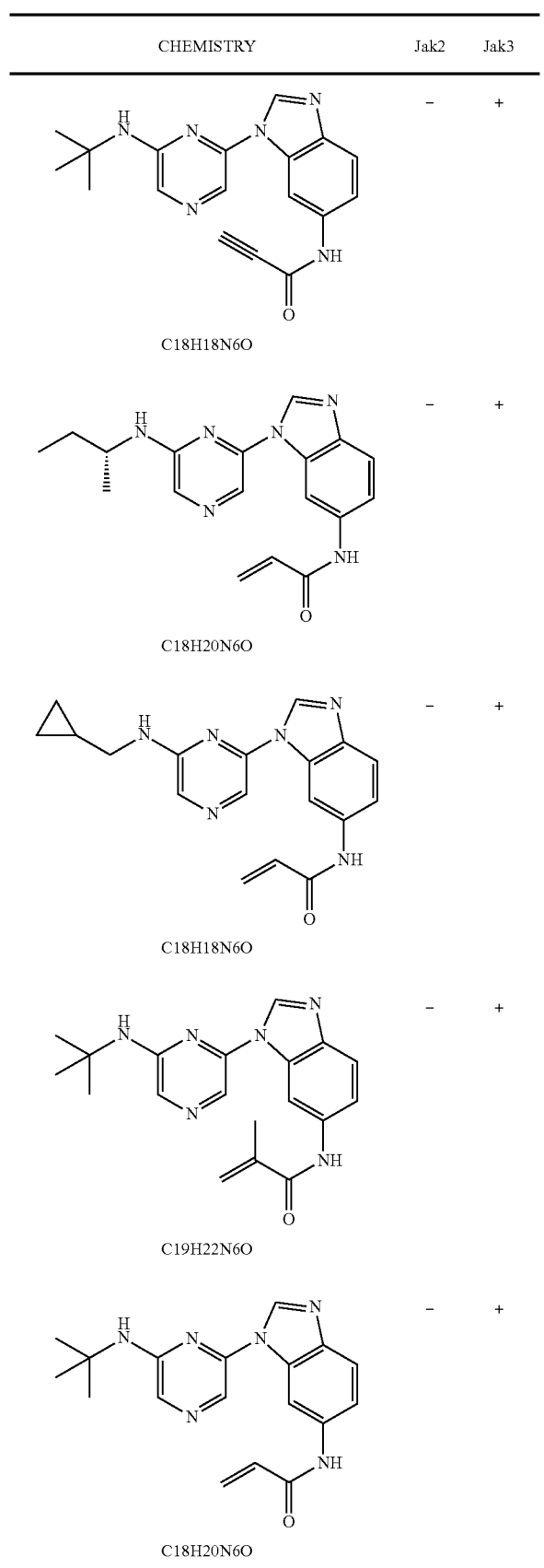 | | |
TABLE 3-continued
| CHEMISTRY | Jak2 | Jak3 |
|---|---|---|
| 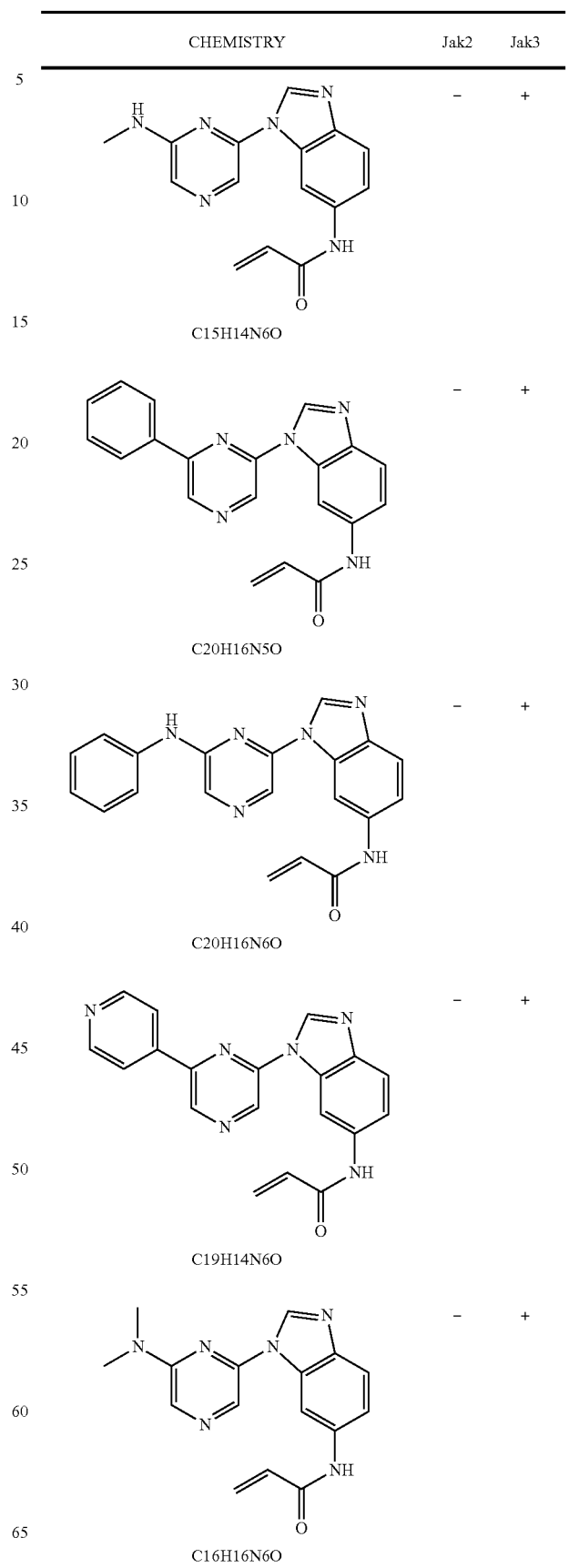 | | |

TABLE 3-continued

| CHEMISTRY | Jak2 | Jak3 |
|---|---|---|
| 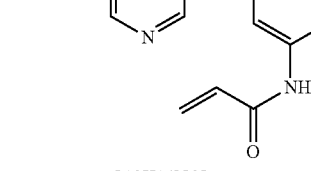 C19H14N6O | − | + |
| C18H18N6O | − | + |
| C19H15N5O2 | − | + |
| C18H18N6O2 | − | + |
| C18H13N5OS | − | + |
| 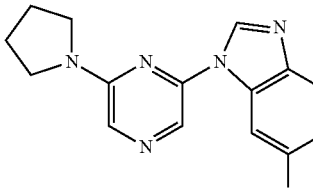 C19H20N6O | − | + |
| C19H21N7O | − | + |
| C18H20N8O | − | + |

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Discafani C M, Carroll M L, Floyd M B Jr, Hollander I J, Husain Z, Johnson B D, Kitchen D, May M K, Malo M S, Minnick A A Jr, Nilalumbart R, Shen R, Wang Y F, Wissner A, and Greenberger L M. (1999) Irreversible inhibition of epidermal growth factor receptor tyrosine kinase with in vivo activity by N-[4-[(3-bromophenyl)amino]-6-quinazolinyl]-2-butynamide (CL-387,785). *Biochem Pharmacol.* 57, 917-25.
2. Pinet, J.-P., Fedorov, A. Y., Combes, S., and Boyer, G. (2002) Recent Advances in Ullmann Reaction: Copper (II) Diacetate Catalysed N-, O- and S-Arylation Involving Polycoordinate Heteroatomic Derivatives. *Curr. Org. Chem.* 6, 597-626.
3. Fry D W, Bridges A J, Denny W A, Doherty A, Grab K D, Hicks J L, Hook K E, Keller P R, Leopold W R, Loo J A, McNamara D J, Nelson J M, Sherwood V, Smaill J B, Trumpp-Kallmeyer S, and Dobrusin E M. (1998) Specific, irreversible inactivation of the epidermal growth factor receptor and erbB2, by a new class of tyrosine kinase inhibitor. *Proc Natl Acad Sci USA.* 95, 12022-7.
4: Havens C M, Stacker S A, Andres A C, Harpur A G, Ziemiecki A, and Wilks A F. (1992) RYK, a receptor tyrosine kinase-related molecule with unusual kinase domain motifs. *Proc Natl Acad Sci USA.* 89, 1181-22.
5. Kozma S C, Redmond S M, Pu X C, Saurer S M, Groner B, and Hynes N E. (1988) Activation of the receptor kinase domain of the trk oncogene by recombination with two different cellular sequences. *EMBO J.* 7, 147-54.
6. Kumada, M.; Tamao, K.; Sumitani, K. (1988) Phosphine-Nickel complex catalysed cross-coupling of Grignard reagents with aryl and alkenyl halides: 1,2-Dibutylbenzene. *Org. Synth. Coll. Vol.* 6, 407.
7. Levitzki A. (2000) Protein Tyrosine Kinase Inhibitors as Therapeutic Agents. *Top. Curr. Chem.* 211, 1-15.
8. Miyaura, N. and Suzuki, A. Palladium-Catalyzed Cross-Coupling Reactions of Organoboron Compounds (1995) *Chem Rev.* 95, 2457
9. Negishi, E. (2002) A genealogy of Pd-catalyzed cross-coupling. *J. Organomet. Chem.* 653, 34-40
10. Russell S M, Tayebi N, Nakajima H, Riedy M C, Roberts J L, Aman M J, Migone T S, Noguchi M, Markert M L, Buckley R H, et al (1995) Mutation of Jak3 in a patient with SCID: essential role of Jak3 in lymphoid development. *Science,* 270, 797-800.
11. Sadowski I, Stone J C, and Pawson T. (1986) A noncatalytic domain conserved among cytoplasmic protein-tyrosine kinases modifies the kinase function and transforming activity of Pujinami sarcoma virus P130gag-fps. *Mol Cell Biol.* 6, 4396-408.
12. Smaill, J. B.; Palmer, B. D.; Rewcastle, C. W.; Denny, W. A.; McNamara, D. J.; Dobrusin, E. M.; Bridges, A. J.; Zhou, H.; Showalter, H. D. H.; Winters, R. T.; Leopold, W. R.; Pry, D. W.; Nelson, J. M.; Slintak, V.; Elliot, W. L.; Roberts, B. J.; Vincent, P. W.; Patmore, S. J. (1999) Tyrosine Kinase Inhibitors. 15. 4-(Phenylamino)quinazoline and 4-(Phenylamino)pyrido[d]pyrimidine Acrylamides as irreversible inhibitors of the ATP Binding Site of the Epidermal Growth Factor Receptor *J. Med. Chem.,* 42, 1803-1815.
13. Smaill, J. B.; Rewcastle, G. W.; Loo, J. A.; Greis, K. D.; Chan. O. H.; Reyner, E. L.; Lipka, B.; Showalter, H. D. H.; Vincent, P. W.; Elliott, W. L; Denny, W. A. (2000) Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions J. Med. Chem., 93, 1380-1397.
14. Sinai % J. B.; Showalter, H. D. H.; Zhou, H.; Bridges, A. J.; McNamara, D. J.; Pry, D. W.; Nelson, J. M.; Sherwood, V.; Vincent, P. W.; Roberts, B. J.; Elliott, W. L.; Denny, W. A. (2001) Tyrosine Kinase Inhibitors. 18. 6-Substituted 4-Anilinoquinazolines and 4-Anilinopyrido[3,4-d]pyrimidines as Soluble, Irreversible Inhibitors of the Epidermal Growth Factor Receptor *J. Med. Chem.,* 44, 429-440.
15. Spiotto M T, and Chung T D. (2000) STAT3 mediates IL-6-induced growth inhibition in the human prostate cancer cell line LNCaP. *Prostate* 42, 88-98
16. Stile, J. K. (1986). The Palladium-Catalysed Cross-Coupling Reactions of Organotin Reagents with Organic Electrophiles. *Angew. Chem., Int. Ed. Engl.* 25, 508
17. Tsou, H.-R.; Mamuya, N.; Johnson, B. D.; Reich, M. F.; Gruber, B. C.; Ye, F.; Nilakantan, R.; Shen, R.; Discafani, C.; DeBlanc, R.; Davis, R.; Koehn, F. E.; Greenberger, L. M.; Wang, Y.-F.; and Wissner, A. (2001) 6-Substituted-4-(3-bromophenylamino)quinazolines as Putative Irreversible Inhibitors of the Epidermal Growth Factor Receptor (EGFR) and Human Epidermal Growth Factor Receptor (HER-2) Tyrosine Kinases with Enhanced Antitumor Activity *J. Med. Chem.,* 44, 2719-2734.
18. Wilks A F, Harpur A G, Kurban R R, Ralph S J, Zurcher G, Ziemiecki A. (1991) Two novel protein-tyrosine kinases, each with a second phosphotransferase-related catalytic domain, define a new class of protein kinase. *Mol Cell Biol.* 2057-65.
19. Wilks A F, and Kurban R R (1988) Isolation and structural analysis of murine c-fes cDNA clones. *Oncogene* 3, 289-94
20. Wissner, A.; Overbeek, E.; Reich, M. F.; Floyd, M. B.; Johnson, B. D.; Mamuya, N.; Rosfjord, E. C.; Discafani, C.; Davis, R.; Shi, X.; Rabindran, S. K; Gruber, B. C.; Ye, F.; Hallett, W. A.; Nilakantan, R.; Shen, R.; Wang, Y.-P.; Greenberger, L. M.; and Tsou, H.-R. (2003) Synthesis and Structure-Activity Relationships of 6,7-Disubstituted 4-Anilinoquinoline-3-carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2) *J. Med. Chem.* 46, 49-63.

The invention claimed is:

1. A Janus kinase inhibitor compound of formula I

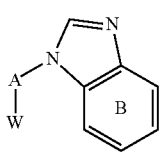

I or a pharmaceutically acceptable salt or diastereomer thereof, wherein:

one carbon of ring B is substituted with Z and the rest of the carbons are independently substituted with Y;

A is a ring selected from:

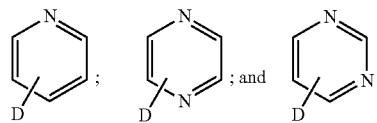

where D is selected from H, $C_{1-4}$ alkyl, halogen, and amino;

W is:

(i) $NR^1R^2$ where $R^1$ and $R^2$ are independently H, $C_{1-4}$ alkyl, $C_{1-4}$ alkyl$CF_3$, aryl, hetaryl, $C_{1-4}$ alkylaryl, $C_{1-4}$ alkyl-hetaryl, $C_{3-8}$ cycloalkyl, $C_{2-6}$ alkenyl, cyclohetalkyl, $C_{1-4}$ alkylcycloalkyl, $C_{1-4}$ alkyl cyclohetalkyl, or $R^1$ and R² are joined to form a 3-8 membered ring optionally containing an atom selected from O, S, and NR³; and R³ is selected from H, $C_{1-4}$ alkyl, aryl, hetaryl, $C_{1-4}$ alkyl aryl, $C_{1-4}$ alkyl hetaryl, and COR⁴ where R⁴ is selected from H, $C_{1-4}$ alkyl, aryl, and hetaryl; or (ii) H, $C_{1-4}$ alkyl, aryl, hetaryl, $C_{3-8}$ cycloalkyl, cyclohetalkyl, $C_{1-4}$ alkylaryl, $C_{1-4}$ alkylhetaryl, $C_{3-8}$ cycloalkyl, $C_{1-4}$ alkylcycloalkyl, or $C_{1-4}$ alkyl cyclohetalkyl;

Y is H, halogen, CN, CF₃, nitro, OH, $C_{1-4}$ alkyl, $C_{1-4}$ alkylNR⁵R⁶, $C_{1-4}$ alkylhetaryl, $OC_{1-4}$ alkyl, $OC_{2-4}$ alkyl$OC_{1-4}$alkyl, $OC_{1-4}$ alkylNR⁵R⁶, $OC_{1-4}$ alkylhetaryl, $OC_{1-4}$ alkylcyclohetalkyl, $SC_{1-4}$ alkyl, $SC_{2-4}$ alkyl$OC_{1-4}$ alkyl, $SC_{1-4}$ alkylNR⁵R⁶, NR⁵R⁶, NR⁵COR⁶, or NR⁵SO₂R⁶; and R⁵ and R⁶ are each independently H, $C_{1-4}$ alkyl, or may be joined to form a 3-6 membered ring optionally containing an atom selected from O, S, and NR⁷ and R⁷ is selected from H, $C_{1-4}$ alkyl, aryl, hetaryl, $C_{1-4}$ alkylaryl, and $C_{1-4}$ alkylhetaryl;

Z is selected from:

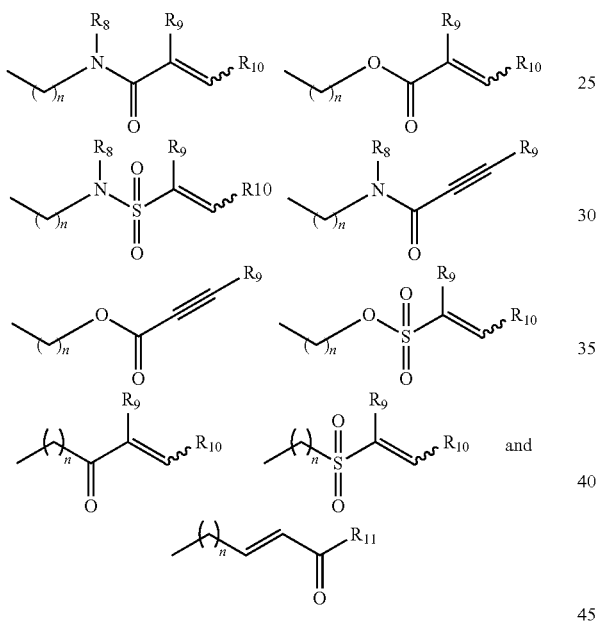

where R⁸ is selected from H and $C_{1-4}$ alkyl;
R⁹ and R¹⁰ are independently selected from H, $C_{1-4}$ alkyl, $C_{1-4}$ alkylNR¹²R¹³, $C_{1-4}$ alkylOR¹², and $C_{1-4}$ alkylhetaryl or may be joined to form a 5-8 membered ring containing an atom selected from SO, or SO₂;
R¹¹ is selected from OH, $OC_{1-4}$ alkyl, and NR¹²R¹³;
n is 0, 1, 2, 3, or 4;
where R¹² and R¹³ are independently selected from H and $C_{1-4}$ alkyl, or may be joined to form a 3-8 membered ring optionally containing an atom selected from O, S, and NR¹⁴; and R¹⁴ is selected from H and $C_{1-4}$ alkyl.

2. A compound according to claim 1 wherein Z is selected from:

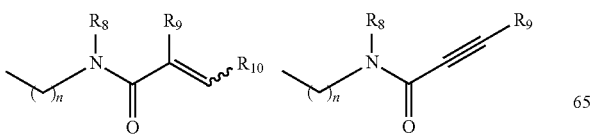

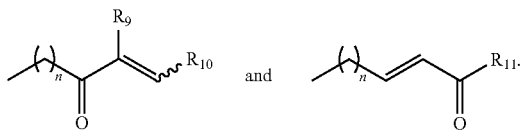

3. A pharmaceutical composition comprising a carrier and a compound according to claim 1.

4. A compound selected from the group consisting of:

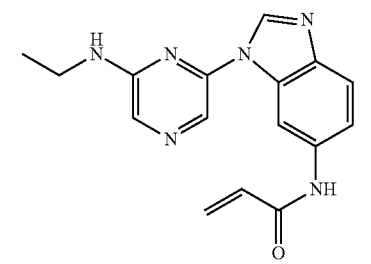

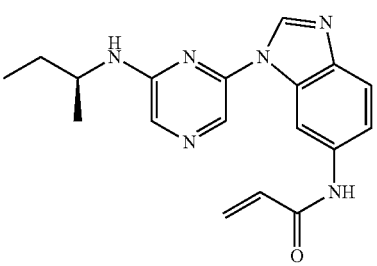

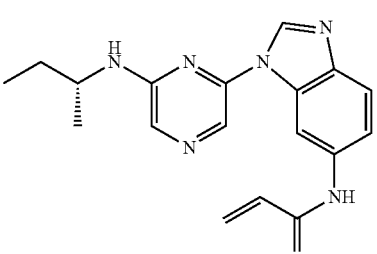

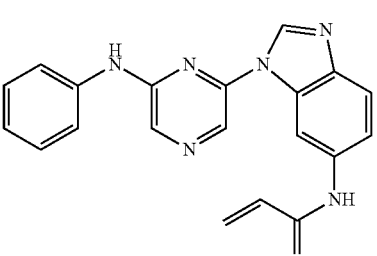

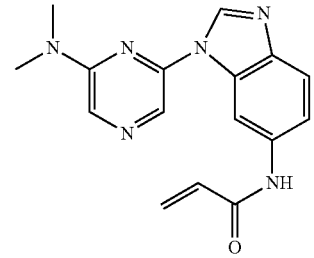

79
-continued
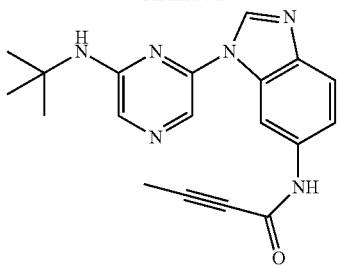
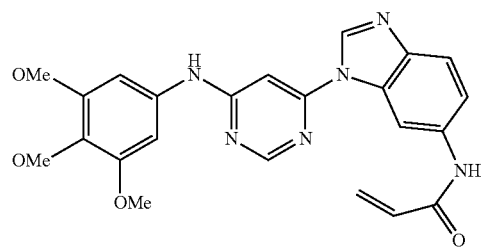
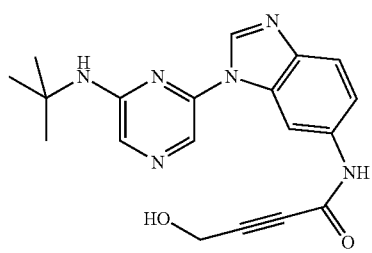
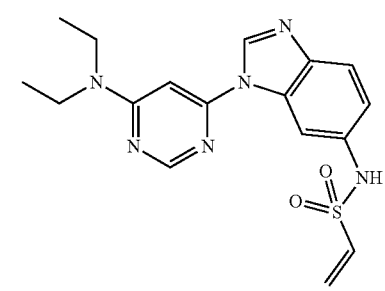
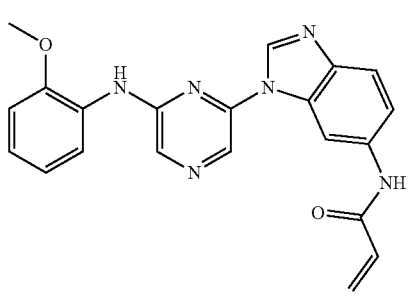
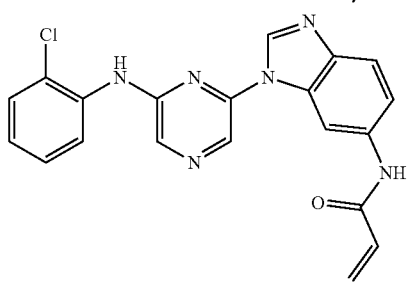
80
-continued
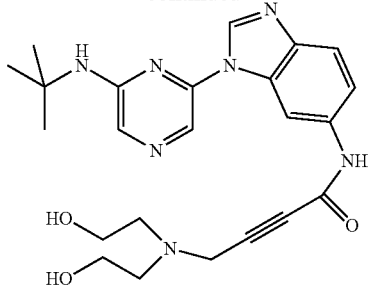
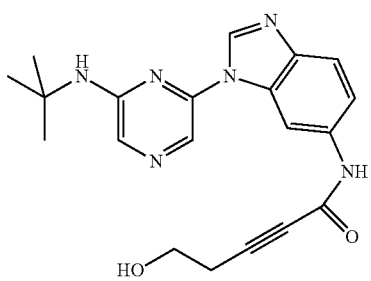
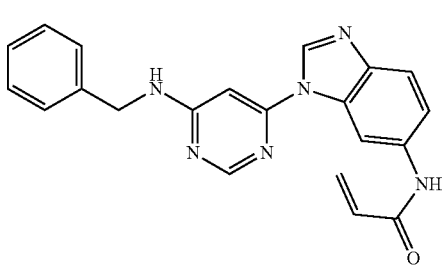
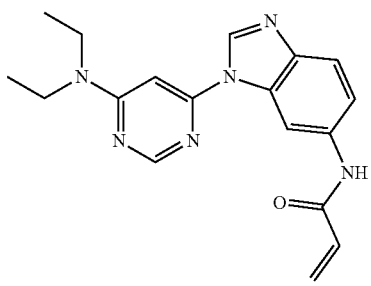
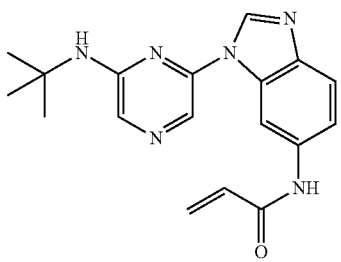
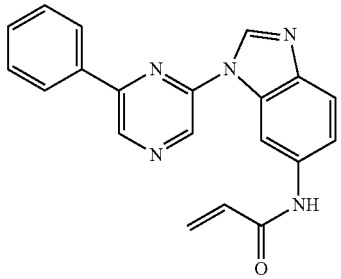

-continued
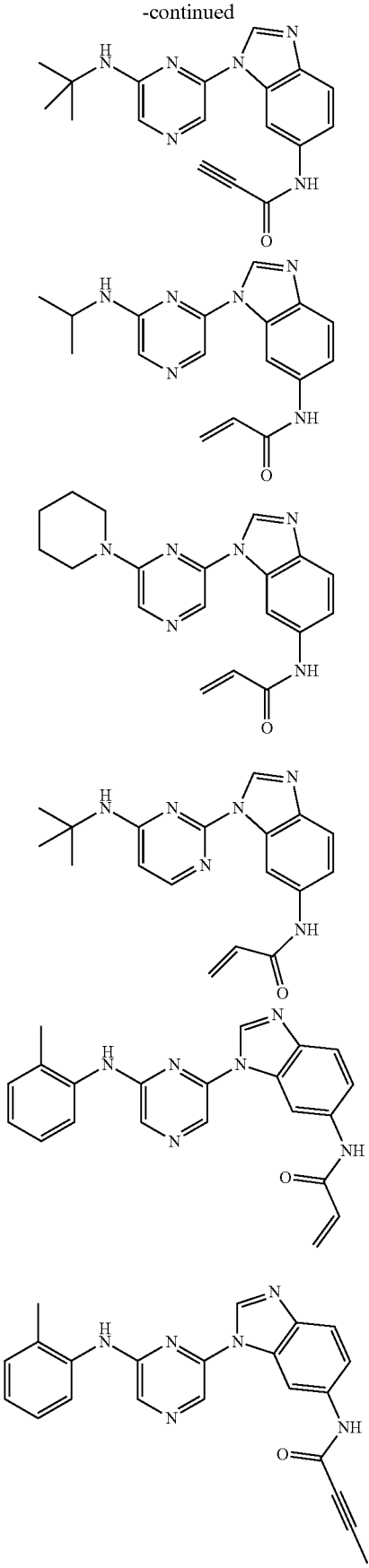
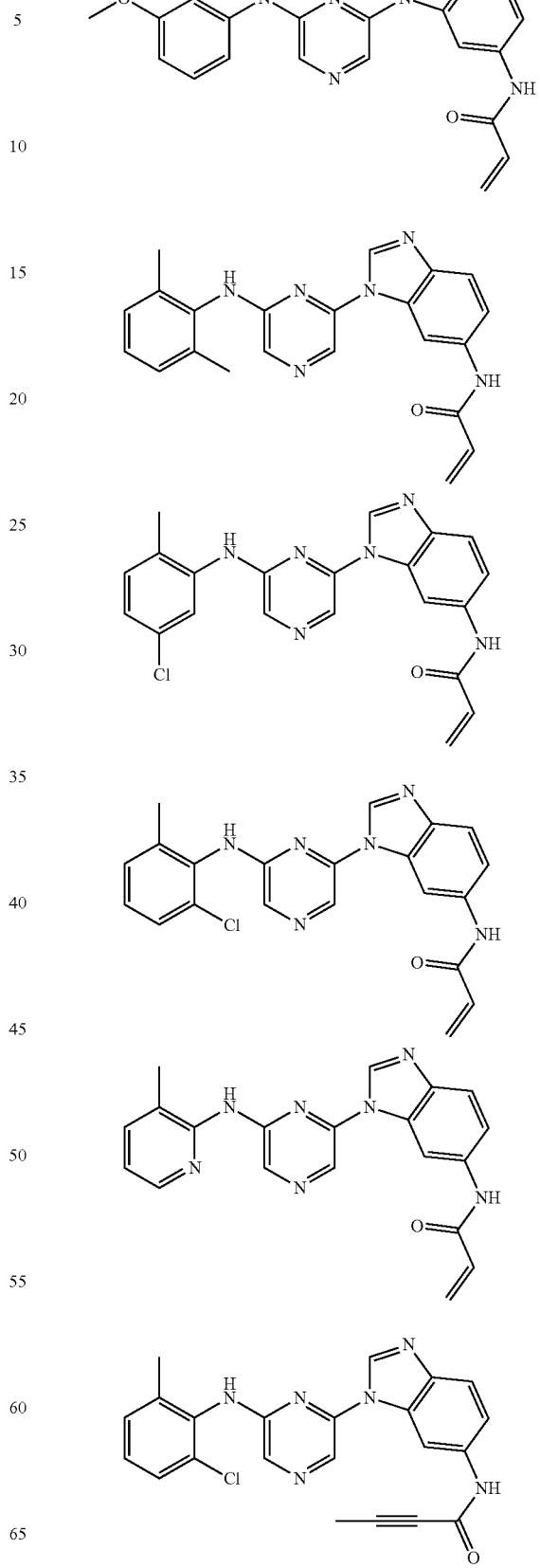

-continued
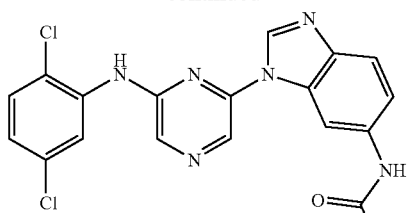
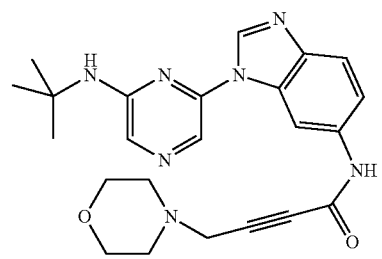
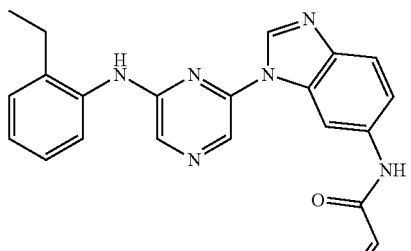
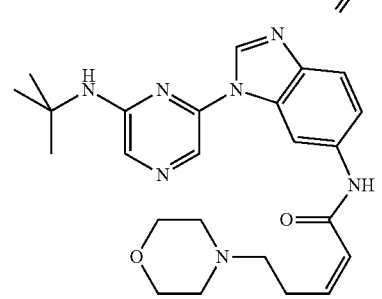
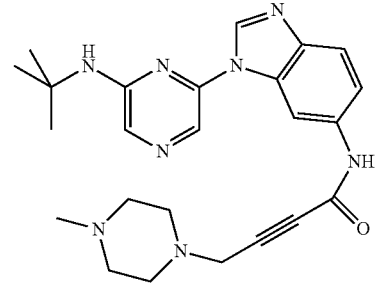
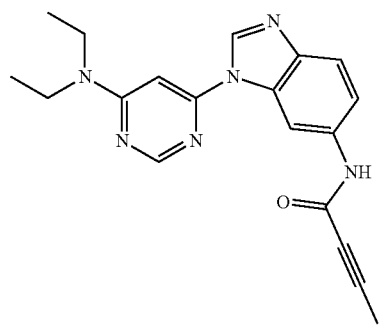
-continued
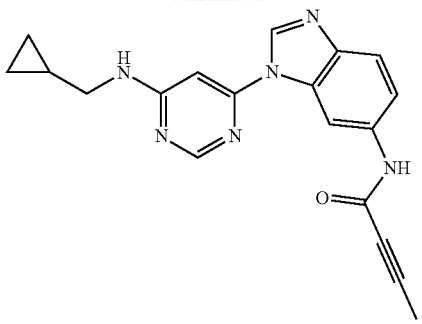
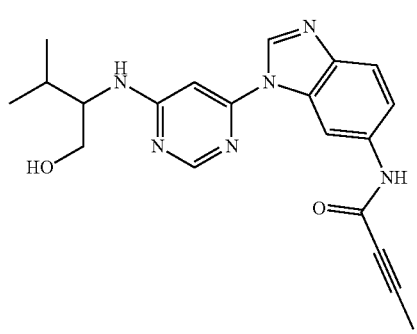
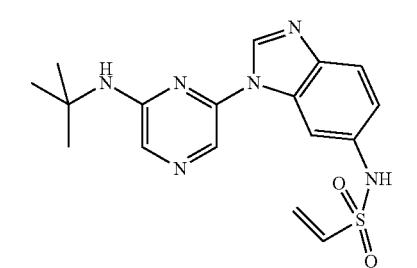
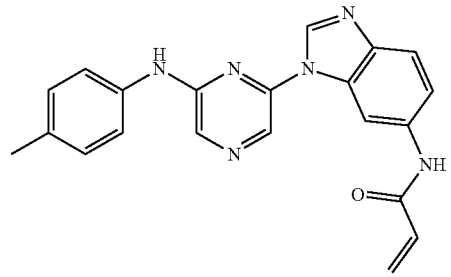
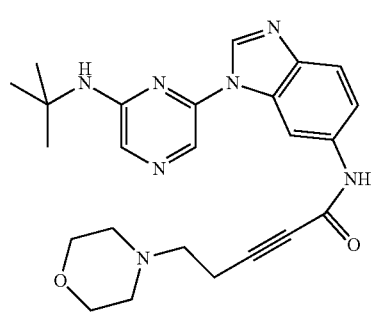

85
-continued
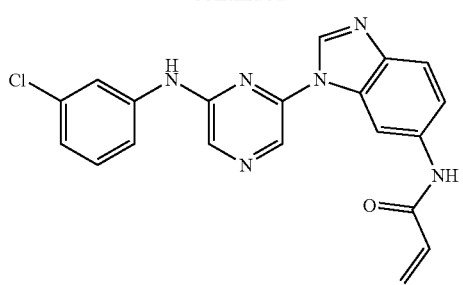
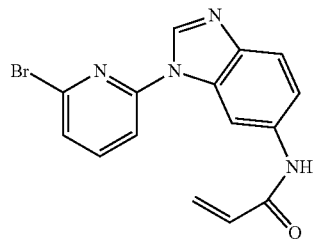
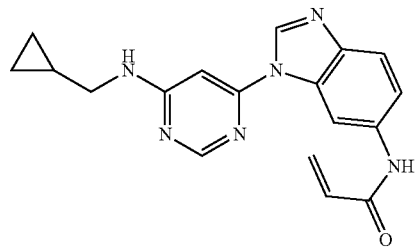
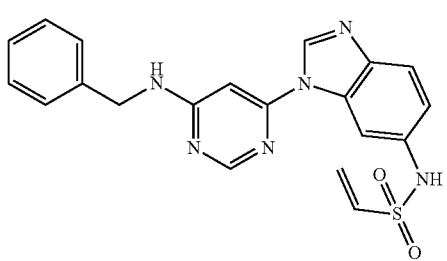
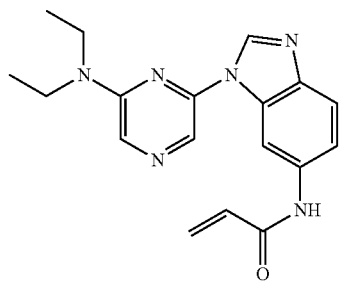
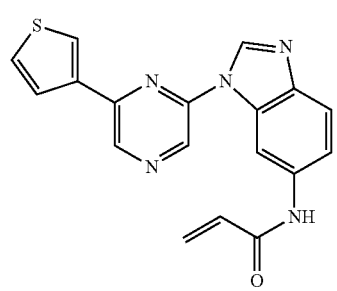
86
-continued
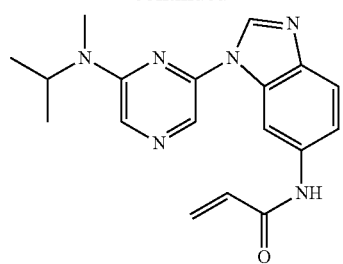
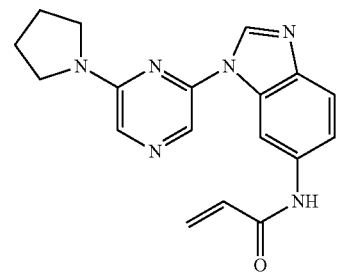
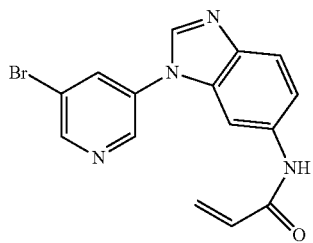
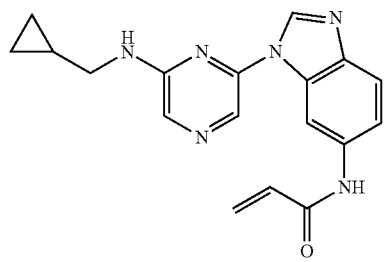
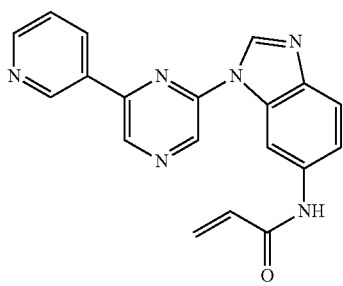
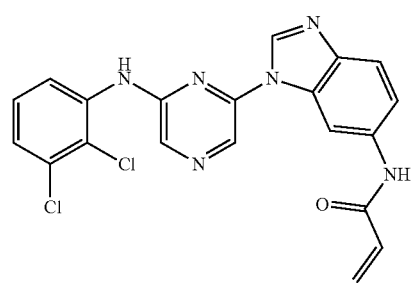

87
-continued
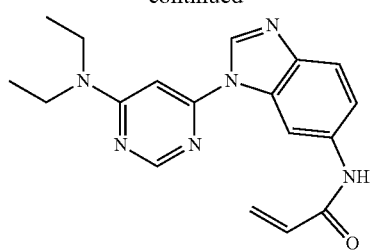
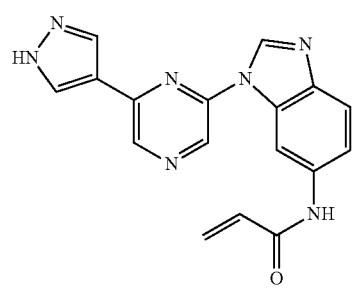
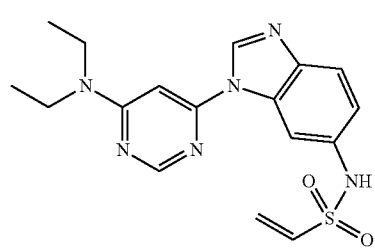
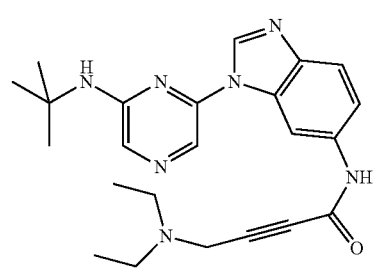
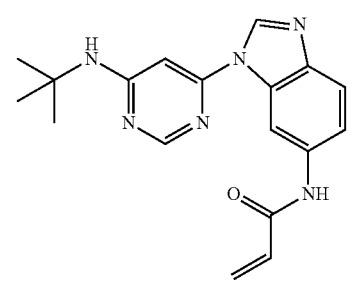
88
-continued
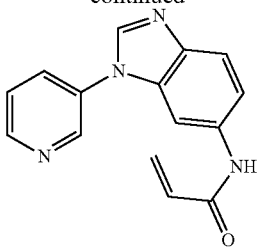
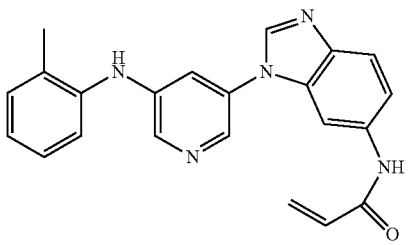
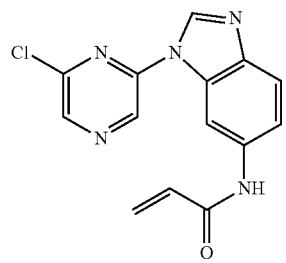
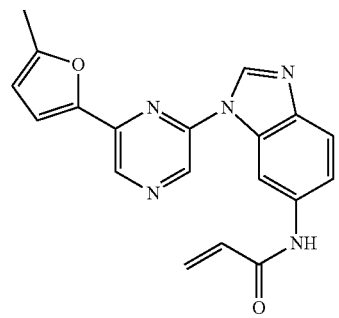
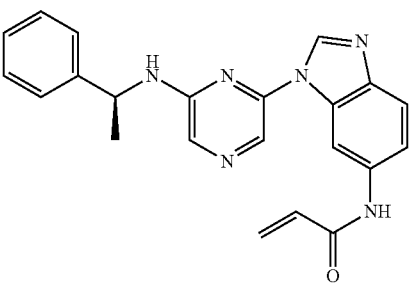

| 89 -continued | 90 -continued |
|---|---|
| 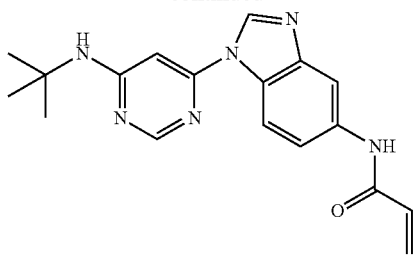 | 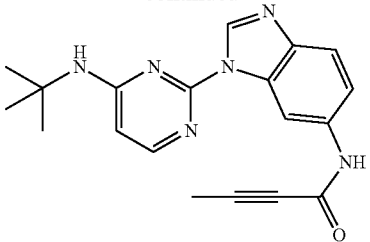 |
| 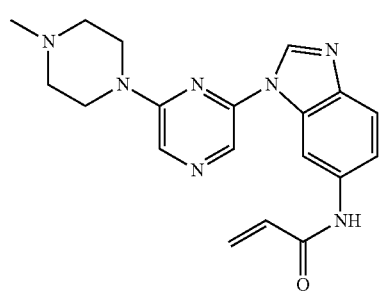 | 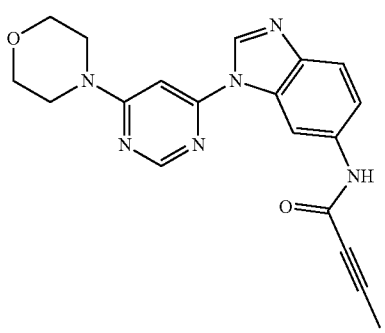 |
| 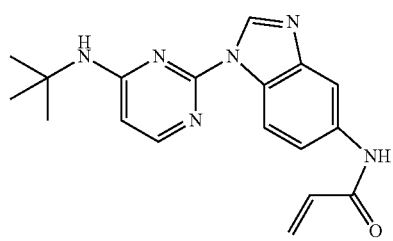 | 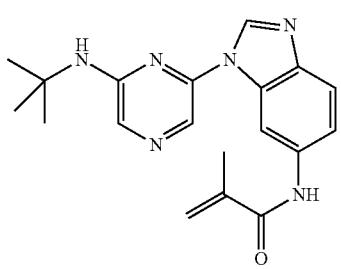 |
| 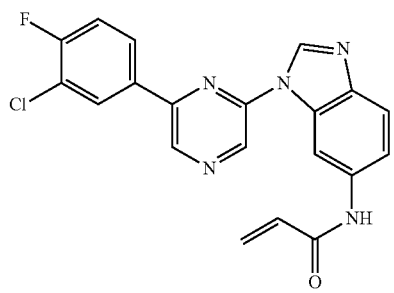 | 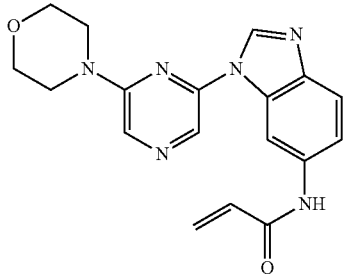 |
| 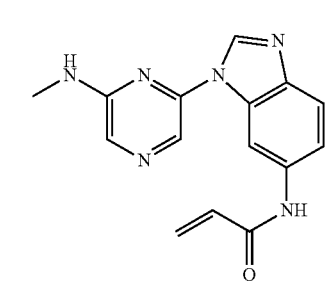 | 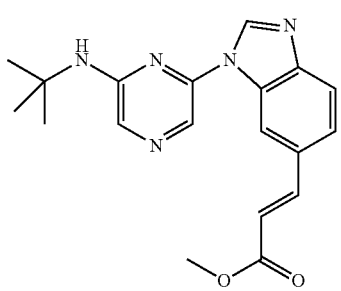 |

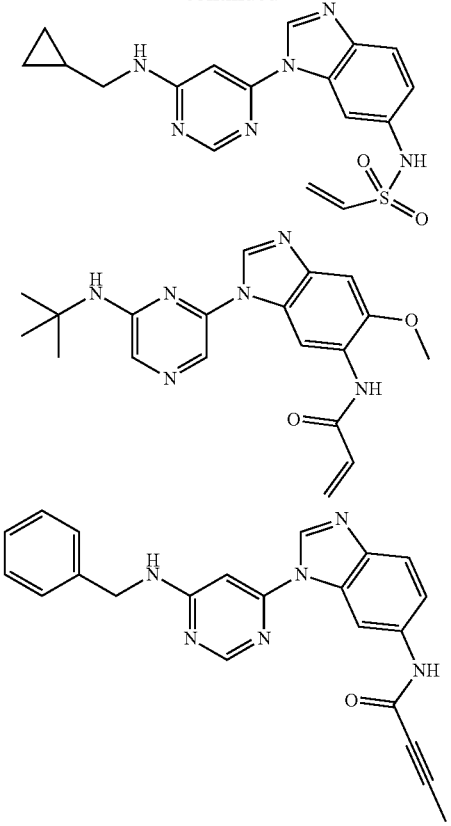
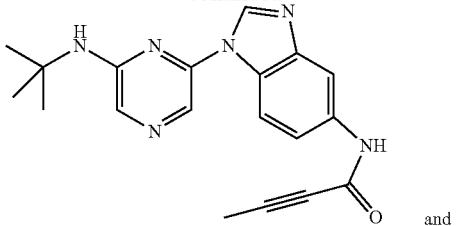
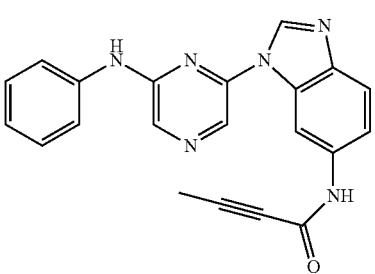
and pharmaceutically acceptable salts and diastereomers thereof.
* * * * *